(12) United States Patent
Zhang et al.

(10) Patent No.: US 7,361,489 B2
(45) Date of Patent: Apr. 22, 2008

(54) NUCLEIC ACID AMPLIFICATION METHODS

(75) Inventors: David Y. Zhang, Jamaica, NY (US); Wandi Zhang, New York, NY (US); Jizu Yi, Bayside, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 425 days.

(21) Appl. No.: 10/719,480

(22) Filed: Nov. 21, 2003

(65) Prior Publication Data

US 2004/0137484 A1 Jul. 15, 2004

Related U.S. Application Data

(63) Continuation-in-part of application No. 09/978,261, filed on Oct. 15, 2001, and a continuation-in-part of application No. PCT/US02/32754, filed on Oct. 11, 2002.

(51) Int. Cl.
  *C12P 19/34* (2006.01)
  *C12Q 1/68* (2006.01)
  *C07H 21/02* (2006.01)
  *C07H 21/04* (2006.01)
  *C07H 21/00* (2006.01)

(52) U.S. Cl. .................. 435/91.2; 435/6; 435/91.1; 536/23.1; 536/24.3; 536/24.33; 536/25.3

(58) Field of Classification Search .............. 435/6, 435/91.1, 91.2, 183; 436/94; 536/23.1, 536/24.3, 24.33, 25.3, 25.32
See application file for complete search history.

(56) References Cited

U.S. PATENT DOCUMENTS

| 5,567,583 | A | | 10/1996 | Wang | |
|---|---|---|---|---|---|
| 5,837,469 | A | * | 11/1998 | Harris | .......................... 435/6 |
| 5,942,391 | A | * | 8/1999 | Zhang et al. | ................. 435/6 |
| 2007/0015180 | A1 | | 1/2007 | Sorge | |

FOREIGN PATENT DOCUMENTS

WO  WO 99/49293 A2  9/1999

OTHER PUBLICATIONS

Thomas, David C. et al., "Amplication of padlock probes for DNA diagnostics by cascade rolling circle amplication or the polymerase chain reaction", Archives of Pathology and Lab. Med., vol. 123, No. 12, Dec. 1999 pp. 1170-1176.
Kenworthy, Anne K: "Imaging protein-protein interactions using fluorescence resonance energy transfer microscopy", Methods (Orlando), vol. 24, No. 3, Jul. 2001, pp. 289-296.

(Continued)

*Primary Examiner*—Frank Lu
(74) *Attorney, Agent, or Firm*—Stroock & Stroock & Lavan LLP

(57) ABSTRACT

The present invention relates to assays and kits for carrying out said assays for the rapid, automated detection of infectious pathogenic agents and normal and abnormal genes. The present invention further relates to methods for general amplification of genomic DNA and total mRNAs and for analyzing differential mRNA expression using the amplification methods disclosed herein.

6 Claims, 28 Drawing Sheets

OTHER PUBLICATIONS

Lizardi, PM, et al., Mutation Detection and Single-Molecule Counting Using Isothermal Rolling-Circle Amplification, Nature Genetics, NY, NY, vol. 19:No. 3, Jul. 1998 pp. 225-232.

Strizhkov, Boris N., et al., "PCR amplification on a microarray of gel-immobilized oligonucleotides:Detection of bacterial toxin-and drug-resistant genes and their mutations", Biotechniques, Informa Life Sciences Publishing, Westborough, MA, US, vol. 29, No. 4, Oct. 2000, pp. 844-857.

Schweitzer, Barry et al., "Immunoassays with rolling circle DNA amplification: A versatile platform for ultrasensitive antigen detection", Proceedings of the Natl Sci. of the USA, vol. 97, No. 18, Aug. 29, 2000, pp. 10113-10119.

Yi, Jizu et al.: "Molecular Zipper: a fluorescent probe for real-time isothermal DNA amplification", Nucleic Acids Research, vol. 34, No. 11, 2006.

* cited by examiner

FIG. 1
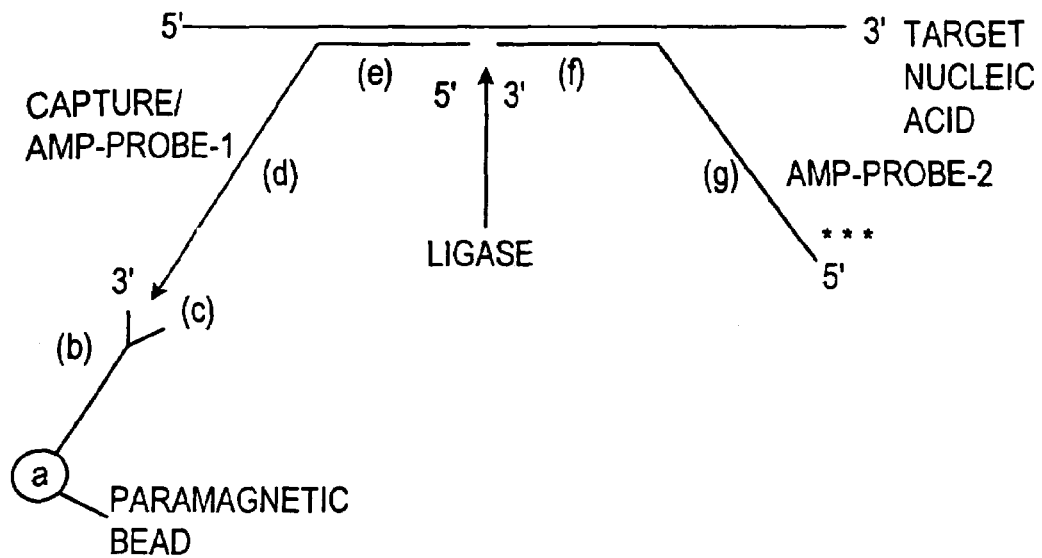
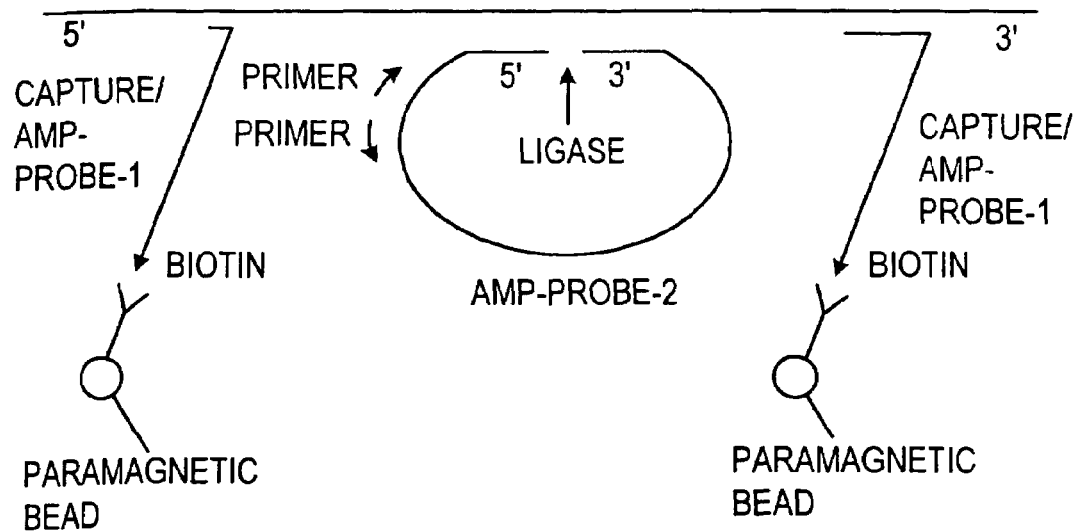
FIG. 7

FIG. 14
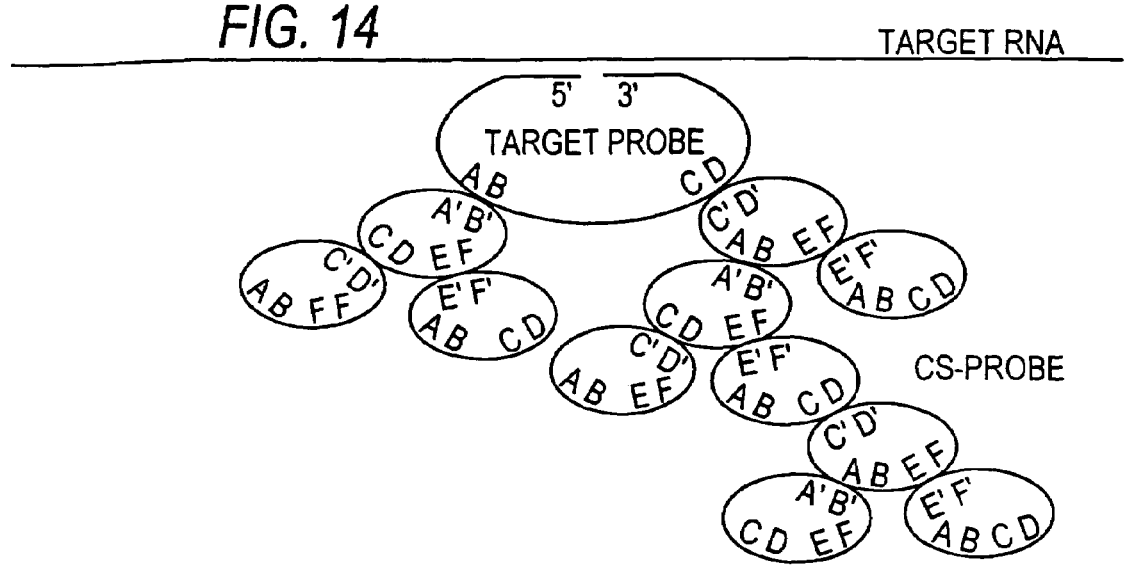
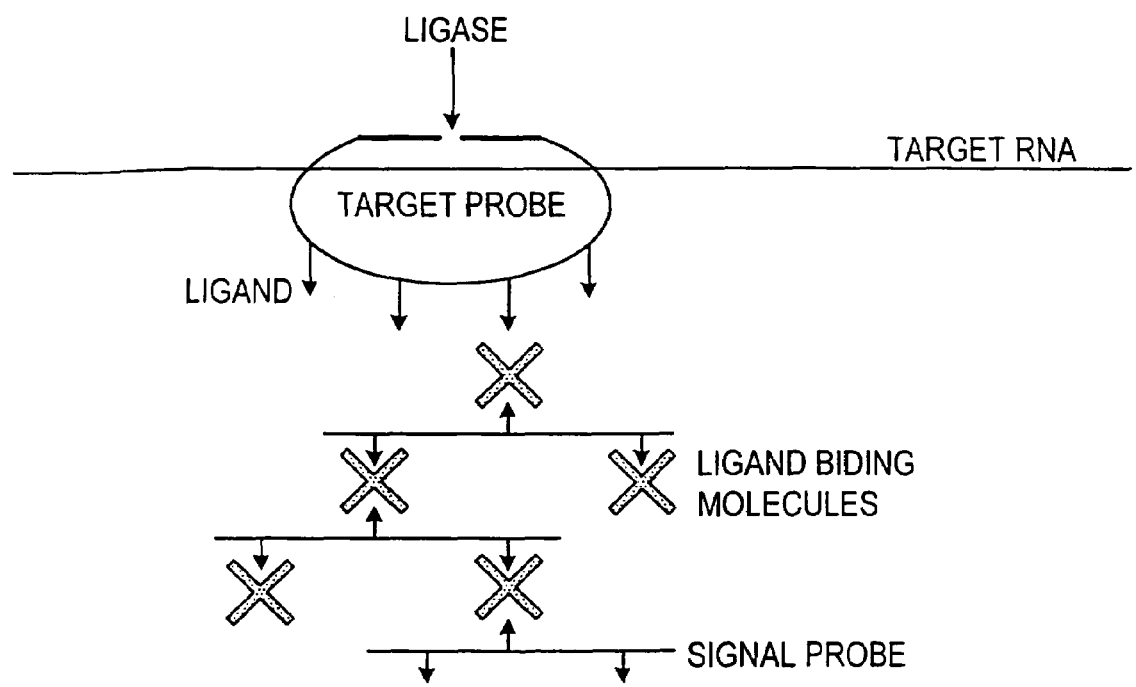
FIG. 15

NUCLEIC ACID AMPLIFICATION METHODS

The present application is a continuation-in-part of pending International Application PCT/US02/32754 filed Oct. 11, 2002 and to U.S. application Ser. No. 09/978,261 filed Oct. 15, 2001, now pending, the contents of which are incorporated herein.

INTRODUCTION

The present invention relates to assays and kits for carrying out said assays for the rapid, automated detection of infectious pathogenic agents and normal and abnormal genes. The present invention further relates to methods for general amplification of genomic DNA and total mRNAs and for analyzing differential mRNA expression using the amplification methods disclosed herein.

BACKGROUND OF THE INVENTION

A number of techniques have been developed recently to meet the demands for rapid and accurate detection of infectious agents, such as viruses, bacteria and fungi, and detection of normal and abnormal genes. Such techniques, which generally involve the amplification and detection (and subsequent measurement) of minute amounts of target nucleic acids (either DNA or RNA) in a test sample, include inter alia the polymerase chain reaction (PCR) (Saiki, et al., Science 230:1350, 1985; Saiki et al., Science 239:487, 1988; PCR Technology, Henry A. Erlich, ed., Stockton Press, 1989; Patterson et al., Science 260:976, 1993), ligase chain reaction (LCR) (Barany, Proc. Natl. Acad. Sci. USA 88:189, 1991), strand displacement amplification (SDA) (Walker et al., Nucl. Acids Res. 20:1691, 1992), Qβreplicase amplification (QβRA) (Wu et al., Proc. Natl. Acad. Sci. USA 89:11769, 1992; Lomeli et al., Clin. Chem. 35:1826, 1989) and self-sustained replication (3SR) (Guatelli, et al., Proc. Natl. Acad. Sci. USA 87:1874-1878, 1990). While all of these techniques are powerful tools for the detection and identification of minute amounts of a target nucleic acid in a sample, they all suffer from various problems, which have prevented their general applicability in the clinical laboratory setting for use in routine diagnostic techniques.

One of the most difficult problems is preparation of the target nucleic acid prior to carrying out its amplification and detection. This process is time and labor intensive and, thus, generally unsuitable for a clinical setting, where rapid and accurate results are required. Another problem, especially for PCR and SDA, is that conditions for amplifying the target nucleic acid for subsequent detection and optional quantitation vary with each test, i.e., there are no constant conditions favoring test standardization. This latter problem is especially critical for the quantitation of a target nucleic acid by competitive PCR and for the simultaneous detection of multiple target nucleic acids.

Circumvention of the aforementioned problems would allow for development of rapid standardized assays, utilizing the various techniques mentioned above, that would be particularly useful in performing epidemiologic investigations, as well as in the clinical laboratory setting for detecting pathogenic microorganisms and viruses in a patient sample. Such microorganisms cause infectious diseases that represent a major threat to human health. The development of standardized and automated analytical techniques and kits therefor, based on rapid and sensitive identification of target nucleic acids specific for an infectious disease agent would provide advantages over techniques involving immunologic or culture detection of bacteria and viruses.

Reagents may be designed to be specific for a particular organism or for a range of related organisms. These reagents could be utilized to directly assay microbial genes conferring resistance to various antibiotics and virulence factors resulting in disease. Development of rapid standardized analytical techniques will aid in the selection of the proper treatment.

In some cases, assays having a moderate degree of sensitivity (but high specificity) may suffice, e.g., in initial screening tests. In other cases, great sensitivity (as well as specificity) is required, e.g., the detection of the HIV genome in infected blood may require finding the virus nucleic acid sequences present in a sample of one part per 10 to 100,000 human genome equivalents (Harper et al., Proc. Nat'l. Acad. Sci., USA 83:772, 1986).

Blood contaminants, including inter alia, HIV, HTLV-I, hepatitis B and hepatitis C, represent a serious threat to transfusion patients and the development of routine diagnostic tests involving the nucleic acids of these agents for the rapid and sensitive detection of such agents would be of great benefit in the clinical diagnostic agree laboratory. For example, the HIV genome can be detected in a blood sample using PCR techniques, either as an RNA molecule representing the free viral particle or as a DNA molecule representing the integrated provirus (Ou et al., Science 239:295, 1988; Murakawa et al., DNA 7:287, 1988).

In addition, epidemiologic investigations using classical culturing techniques have indicated that disseminated *Mycobacterium avium-intracellulaire* (MAI) infection is a complication of late-stage Acquired Immunodeficiency Syndrome (AIDS) in children and adults. The precise extent of the problem is not clear, however, since current cultural methods for detecting mycobacteria are cumbersome, slow and of questionable sensitivity. Thus, it would be desirable and highly beneficial to devise a rapid, sensitive and specific technique for MAI detection in order to provide a definitive picture of the involvement in HIV-infected and other immunosuppressed individuals. Such studies must involve molecular biological methodologies, based on detection of a target nucleic acid, which have routinely been shown to be more sensitive than standard culture systems (Boddinghaus et al., J. Clin. Med. 28: 1751, 1990).

Other applications for such techniques include detection and characterization of single gene genetic disorders in individuals and in populations (see, eg., Landergren et al. Science 241: 1077, 1988 which discloses a ligation technique for detecting single gene defects, including point mutations). Such techniques should be capable of clearly distinguishing single nucleotide differences (point mutations) that can result in disease (e.g., sickle cell anemia) as well as deleted or duplicated genetic sequences (e.g., thalassemia).

The methods referred to above are relatively complex procedures that, as noted, suffer from drawbacks making them difficult to use in the clinical diagnostic laboratory for routine diagnosis and epidemiological studies of infectious diseases and genetic abnormalities. All of the methods described involve amplification of the target nucleic acid to be detected. The extensive time and labor required for target nucleic acid preparation, as well as variability in amplification templates (e.g., the specific target nucleic acid whose detection is being measured) and conditions, render such procedures unsuitable for standardization and automation required in a clinical laboratory setting.

The present invention is directed to the development of rapid, sensitive assays useful for the detection and monitoring of pathogenic organisms, as well as the detection of abnormal genes in an individual. Moreover, the methodology of the present invention can be readily standardized and automated for use in the clinical laboratory setting.

SUMMARY OF THE INVENTION

An improved method, which allows for rapid, sensitive and standardized detection and quantitation of nucleic acids from pathogenic microorganisms from samples from patients with infectious diseases has now been developed. The improved methodology also allows for rapid and sensitive detection and quantitation of genetic variations in nucleic acids in samples from patients with genetic diseases or neoplasia.

This method provides several advantages over prior art methods. The method simplifies the target nucleic acid isolation procedure, which can be performed in microtubes, microchips or micro-well plates, if desired. The method allows for isolation, amplification and detection of nucleic acid sequences corresponding to the target nucleic acid of interest to be carried out in the same sample receptacle, e.g., tube or micro-well plate.

In another aspect of the invention, the techniques described herein may be used for detection of specific genes or markers at the single cell level using a gel matrix or slide format. In situ amplification and detection of nucleic acid sequences in single cells may be carried out using cells embedded in a semi-solid gel matrix. Such methods can be used to detect a mutation in a single cell, such as a tumor cell, or to detect chromosomal abnormalities in single cells such as embryo cells.

The method also allows for standardization of conditions, because only a pair of generic amplification probes may be utilized in the present method for detecting a variety of target nucleic acids, thus allowing efficient multiplex amplification. The method also allows the direct detection of RNA by probe amplification without the need for DNA template production. The amplification probes, which in the method may be covalently joined end to end, form a contiguous ligated amplification sequence. The assembly of the amplifiable DNA by ligation increases specificity, and makes possible the detection of a single mutation in a target. This ligated amplification sequence, rather than the target nucleic acid, is either directly detected or amplified, allowing for substantially the same amplification conditions to be used for a variety of different infectious agents and, thus, leading to more controlled and consistent results being obtained. In addition, multiple infectious agents in a single sample may be detected using the multiplex amplification methodology disclosed.

Additional advantages of the present invention include the ability to automate the protocol of the method disclosed, which is important in performing routine assays, especially in the clinical laboratory and the ability of the method to utilize various nucleic acid amplification systems, e.g., polymerase chain reaction (PCR), strand displacement amplification (SDA), ligase chain reaction (LCR) and self-sustained sequence replication (3SR).

The present method incorporates magnetic separation techniques using paramagnetic particles or beads coated with a ligand binding moiety that recognizes and binds to a ligand on an oligonucleotide capture probe to isolate a target nucleic acid (DNA or RNA) from a sample of a clinical specimen containing e.g., a suspected pathogenic microorganism or gene abnormality, in order to facilitate detection of the underlying disease-causing agent.

In one aspect of the present invention, a target nucleic acid is hybridized to a pair of non-overlapping oligonucleotide amplification probes in the presence of paramagnetic beads coated with a ligand binding moiety, e.g., streptavidin, to form a complex. These probes are referred to as a capture/amplification probe and an amplification probe, respectively. The capture/amplification probe contains a ligand, e.g., biotin, that is recognized by and binds to the ligand binding moiety on the paramagnetic beads. The probes are designed so that each contains generic sequences (i.e., not target nucleic acid specific) and specific sequences complementary to a nucleotide sequence in the target nucleic acid. The specific sequences of the probes are complementary to adjacent regions of the target nucleic acid, and thus do not overlap one another. Subsequently, the two probes are joined together using a ligating agent to form a contiguous ligated amplification sequence. The ligating agent may be an enzyme, e.g., DNA ligase or a chemical. Following washing and removal of unbound reactants and other materials in the sample, the detection of the target nucleic acid in the original sample is determined by detection of the ligated amplification sequence. The ligated amplification sequence may be directly detected if a sufficient amount (e.g., $10^6$-$19^7$ molecules) of target nucleic acid was present in the original sample. If an insufficient amount of target nucleic acid (<$10^6$ molecule) was present in the sample, the ligated amplification sequence (not the target nucleic acid) may be amplified using suitable amplification techniques, e.g., PCR, for detection. Alternatively, capture and amplification functions may be performed by separate and independent probes. For example, two amplification probes may be ligated to form a contiguous sequence to be amplified. Unligated probes, as well as the target nucleic acid, are not amplified in this technique. Yet another alternative is a single amplification probe that hybridizes to the target such that its 3' and 5' ends are juxtaposed. The ends are then ligated by DNA ligase to form a covalently linked circular probe that can be identified by amplification.

The present invention further provides methods for general amplification of total genomic DNA or mRNA expressed within a cell. The use of such methods provides a means for generating increased quantities of DNA and/or mRNA from small numbers of cells. Such amplified DNA and/or mRNA may then be used in techniques developed for detection of infectious agents, and detection of normal and abnormal genes.

In addition, the invention provides a novel differential display ligation dependent RAM method for identifying differentially expressed mRNAs within different types of cells.

Further, the invention provides methods wherein the capture/amplification probe can be designed to bind to an antibody. For example, one antibody can be attached to a capture/amplification probe and the other antibody can be attached to a target sequence. In this instance only if both antibodies are bound to the same antigen will ligation occur. This technique can be used for ELISA in a liquid phase RAM reaction or in situ in a solid phase RAM reaction.

BRIEF DESCRIPTION OF THE DRAWINGS

FIG. 1 is a generic schematic diagram showing the various components used in the present method of capture, ligation-dependent amplification and detection of a target nucleic acid.

FIG. 7 is a schematic diagram showing various components used to detect a target nucleic acid e.g., HCV RNA, employing two capture/amplification probes, each containing a bound biotin moiety, and a single amplification probe that circularizes upon hybridization to the target nucleic acid and ligation of free termini.

FIG. 12A depicts the prevention of primer extension due to the crosslinks in the method of reverse transcription PCR (RT-PCR).

FIG. 14 is a schematic diagram of HSAM using a circular target probe and three circular signal probes. AB, CD and EF indicate nucleotide sequences in the linker regions that are complementary to the 3' and 5' nucleotide sequences of a circular signal probe. AB', CD' and EF' indicate the 3' and 5' nucleotide sequences of the signal probes that have been juxtaposed by binding to the complementary sequences of the linker regions of another circular signal probe.

FIG. 15 is a schematic diagram of HSAM utilizing a circular target probe and linear signal probes.

DETAILED DESCRIPTION OF THE INVENTION

Figure 2:
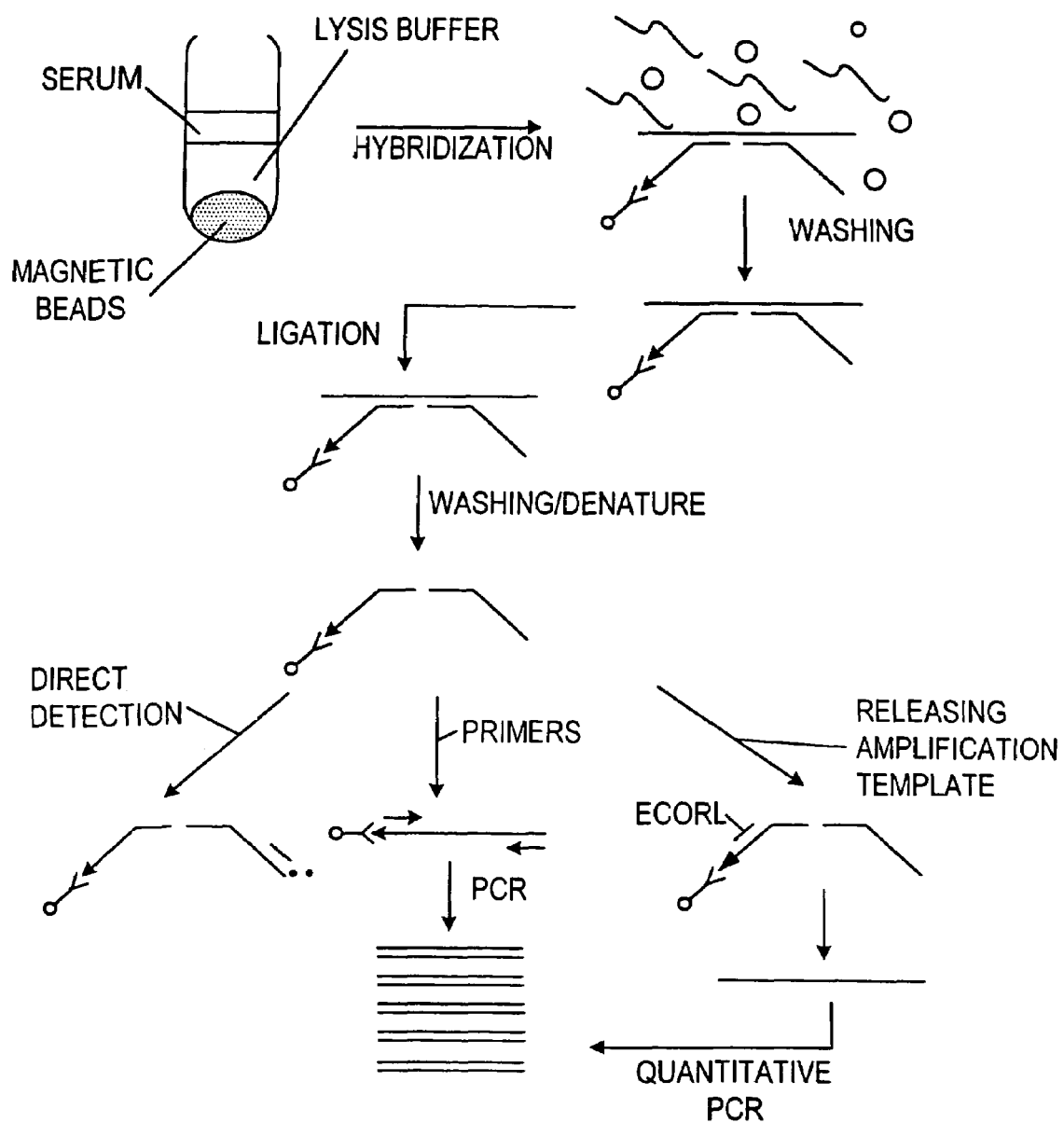
FIG. 2 is a schematic flow diagram generally showing the various steps in the present method.

The present invention is directed towards simplified sample preparation and generic amplification systems for use in clinical assays to detect and monitor pathogenic microorganisms in a test sample, as well as to detect abnormal genes in an individual. Generic amplification systems are described for clinical use that combine magnetic separation techniques with ligation/amplification techniques for detecting and measuring nucleic acids in a sample. The separation techniques may be combined with most amplification systems, including inter alia, PCR, LCR and SDA amplification techniques. The present invention further provides alternative amplification systems referred to as ramification-extension amplification method (RAM) and hybridization signal amplification (HSAM) that are useful in the method of the present invention. The advantages of the present invention include (1) suitability for clinical laboratory settings, (2) ability to obtain controlled and consistent (standardizable) results, (3) ability to quantitate nucleic acids in a particular sample, (4) ability to simultaneously detect and quantitate multiple target nucleic acids in a test sample, (5) ability to sensitively and efficiently detect nucleic acids in serum samples and in situ, and (6) ability to detect a single mutation in a target. Moreover, the complete protocol of the presently disclosed method may be easily automated, making it useful for routine diagnostic testing in a clinical laboratory setting. With the use of RAM and HSAM, an isothermal amplification can be achieved.

The present invention incorporates magnetic separation, utilizing paramagnetic particles, beads or spheres that have been coated with a ligand binding moiety that recognizes and binds to ligand present on an oligonucleotide capture probe, described below, to isolate a target nucleic acid (DNA or RNA) from a clinical sample in order to facilitate its detection.

Magnetic separation is a system that uses paramagnetic particles or beads coated with a ligand binding moiety to isolate a target nucleic acid (RNA or DNA) (Lomeli et al. Clin. Chem. 35:1826, 1989) from a sample. The principle underscoring this method is one of hybrid formation between a capture probe containing a ligand, and a target nucleic acid through the specific complementary sequence between the probe and target. Hybridization is carried out in the presence of a suitable chaotropic agent, e.g., guanidine thiocyanate (GnSCN) which facilitates the specific binding of the probe to complementary sequences in the target nucleic acid. The hybrid so formed is then captured on the paramagnetic bead through specific binding of the ligand on the capture probe to the ligand binding moiety on the bead.

The term "ligand" as used herein refers to any component that has an affinity for another component termed here as "ligand binding moiety." The binding of the ligand to the ligand binding moiety forms an affinity pair between the two components. For example, such affinity pairs include, inter alia, biotin with avidin/streptavidin, antigens or haptens with antibodies, heavy metal derivatives with thiogroups, various polynucleotides such as homopolynucleotides as poly dG with poly dC, poly dA with poly dT and poly dA with poly U. Any component pairs with strong affinity for each other can be used as the affinity pair, ligand-ligand binding moiety. Suitable affinity pairs are also found among ligands and conjugates used in immunological methods. The preferred ligand-ligand binding moiety for use in the present invention is the biotin/streptavidin affinity pair.

In one aspect, the present invention provides for the capture and detection of a target nucleic acid as depicted in FIG. 1, which provides a schematic depiction of the capture and detection of a target nucleic acid. In the presence of paramagnetic beads or particles (a) coated with a ligand binding moiety (b), the target nucleic acid is hybridized simultaneously to a pair of oligonucleotide amplification probes, i.e., a first nucleotide probe (also referred to as a capture/amplification probe) and a second nucleotide probe (also referred to as an amplification probe), designated in FIG. 1 as Capture/Amp-probe-1 (d and e) and Amp-probe-2 (f and g), respectively. The probes may be either oligodeoxyribonucleotide or oligoribonucleotide molecules, with the choice of molecule type depending on the subsequent amplification method. Reference to "probe" herein generally refers to multiple copies of a probe.

The capture/amplification probe is designed to have a generic 3' nucleotide sequence (d), i.e., it is not specific for the specific target nucleic acid being analyzed and thus can be used with a variety of target nucleic acids. In other words, the 3' sequence of the first probe is not complementary, nor hybridizable, to the nucleotide sequence of the target nucleic acid. The 5' portion (e) of the capture/amplification probe comprises a nucleotide sequence that is complementary and hybridizable to a portion of the nucleotide sequence of the specific target nucleic acid. Preferably, for use with pathogenic microorganisms and viruses, the capture/amplification probe is synthesized so that its 3' generic sequence (d) is the same for all systems, with the 5' specific sequence (e) being specifically complementary to a target nucleic acid of an individual species or subspecies of organism or an abnormal gene, e.g. the gene(s) responsible for cystic fibrosis or sickle cell anemia. In certain instances, it may be desirable that the 5' specific portion of the capture/amplification probe be specifically complementary to the nucleotide sequence of a target nucleic acid of a particular strain of organism. Capture/Amp-probe-1 further contains a ligand (c) at the 3' end of the probe (d), which is recognized by and binds to the ligand binding moiety (b) coated onto the paramagnetic beads (a).

The second or amplification probe, i.e., Amp-probe-2 in FIG. 1, contains a 3' sequence (f) that is complementary and hybridizes to a portion of the nucleotide sequence of a target nucleic acid immediately adjacent to (but not overlapping) the sequence of the target that hybridizes to the 5' end of Capture/Amp-probe-1. Amp-probe-2 also contains a 5' generic sequence (g) which is neither complementary nor hybridizable to the target nucleic acid, to which may be optionally attached at the 5' end thereof a label or signal generating moiety (***). Such signal generating moieties include, inter alia, radioisotopes, e.g., $^{32}P$ or $^{3}H$, fluorescent molecules, e.g., fluorescein and chromogenic molecules or enzymes, e.g., peroxidase. Such labels are used for direct detection of the target nucleic acid and detects the presence of Amp-probe-2 bound to the target nucleic acid during the detection step. $^{32}P$ is preferred for detection analysis by radioisotope counting or autoradiography of electrophoretic gels. Chromogenic agents are preferred for detection analysis, e.g., by an enzyme linked chromogenic assay.

As a result of the affinity of the ligand binding moiety on the paramagnetic beads for the ligand on the capture/amplification probe, target nucleic acid hybridized to the specific 5' portion of the probe is captured by the paramagnetic beads. In addition, Amp-probe-2, which has also hybridized to the target nucleic acid is also captured by the paramagnetic beads.

After capture of the target nucleic acid and the two hybridized probes on the paramagnetic beads, the probes are ligated together (at the site depicted by the vertical arrow in FIG. 1) using a ligating agent to form a contiguous single-stranded oligonucleotide molecule, referred to herein as a ligated amplification sequence. The ligating agent may be an enzyme, e.g., a DNA or RNA ligase, or a chemical joining agent, e.g., cyanogen bromide or a carbodiimide (Sokolova et al., FEBS Lett. 232:153-155, 1988). The ligated amplification sequence is hybridized to the target nucleic acid (either an RNA or DNA) at the region of the ligated amplification sequence that is complementary to the target nucleic acid (e.g., (e) and (f) in FIG. 1).

If a sufficient amount of target nucleic acid (e.g., $10^6$-$10^7$ molecules) is present in the sample, detection of the target nucleic acid can be achieved without any further amplification of the ligated amplification sequence, e.g., by detecting the presence of the optional signal generating moiety of at the 5' end of Amp-probe-2.

If there is insufficient target nucleic acid (e.g., $10^6$ molecules) in the sample for direct detection, as above, the ligated amplification sequence formed as described above by the ligation of Capture/Amp-probe-1 and Amp-probe-2 may be amplified for detection as described below.

Figure 28:
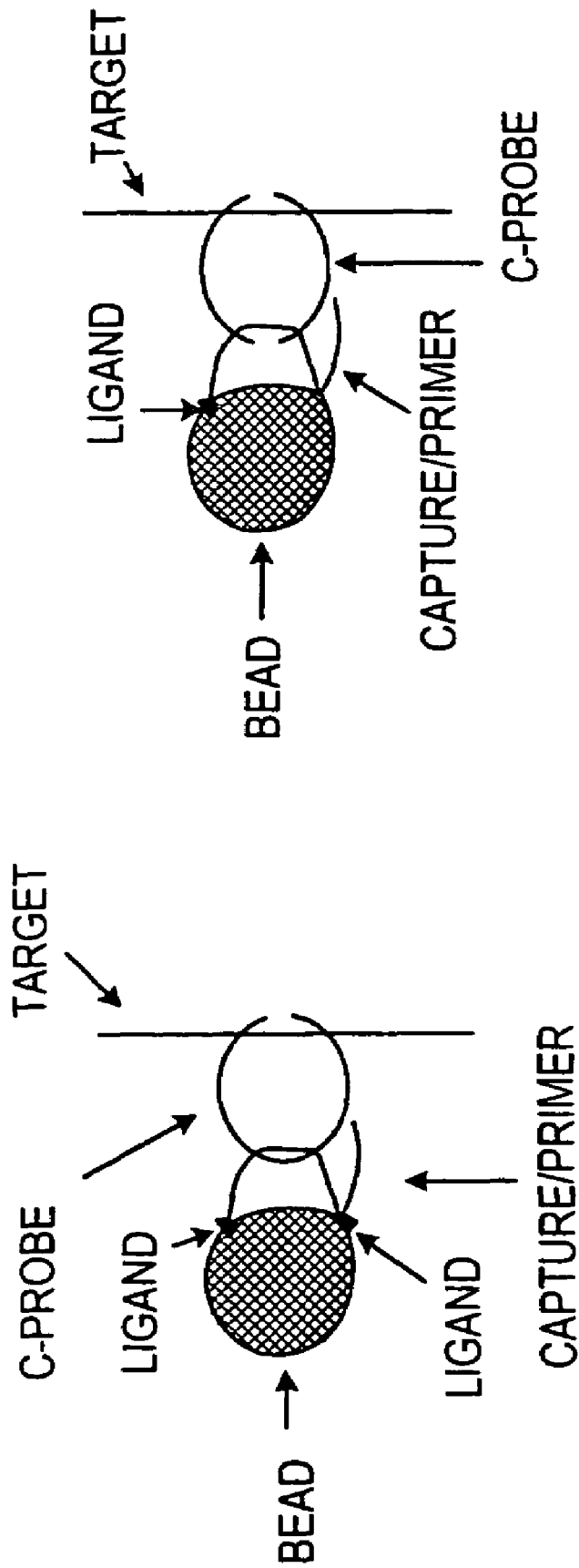
FIG. 28 depicts the capture of a target nucleic acid on a solid support utilizing a circular probe.

Alternatively, a capture/amplification probe, preferably between 70-90 nucleotides in length, can be synthesized to contain two ligand moieties: one located at the 5' end and the other located approximately 50 nucleotides downstream of the 5' end. A second circular probe, designated AMP-probe-2, is also synthesized. The linker region of the AMP-probe-2 is complementary to the capture/primer between nucleotide 1-50. In the assay system, the capture/amplification probe can bind to a ligand binding moiety conjugated to a support matrix, through a ligand/ligand binding interaction. Ligands include biotin, antigens, antibodies, heavy metal derivatives and polynucleotides. Ligand binding moieties include strepavidin, avidin, antibodies, antigens, thio groups, and polynucleotides. Support matrices include, for example magnetic beads although other types of supports may be used, including but not limited to, slides or microliter plates. The AMP-probe-2 will bind to the capture/amplification probe through the complementary region. The 3' end of the capture/amplification probe is designed to loop back and bind to 5' end of the linker region of the AMP-probe-2 and serves as a primer for extension. Finally, the target can bind to the AMP-probe-2 through complementary regions thereby permitting capture onto a matrix, such as magnetic beads for example, as depicted in FIG. 28. Ligation will join the 3' and the 5' end of the AMP-probe-2 and form a covalently linked circular probe. Bound probe allows for extensive stringent washes, thereby decreasing the background resulting from non-specific capturing. Extension from the capture/amplification probe along the C-probe will generate a multi-unit ssDNA which can then be amplified by either primer extension or RAM by addition of RAM primers as described above. To increase assay specificity even further, a double ligation can be performed, where two probes, each consisting of half of the AMP-probe-2, are used.

Figure 29:
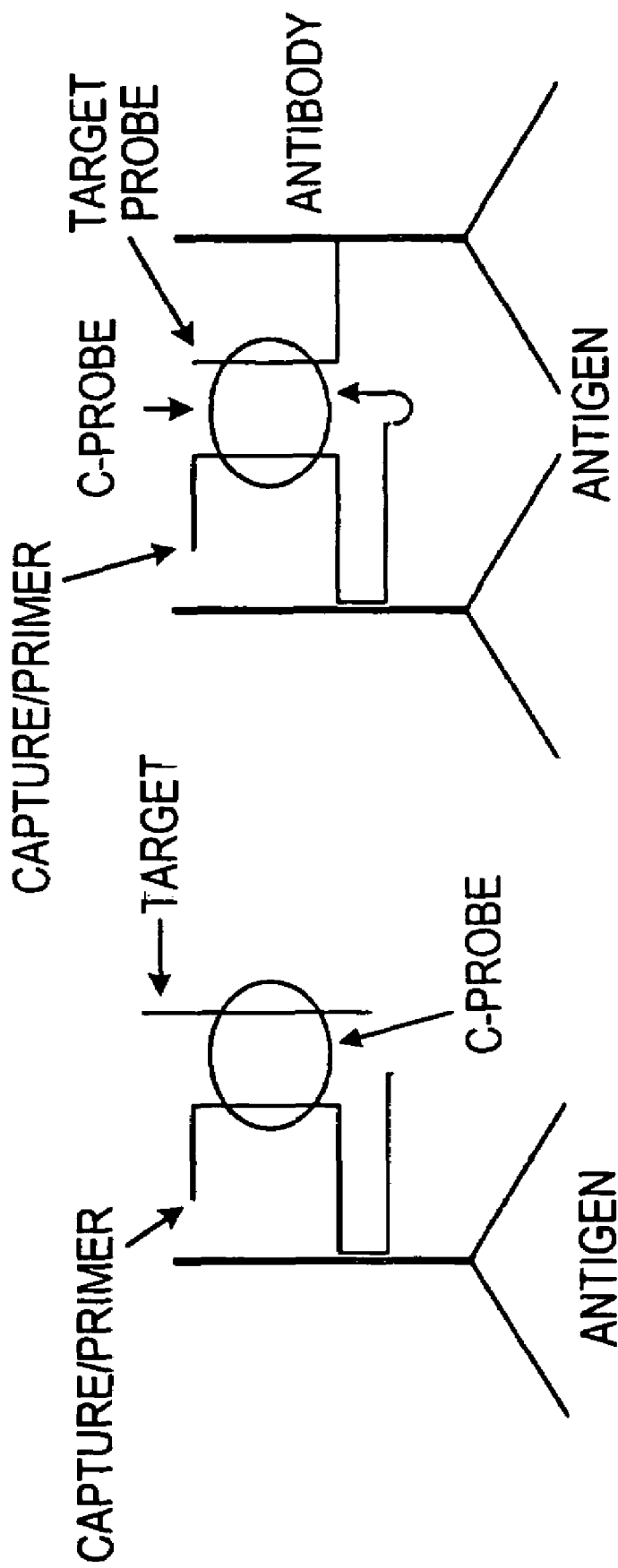
FIG. 29 is a diagram of the detection of an antibody or antigen using a capture/primer that specifically binds to the antibody or antigen.

In addition, the capture/amplification probe can be designed to bind to an antibody. The AMP-probe-2 as described above will target to the capture region of the capture/amplification probe (FIG. 29). After ligation, a primer extension or RAM reaction is carried out as described above. Alternatively, one antibody can be attached to a capture/amplification probe and the other antibody can be attached to a target sequence. In this instance only if both antibodies are bound to the same antigen will ligation occur. This technique can be used for ELISA in a liquid phase RAM reaction or in situ in a solid phase RAM reaction. For the detection purpose, FITC-labeled dUTP or dig-labeled dUTP can be used to detect the RAM products.

Figure 10:
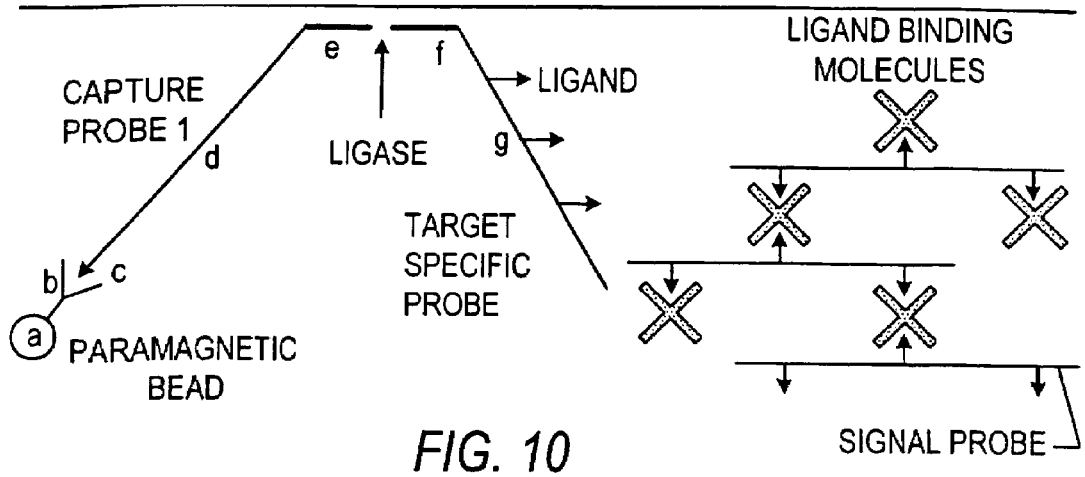
FIG. 10 is a schematic diagram illustrating the capture and detection of a target nucleic acid by the hybridization signal amplification method (HSAM).

Alternately, the ligated amplification sequence can be detected without nucleic acid amplification of the ligated sequence by the use of a hybridization signal amplification method (HSAM). HSAM is illustrated in FIG. 10. For HSAM, the target specific nucleic acid probe (e.g., Amp-probe-2) is internally labeled with a ligand. The ligand is a molecule that can be bound to the nucleic acid probe, and can provide a binding partner for a ligand binding molecule that is at least divalent. In a preferred embodiment the ligand is biotin or an antigen, for example digoxigenin. The nucleic acid probe can be labeled with the ligand by methods known in the art. In a preferred embodiment, the probe is labeled with from about 3 to about 10 molecules of ligand, preferably biotin or digoxigenin. After the capture probe and ligand-labeled target specific probe are added to the sample and the resulting complex is washed as described hereinabove, the ligating agent is added to ligate the probes as described above. The ligation of the target specific probe to the capture probe results in retention of the target specific probe on the beads. Concurrently or subsequently, an excess of ligand binding moiety is added to the reaction. The ligand binding moiety is a moiety that binds to and forms an affinity pair with the ligand. The ligand binding moiety is at least divalent for the ligand. In a preferred embodiment, the ligand is biotin and the ligand binding moiety is streptavidin. In another preferred embodiment the ligand is an antigen and the ligand binding molecule is an antibody to the antigen. Addition of ligating agent and ligand binding molecule results in a complex comprising the target specific probe covalently linked to the capture probe, with the ligand-labeled target specific probe having ligand binding molecules bound to the ligand.

A signal probe is then added to the reaction mixture. The signal probe is a generic nucleic acid that is internally labeled with a ligand that binds to the ligand binding molecule. In a preferred embodiment, the ligand is the same ligand that is used to label the target specific amplification probe. The signal probe has a generic sequence such that it is not complementary or hybridizable to the target nucleic acid or the other probes. In a preferred embodiment, the signal probe contains from about 30 to about 100 nucleotides and contains from about 3 to about 10 molecules of ligand.

Addition of the signal probe to the complex in the presence of excess ligand binding molecule results in the formation of a large and easily detectable complex. The size of the complex results from the multiple valency of the ligand binding molecule. For example, when the ligand in the target specific amplification probe is biotin, one molecule of streptavidin binds per molecule of biotin in the probe. The bound streptavidin is capable of binding to three additional molecules of biotin. When the signal probe is added, the biotin molecules on the signal probe bind to the available binding sites of the streptavidin bound to the amplification probe. A web-like complex is formed as depicted schematically in FIG. 10.

Following washing as described hereinabove to remove unbound signal probe and ligand binding molecules, the complex is then detected. Detection of the complex is indicative of the presence of the target nucleic acid. The HSAM method thus allows detection of the target nucleic acid in the absence of nucleic acid amplification.

The complex can be detected by methods known in the art and suitable for the selected ligand and ligand binding moiety. For example, when the ligand binding moiety is streptavidin, it can be detected by immunoassay with streptavidin antibodies. Alternately, the ligand binding molecule may be utilized in the present method as a conjugate that is easily detectable. For example, the ligand may be conjugated with a fluorochrome or with an enzyme that is detectable by an enzyme-linked chromogenic assay, such as alkaline phosphatase or horseradish peroxidase. For example, the ligand binding molecule may be alkaline phosphatase-conjugated streptavidin, which may be detected by addition of a chromogenic alkaline phosphatase substrate, e.g., nitroblue tetrazolium chloride.

The HSAM method may also be used with the circularizable amplification probes described hereinbelow. The circularizable amplification probes contain a 3' and a 5' region that are complementary and hybridizable to adjacent but not contiguous sequences in the target nucleic acid, and a linker region that is not complementary nor hybridizable to the target nucleic acid. Upon binding of the circularizable probe to the target nucleic acid, the 3' and 5' regions are juxtaposed. Linkage of the 3' and 5' regions by addition of a linking agent results in the formation of a closed circular molecule bound to the target nucleic acid. The target/probe complex is then washed extensively to remove unbound probes.

For HSAM, ligand molecules are incorporated into the linker region of the circularizable probe, for example during probe synthesis. The HSAM assay is then performed as described hereinabove and depicted in FIG. 15 by adding ligand binding molecules and signal probes to form a large complex, washing, and then detecting the complex. Nucleic acid detection methods are known to those of ordinary skill in the art and include, for example, latex agglutination as described by Essers, et al. (1980), J. Clin. Microbiol. 12:641. The use of circularizable probes in conjunction with HSAM is particularly useful for in situ hybridization.

Figure 11:
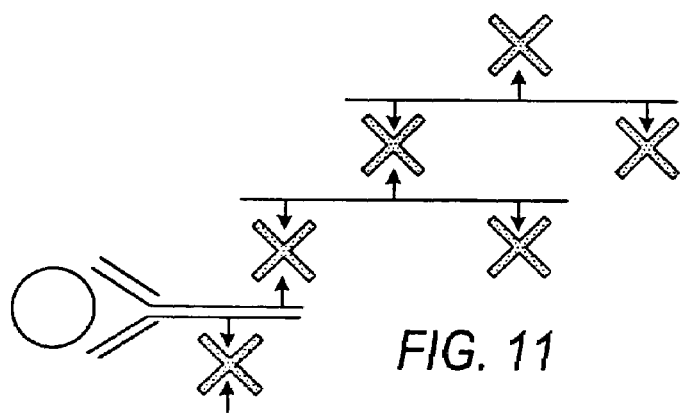
FIG. 11 is a schematic diagram illustrating the use of HSAM to detect an antigen with a biotinylated antibody and biotinylated signal probes.

HSAM is also useful for detection of an antibody or antigen. A ligand-containing antigen or antibody is used to bind to a corresponding antibody or antigen, respectively. After washing, excess ligand binding molecule is then added with ligand-labeled generic nucleic acid probe. A large complex is generated and can be detected as described hereinabove. In a preferred embodiment, the ligand is biotin and the ligand binding molecule is streptavidin. The use of HSAM to detect an antigen utilizing a biotinylated antibody and biotinylated signal probe is depicted in FIG. 11.

The present methods may be used with routine clinical samples obtained for testing purposes by a clinical diagnostic laboratory. Clinical samples that may be used in the present methods include, inter alia, whole blood, separated white blood cells, sputum, urine, tissue biopsies, throat swabbings and the like, i.e., any patient sample normally sent to a clinical laboratory for analysis.

Figure 12A:
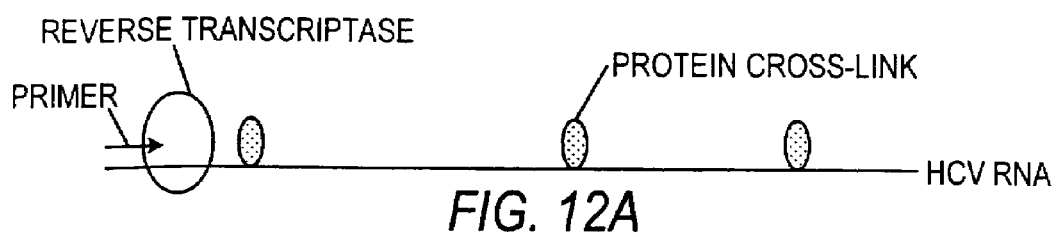
FIGS. 12A and B are schematic diagrams illustrating RNA-protein crosslinks formed during formalin fixation.
Figure 12B:
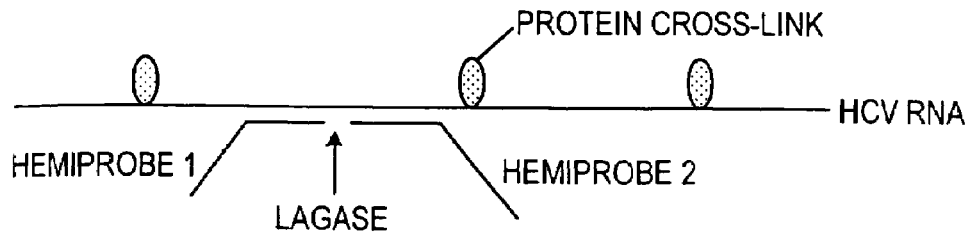
FIG. 12B illustrates that hybridization and ligation of the probes of the present invention are not prevented by protein-RNA crosslinks.

The present ligation-dependent amplification methods are particularly useful for detection of target sequences in formalin fixed, paraffin embedded (FFPE) specimens, and overcomes deficiencies of the prior art method of reverse transcription polymerase chain reaction (RT-PCR) for detection of target RNA sequences in FFPE specimens. RT-PCR has a variable detection sensitivity, presumably because the formation of RNA-RNA and RNA-protein crosslinks during formalin fixation prevents reverse transcriptase from extending the primers. In the present methods the probes can hybridize to the targets despite the crosslinks, reverse transcription is not required, and the probe, rather than the target sequence, is amplified. Thus the sensitivity of the present methods is not compromised by the presence of crosslinks. The advantages of the present methods relative to RT-PCR are depicted schematically in FIG. 12.

With reference to FIG. 2, which provides a general diagrammatic description of the magnetic separation and target-dependent detection of a target nucleic acid in a sample, this aspect of the present method involves the following steps:

(a) The first step is the capture or isolation of a target nucleic acid present in the sample being analyzed, e.g., serum. A suitable sample size for analysis that lends itself well to being performed in a micro-well plate is about 100 µl. The use of micro-well plates for analysis of samples by the present method facilitates automation of the method. The sample, containing a suspected pathogenic microorganism or virus or abnormal gene, is incubated with an equal volume of lysis buffer, containing a chaotropic agent (i.e., an agent that disrupts hydrogen bonds in a compound), a stabilizer and a detergent, which provides for the release of any nucleic acids and proteins that are present in the sample. For example, a suitable lysis buffer for use in the present method comprises 2.5-5M guanidine thiocyanate (GnSCN), 10% dextran sulfate, 100 mM EDTA, 200 mM Tris-HCl (pH 8.0) and 0.5% NP-40 (Nonidet P-40, a nonionic detergent, N-lauroylsarcosine, Sigma Chemical Co., St. Louis, Mo.). The concentration of GnSCN, which is a chaotropic agent, in the buffer also has the effect of denaturing proteins and other molecules involved in pathogenicity of the microorganism or virus. This aids in preventing the possibility of any accidental infection that may occur during subsequent manipulations of samples containing pathogens.

Paramagnetic particles or beads coated with the ligand binding moiety are added to the sample, either simultaneous with or prior to treatment with the lysis buffer. The paramagnetic beads or particles used in the present method comprise ferricoxide particles (generally <1 um in diameter) that possess highly convoluted surfaces coated with silicon hydrides. The ligand binding moiety is covalently linked to the silicon hydrides. The paramagnetic particles or beads are not magnetic themselves and do not aggregate together. However, when placed in a magnetic field, they are attracted to the magnetic source. Accordingly, the paramagnetic particles or beads, together with anything bound to them, may be separated from other components of a mixture by placing the reaction vessel in the presence of a strong magnetic field provided by a magnetic separation device. Such devices are commercially available, e.g., from Promega Corporation or Stratagene, Inc.

Suitable paramagnetic beads for use in the present method are those coated with streptavidin, which binds to biotin. Such beads are commercially available from several sources, e.g., Streptavidin MagneSphere® paramagnetic particles obtainable from Promega Corporation and Streptavidin-Magnetic Beads (catalog #MBOO2) obtainable from American Qualex, La Mirada, Calif.

Subsequently, a pair of oligonucleotide amplification probes, as described above, is added to the lysed sample and paramagnetic beads. In a variation, the probes and paramagnetic beads may be added at the same time. As described above, the two oligonucleotide probes are a first probe or capture/amplification probe (designated Capture/Amp-probe-1 in FIG. 1) containing a ligand at its 3' end and a second probe or amplification probe (designated Ampprobe-2 in FIG. 1). For use with streptavidin-coated paramagnetic beads, the first probe is preferably a 3'-biotinylated capture/amplification probe.

The probes may be synthesized from nucleoside triphosphates by known automated oligonucleotide synthetic techniques, e.g., via standard phosphoramidite technology utilizing a nucleic acid synthesizer. Such synthesizers are available, e.g., from Applied Biosystems, Inc. (Foster City, Calif.).

Each of the oligonucleotide probes are about 40-200 nucleotides in length, preferably about 50-100 nucleotides in length, which, after ligation of the probes, provides a ligated amplification sequence of about 80-400, preferably 100-200, nucleotides in length, which is suitable for amplification via PCR, Qβreplicase or SDA reactions.

The target nucleic acid specific portions of the probes, i.e., the 5' end of the first capture/amplification probe and the 3' end of the second amplification probe complementary to the nucleotide sequence of the target nucleic acid, are each approximately 15-60 nucleotides in length, preferably about 18-35 nucleotides, which provides a sufficient length for adequate hybridization of the probes to the target nucleic acid.

With regard to the generic portions of the probes, i.e., the 3' end of the capture/amplification probe and the 5' end of the amplification probe, which are not complementary to the target nucleic acid, the following considerations, inter alia, apply:

(1) The generic nucleotide sequence of an oligodeoxynucleotide capture/amplification probe comprises at least one and, preferably two to four, restriction endonuclease recognition sequences(s) of about six nucleotides in length, which can be utilized, if desired, to cleave the ligated amplification sequence from the paramagnetic beads by specific restriction endonucleases, as discussed below. Preferred restriction sites include, inter alia, EcoRI (GAATTC), SmaI (CCCGGG) and HindIII (AAGCTT).

(2) The generic nucleotide sequence comprises a G-C rich region which, upon hybridization to a primer, as discussed below, provides a more stable duplex molecule, e.g., one which requires a higher temperature to denature. Ligated amplification sequences having G-C rich generic portions of the capture/amplification and amplification probes may be amplified using a two temperature PCR reaction, wherein primer hybridization and extension may both be carried out at a temperature of about 60-65° C. (as opposed to hybridizing at 37° C., normally used for PCR amplification) and denaturation at a temperature of about 92° C., as discussed below. The use of a two temperature reaction reduces the length of each PCR amplification cycle and results in a shorter assay time.

Following incubation of the probes, magnetic beads and target nucleic acid in the lysis buffer for about 30-60 minutes, at a temperature of about 37° C., a ternary complex comprising the target nucleic acid and hybridized probes is formed, which is bound to the paramagnetic beads through the binding of the ligand (e.g., biotin) on the capture/amplification probe to the ligand binding moiety (e.g., streptavidin) on the paramagnetic beads. The method is carried out as follows:

(a) The complex comprising target nucleic acid-probes-beads is then separated from the lysis buffer by means of a magnetic field generated by a magnetic device, which attracts the beads. The magnetic field is used to hold the complex to the walls of the reaction vessel, e.g., a microwell plate or a microtube, thereby allowing for the lysis buffer and any unbound reactants to be removed, e.g., by decanting, without any appreciable loss of target nucleic acid or hybridized probes. The complex is then washed 2-3 times in the presence of the magnetic field with a buffer that contains a chaotropic agent and detergent in amounts that will not dissociate the complex. A suitable washing buffer for use in the present method comprises about 1.0-1.5M GnSCN, 10 mM EDTA, 100 mM Tris-HCl (pH 8.0) and 0.5% NP-40 (Nonidet P-40, nonionic detergent, Sigma Chemical Co., St. Louis, Mo.). Other nonionic detergents, e.g., Triton X-100, may also be used. The buffer wash removes unbound proteins, nucleic acids and probes that may interfere with subsequent steps. The washed complex may be then washed with a solution of KCl to remove the GnSCN and detergent and to preserve the complex. A suitable concentration of KCl is about 100 to 500 mM KCl. Alternatively, the KCl wash step may be omitted in favor of two washes with ligase buffer.

(b) If the probes are to be ligated together, the next step in the present method involves treating the complex from step (a) with a ligating agent that will join the two probes. The ligating agent may be an enzyme, e.g., DNA or RNA ligase, or a chemical agent, eg., cyanogen bromide or a carbodiimide. This serves to join the 5' end of the first oligonucleotide probe to the 3' end of the second oligonucleotide probe (capture/amplification probe and amplification probe, respectively) to form a contiguous functional single-stranded oligonucleotide molecule, referred to herein as a ligated amplification sequence. The presence of the ligated amplification sequence detected, (via the signal generating moiety at the 5'-end of Amp-probe-2), indirectly indicates the presence of target nucleic acid in the sample. Alternatively, the ligated amplification sequence serves as the template for any of various amplification systems, such as PCR or SDA. Any of the first and second probes which remain unligated after treatment are not amplified in subsequent steps in the method. Capture/amplification and amplification oligodeoxynucleotide probes may be ligated using a suitable ligating agent, such as a DNA or RNA ligase. Alternatively, the ligating agent may be a chemical, such as cyanogen bromide or a carbodiimide (Sokolova et al., FEBS Lett. 232:153-155, 1988). Preferred DNA ligases include $T_4$ DNA ligase and the thermostable Taq DNA ligase, with the latter being most preferable, for probes being subjected to amplification using PCR techniques. The advantage of using the Taq DNA ligase is that it is active at elevated temperatures (65-72° C.). Joining the oligonucleotide probes at such elevated temperatures decreases non-specific ligation. Preferably, the ligation step is carried out for 30-60 minutes at an elevated temperature (about 65-72° C.), after which time any unligated second amplification probe (Amp-probe-2 in FIG. 1) may be, optionally, removed under denaturing conditions.

Denaturation is performed after the ligation step by adding TE Buffer (10 mM Tris-HCl pH 7.5, 0.1 mM EDTA) to the mixture. The temperature of the mixture is then raised to about 92-95° C. for about 1-5 minutes to denature the hybridized nucleic acid. This treatment separates the target nucleic acid (and unligated Amp-probe-2) from the hybridized ligated amplification sequences, which remains bound to the paramagnetic beads. In the presence of a magnetic field, as above, the bound ligated amplification sequence is washed with TE Buffer at elevated temperature to remove denatured target nucleic acid and any unligated Amp-probe-2 and resuspended in TE Buffer for further analysis.

(c) The third step in the process is detection of the ligated amplification sequence, which indicates the presence of the target nucleic acid in the original test sample. This may be performed directly if sufficient target nucleic acid (about $10^6$-$10^7$ molecules) is present in the sample or following amplification of the ligated amplification sequence, using one of the various amplification techniques, e.g., PCR or SDA. For example, direct detection may be used to detect HIV-1 RNA in a serum sample from an acutely infected AIDS patient. Such a serum sample is believed to contain about $10^6$ copies of the viral RNA/ml.

For direct detection, an oligonucleotide detection probe of approximately 10-15 nucleotides in length, prepared by automative synthesis as described above to be complementary to the 5' end of the Amp-probe-2 portion of the ligated amplification sequence, may be added to the ligated amplification sequence attached to the paramagnetic beads. The detection probe, which is labeled with a signal generating moiety, e.g., a radioisotope, a chromogenic agent or a fluorescent agent, is incubated with the complex for a period of time and under conditions sufficient to allow the detection probe to hybridize to the ligated amplification sequence. The incubation time can range from about 1-60 minutes and may be carried out at a temperature of about 4-60° C. Preferably, when the label is a fluorogenic agent, the incubation temperature is about 4° C.; a chromogenic agent, about 37° C.; and a radioisotope, about 37°-60° C. Preferred signal generating moieties include, inter alia, $^{32}P$ (radioisotope), peroxidase (chromogenic) and fluorescein, acridine or ethidium (fluorescent).

Alternatively, for direct detection, as discussed above, the Amp-probe-2 itself may be optionally labeled at its 5' end with a signal generating moiety, e.g., $^{32}P$. The signal generating moiety will then be incorporated into the ligated amplification sequence following ligation of the Capture/Amp-probe-1 and Amp-probe-2. Thus, direct detection of the ligated amplification sequence, to indicate the presence of the target nucleic acid, can be carried out immediately following ligation and washing.

Any suitable technique for detecting the signal generating moiety directly on the ligated amplification probe or hybridized thereto via the detection primer may be utilized. Such techniques include scintillation counting (for $^{32}P$) and chromogenic or fluorogenic detection methods as known in the art. For example, suitable detection methods may be found, inter alia, in Sambrook et al., *Molecular Cloning—A Laboratory Manual*, 2d Edit., Cold Spring Harbor Laboratory, 1989, in *Methods in Enzymology*, Volume 152, Academic Press (1987) or Wu et al., *Recombinant DNA Methodology*, Academic Press (1989).

If an insufficient amount of target nucleic acid is present in the original sample (<$10^6$ molecules), an amplification system is used to amplify the ligated amplification sequence for detection.

For example, if the probes used in the present method are oligodeoxyribonucleotide molecules, PCR methodology can be employed to amplify the ligated amplification sequence, using known techniques (see, e.g., *PCR Technology*, H. A. Erlich, ed., Stockton Press, 1989, Sambrook et al., *Molecular Cloning—A Laboratory Manual*, 2d Edit., Cold Spring Harbor Laboratory, 1989. When using PCR for amplification, two primers are employed, the first of the primers being complementary to the generic 3' end of Capture/Amp-probe-1 region of the ligated amplification sequence and the second primer corresponding in sequence to the generic 5' end of Amp-probe-2 portion of the ligated amplification sequence. These primers, like the sequences of the probes to which they bind, are designed to be generic and may be used in all assays, irrespective of the sequence of the target nucleic acid. Because the first primer is designed to anneal to the generic sequence at the 3' end of the ligated amplification sequence and the second primer corresponds in sequence to the generic sequence at the 5' end of the ligated amplification sequence, generic primers maybe utilized to amplify any ligated amplification sequence.

Alternatively, multiple primers, designed to be complementary to the generic 3' end of the Capture/AMP- probe-1 region of the ligated amplification sequence and the generic 5' end of the AMP-probe-2 portion of the ligated amplification sequence may be used to amplify ligated amplification sequence together with the sequence between both ends. As demonstrated in the working examples described herein, increasing the number of primers was demonstrated to significantly increase the amplification efficiency thereby increasing the sensitivity of DNA detection.

A generic pair of PCR oligonucleotide primers for use in the present method may be synthesized from nucleoside triphosphates by known automated synthetic techniques, as discussed above for synthesis of the oligonucleotide probes. The primers may be 10-60 nucleotides in length. Preferably the oligonucleotide primers are about 18-35 nucleotides in length, with lengths of 12-21 nucleotides being most preferred. The pair of primers are designated to be complementary to the generic portions of the first capture/amplification probe and second amplification probe, respectively and thus have high G-C content. It is also preferred that the primers are designed so that they do not have any secondary structure, i.e., each primer contains no complementary region within itself that could lead to self annealing.

The high G-C content of the generic PCR primers and the generic portions of the ligated amplification sequence permits performing the PCR reaction at two temperatures, rather than the usual three temperature method. Generally, in the three temperature method, each cycle of amplification is carried out as follows:

Annealing of the primers to the ligated amplification sequence is carried out at about 37-50° C.; extension of the primer sequence by Taq polymerase in the presence of nucleoside triphosphates is carried out at about 70-75° C.; and the denaturing step to release the extended primer is carried out at about 90-95° C. In the two temperature PCR technique, the annealing and extension steps may both be carried at about 60-65° C., thus reducing the length of each amplification cycle and resulting in a shorter assay time.

For example, a suitable three temperature PCR amplification (as provided in Saiki et al., Science 239:487-491, 1988) may be carried out as follows:

Polymerase chain reactions (PCR) are carried out in about 25-50 µl samples containing 0.01 to 1.0 ng of template ligated amplification sequence, 10 to 100 pmol of each generic primer, 1.5 units of Taq DNA polymerase (Promega Corp.), 0.2 mM dATP, 0.2 mM dCTP, 0.2 mM dGTP, 0.2 mM dTTP, 15 mM MgCl2, 10 mM Tris-HCl (pH 9.0), 50 mM KCl, 1 µg/ml gelatin, and 10 µl/ml Triton X-100 (Saiki, 1988). Reactions are incubated at 94° C. for 1 minute, about 37 to 55° C. for 2 minutes (depending on the identity of the primers), and about 72° C. for 3 minutes and repeated for 30-40, preferably 35, cycles. A 4 µl-aliquot of each reaction is analyzed by electrophoresis through a 2% agarose gel and the DNA products in the sample are visualized by staining the gel with ethidium-bromide.

The two temperature PCR technique, as discussed above, differs from the above only in carrying out the annealing/extension steps at a single temperature, e.g., about 60-65° C. for about 5 minutes, rather than at two temperatures.

Also, with reference to FIG. 2, quantitative detection of the target nucleic acid using a competitive PCR assay may also be carried out. For such quantitative detection, a oligodeoxyribonucleotide releasing primer, synthesized generally as described above, is added to the paramagnetic bead-bound ligated amplification sequence. The releasing primer, may or may not be but, preferably, will be the same as the first PCR primer discussed above. The releasing primer is designed to hybridize to the generic 3' end of the Capture/Amp-probe-1 portion of the ligated amplification sequence, which, as discussed above, comprises a nucleotide sequence recognized by at least one, and preferably two-four, restriction endonucleases to form at least one, and preferably two-four, double-stranded restriction enzyme cleavage site, e.g., a EcoRI, SmaI and/or HindIII site(s).

In this regard, as noted above, for use in a quantitative PCR amplification and detection system, it is important that the Capture/Amp-probe-1 be synthesized with at least one, and preferably two to four nucleotide sequences recognized by a restriction enzyme located at the 3' end of the probe. This provides the nucleotide sequences to which the releasing primer binds to form double-stranded restriction enzyme cleavage site(s).

After ligating the first and second probes to form the ligated amplification sequence, the releasing primer is hybridized to the ligated amplification sequence. At least one restriction enzyme, e.g., EcoRI, SmaI and/or HindIII, is then added to the hybridized primer and ligated amplification sequence. The ligated amplification sequence is released from the beads by cleavage at the restriction enzyme, e.g., EcoRI site.

Following its release from the beads, the ligated amplification sequence is serially diluted and then quantitatively amplified via the DNA Taq polymerase using a suitable PCR amplification technique, as described above.

Quantitation of the original target nucleic acid in the sample may be performed by a competitive PCR method to quantitatively amplify the ligated amplification sequence, as provided, e.g., in Sambrook et al., *Molecular Cloning—A Laboratory Manual*, 2d Edit., Cold Spring Harbor Laboratory, 1989.

In general, the method involves co-amplification of two templates: the ligated amplification sequence and a control (e.g., the generic portions of the ligated amplification sequence or the generic portions that have interposed thereto a nucleotide sequence unrelated to the sequence of the target nucleic acid) added in known amounts to a series of amplification reactions. While the control and ligated amplification sequence are amplified by the same pair of generic PCR primers, the control template is distinguishable from the ligated amplification sequence, e.g., by being different in size. Because the control and ligated amplification sequence templates are present in the same amplification reaction and use the same primers, the effect of a number of variables which can effect the efficiency of the amplification reaction is essentially nullified. Such variables included, inter alia: (1) quality and concentration of reagents (Taq DNA polymerase, primers, templates, dNTP's), (2) conditions used for denaturation, annealing and primer extension, (3) rate of change of reaction temperature and (4) priming efficiency of the oligonucleotide primers. The relative amounts of the two amplified products—i.e., ligated amplification sequence and control template—reflect the relative concentrations of the starting templates.

The quantitative PCR method may be generally carried out as follows:

A control template, e.g., a DNA sequence corresponding to nanovariant RNA, a naturally occurring template of Qβreplicase (Schafiher et al., J. Mol. Biol. 117:877-907, 1977) is synthesized by automated oligonucleotide synthesis and its concentration determined, e.g., by spectrophotometry or by ethidium-bromide mediated fluorescence.

A series of tenfold dilutions (in TE Buffer) containing from 10 ng/ml to 1 fg/ml of the control template is made and stored at −70° C. until use.

A series of PCR amplification reactions of the free ligated amplification sequence is set up. In addition to the usual PCR ingredients, the reactions also contain about 10 μl/reaction of the tenfold dilutions of the control template and about 10 μCi/reaction of $[\alpha\text{-}^{32}P]$ dCTP(Sp.act. 3000 Ci/mmole).

PCR amplification reactions are carried out for a desired number of cycles, e.g., 30-40.

The reaction products may then be subject to agarose gel electrophoresis and autoradiography to separate the two amplified products (of different sizes). The amplified bands of the control and ligated amplification sequence are recovered from the gel using suitable techniques and radioactivity present in each band is determined by counting in a scintillation counter. The relative amounts of the two products are calculated based on the amount of radioactivity in each band. The amount of radioactivity in the two samples must be corrected for the differences in molecular weights of the two products.

The reactions may be repeated using a narrower range of concentration of control template to better estimate the concentration of ligated amplification sequence.

In another aspect of the invention, more than the two probes i.e. a single capture/amplification probe, and a single amplification probe may be utilized. For example one or more capture/amplification probes, and one or more amplification probes, may be employed in the detection and capture of the target nucleic acid, and optional amplification of the target sequences, as shown schematically in FIGS. 4 and 5. According to this aspect of the present invention, the capture/amplification probes may have a 3' sequence complementary to the target nucleic acid and a biotin moiety at the 5' terminus that is capable of interacting with the streptavidin coated paramagnetic beads. Alternatively, the capture/amplification probes may have a 5' sequence complementary to the target nucleic acid and a biotin moiety at the 3' terminus.

Further, according to this aspect of the present invention, one or more amplification probes are utilized such that each probe contains sequences that are specifically complementary to and hybridizable with the target nucleic acid. For example, the 5' end of one amplification probe, e.g. Amp-probe-2 (HCV A) in FIG. 4, contains a sequence complementary to a distinct portion in the target nucleic acid. The 3' end of the second amplification probe e.g. Amp-probe-2A (HCV A) in FIG. 4, contains a specific sequence complementary to a region of the target nucleic acid that is immediately adjacent to that portion of the target hybridizable to the first amplification probe. The capture/amplification probes and the pair of amplification probes hybridize with the target nucleic acid in the presence of GnSCN as described above. This complex so formed is bound to streptavidin-coated paramagnetic beads by means of a biotin moiety on the capture/amplification probes and the complex separated from unreacted components by means of magnetic separation as above. Next, the amplification probes may be linked, for example, by a ligase enzyme. This produces a ligated amplification sequence that serves as a template for Taq DNA polymerase during amplification reaction by PCR.

In a particular aspect of the invention, two or more capture/amplification probes and two pairs of amplification probes are utilized for the detection of the target nucleic acid.

The use of multiple capture/amplification probes affords even better capture efficiency, permitting the capture of multiple targets with generic capture probes. This is especially desirable for multiplex PCR reactions where multiple targets within a single reaction may be detected.

For example, a capture/amplification probe for use in the present method may be designed to bind to the poly-A tail region of cellular mRNA, whereby all such mRNA can be isolated by a single capture-and-wash step. Subsequent PCR amplification may be designed to detect and amplify specific target pathogen or disease gene sequences from such an mRNA pool. Such genes may include, inter alia, the gene encoding the cystic fibrosis transmembrane regulator protein (CFTR) or hemoglobins or other proteins involved in genetic diseases.

In still another aspect of the invention, the multiple capture/amplification probes may target, for example, all strains of a particular pathogen, e.g. the Hepatitis C Virus (HCV), and amplification probes may be tailored to detect and further identify individual HCV genotypes of the pathogen (e.g. HCV).

Figure 4:
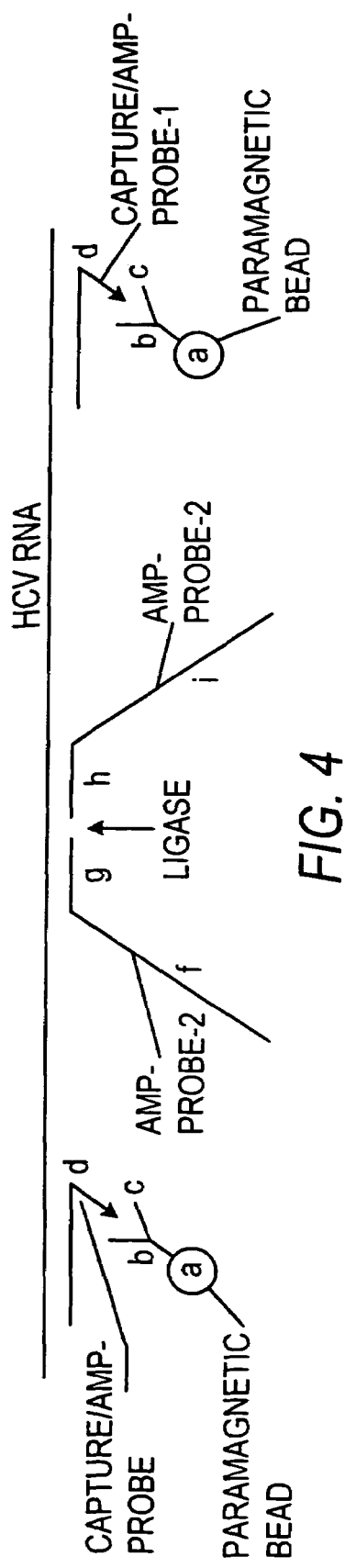
FIG. 4 is a schematic diagram of an embodiment of the present invention showing the various components used for capture and ligation-dependent detection of a target nucleic acid, e.g., HCV RNA, and subsequent amplification of its sequences, employing two capture/amplification probes containing a bound biotin moiety and two ligation-dependent amplification probes.
Figure 5:
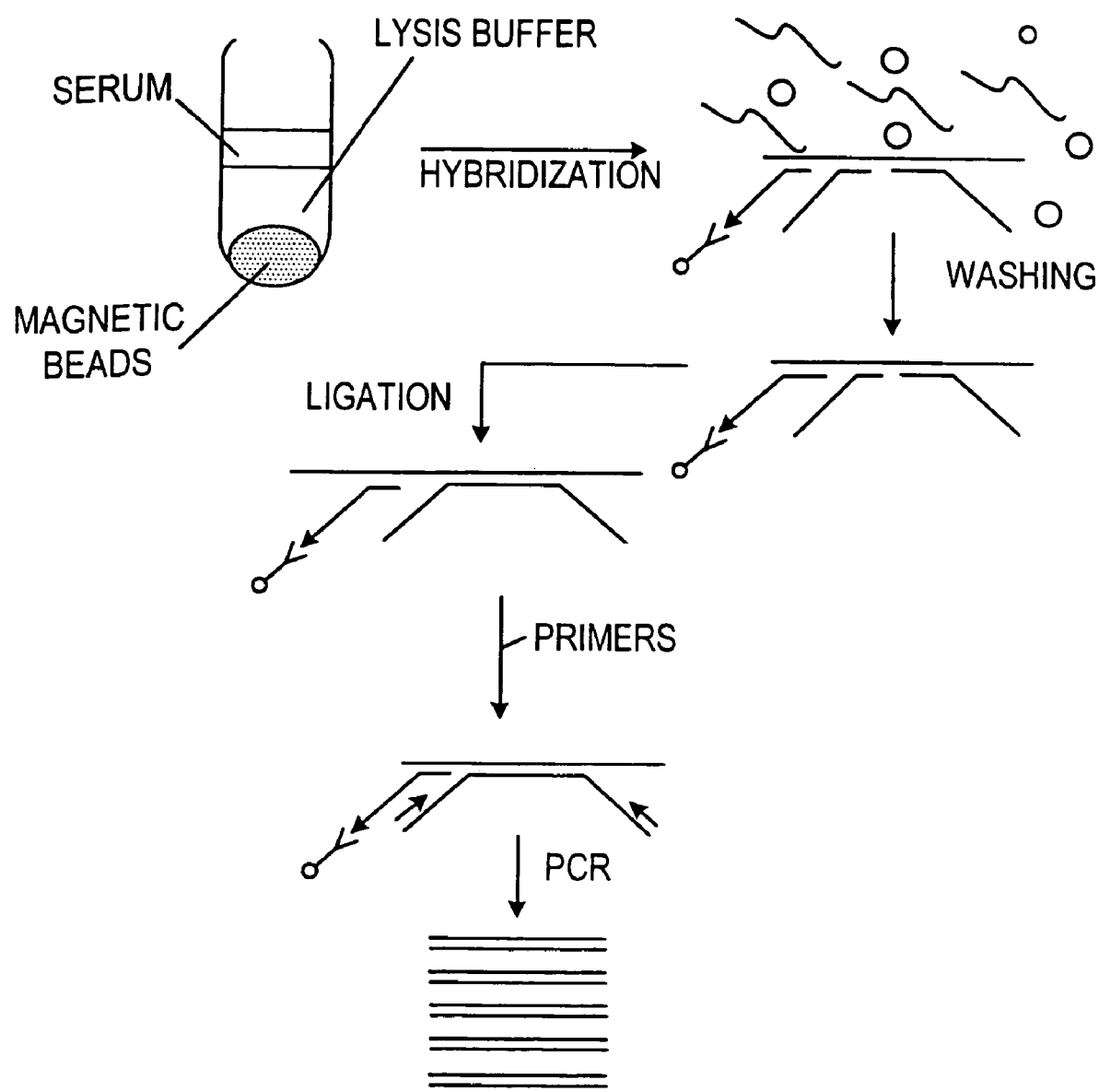
FIG. 5 is a schematic flow diagram showing magnetic isolation, target specific ligation and PCR amplification for the detection of HCV RNA using a single capture/amplification probe and two amplification probes.

In a further embodiment, two capture/amplification probes are utilized. e.g. as depicted in FIG. 4. This provides a total specific sequence of the capture/amplification probes complementary and hybridizable to the target nucleic acid that can be twice as long as that of a single capture/amplification probe, thereby affording an even higher capture efficiency.

The pair of capture/amplification probes, e.g. as shown in FIG. 4, may each have a 3' sequence complementary to the target nucleic acid, and a biotin moiety at its 5' terminus capable of interacting with streptavidin coated paramagnetic beads. Alternatively, the pair of capture/amplification probes may each have a 5' sequence complementary to the target nucleic acid, and a biotin moiety at its 3' terminus capable of interacting with streptavidin coated paramagnetic beads.

Figure 13:
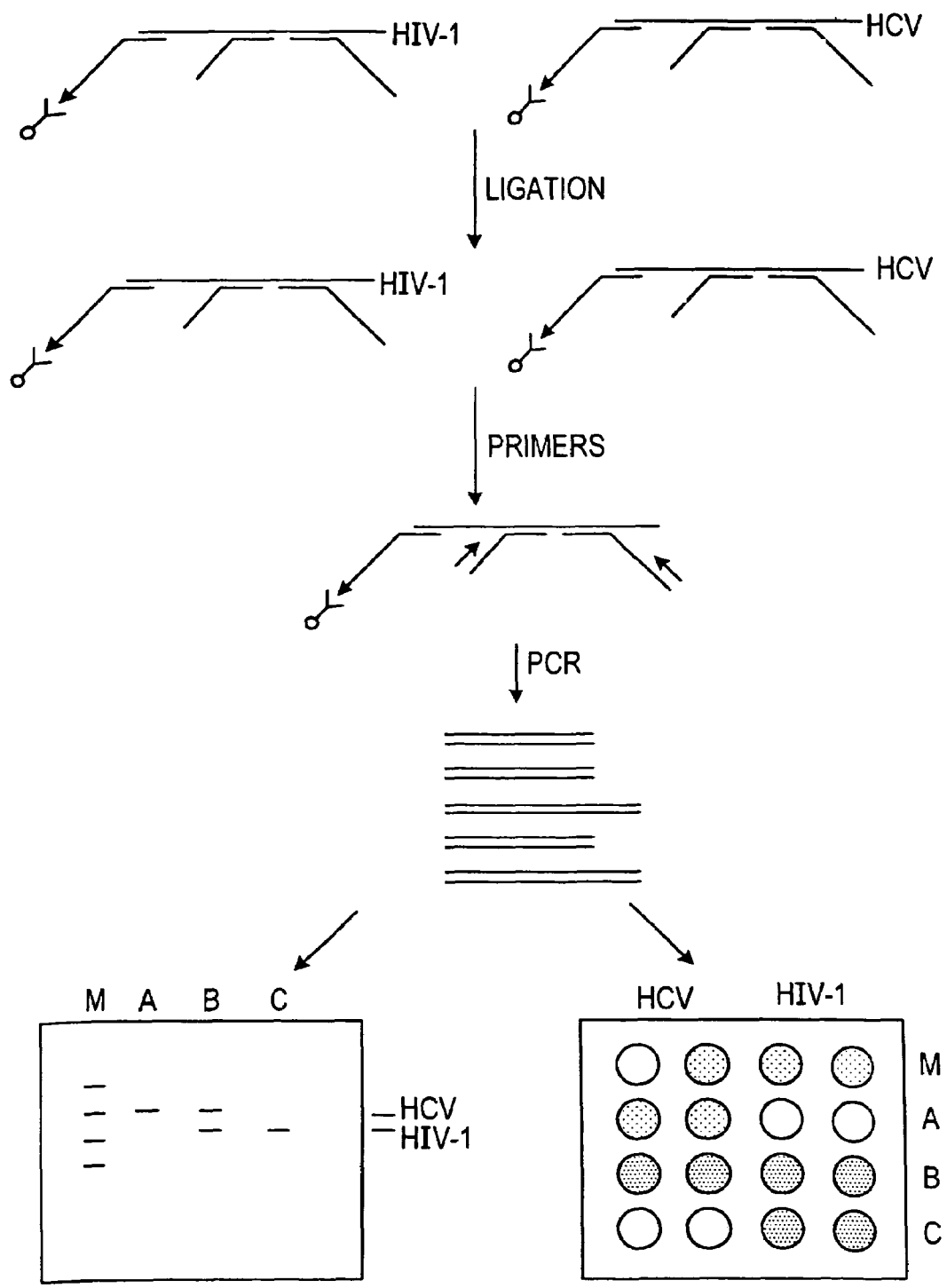
FIG. 13 is a schematic diagram of multiplex PCR. Two set of capture/amplification probes, having specificity for HIV-1 and HCV, respectively, are used for target capture, but only one pair of generic PCR primers is used to amplify the ligated probes. The presence of each target can be determined by the size of the amplified product or by enzyme-linked immunosorbent assay.

Further, the present method in which the ligated target probe is amplified by PCR permits the detection of multiple targets in a single reaction, as illustrated in FIG. 13 and designated as multiplex LD-PCR. In the prior art methods of PCR amplification of a target nucleic acid, attempts to detect multiple targets with multiple primer pairs in a single reaction vessel have been limited by varying primer efficiencies and competition among primer pairs. In contrast, in the present method each capture/amplification probe has a target specific region and a generic region. In multiplex LD-PCR according to the present invention, the generic regions to which the PCR primers bind may be common to all capture/amplification probes. Thus multiple pairs of capture/amplification probes having specificity for multiple targets may be used, but only one pair of generic PCR primers are needed to amplify the ligated capture/amplification probes. By varying the length of the target specific regions of the capture/amplification probes, amplified PCR products corresponding to a particular target can be identified by size.

The PCR products may also be identified by an enzyme-linked immunosorbent assay (ELISA). The PCR product may be labeled during amplification with an antigen, for example digoxigenin. The labeled PCR product is then captured on a microtiter plate having thereon a nucleic acid probe that hydridizes to the target specific region of the amplification probe, which region is present in the amplified product. The labeled captured product may then be detected by adding an enzyme conjugated antibody against the antigen label, for example horseradish peroxidase anti-digoxigenin antibody, and a color indicator to each well of the microtiter plate. The optical density of each well provides a measure of the amount of PCR product, which in turn indicates the presence of the target nucleic acid in the original sample.

Figure 6:
FIG. 6 is a schematic diagram showing the various components used to amplify and detect a target nucleic acid e.g., HCV RNA, employing two capture/amplification probes, each containing a bound biotin moiety, and a single amplification probe.

In still further embodiments, the present invention may utilize a single amplifiable "full length probe" and one or more capture/amplification probes as shown in FIG. 6. Further, the hybridized nucleic acid duplex, comprising of the target nucleic acid, for example, HCV RNA, and the capture/amplification probes and full length amplification probes, also referred to as amplification sequences, can be released from the magnetic beads by treating the hybridized duplex molecule with RNAase H. Alternatively, the hybridized duplex, comprising of the target nucleic acid, e.g. DNA, and the capture/amplification probes and full length amplification probes, can be released from the magnetic beads by treating the hybridized duplex molecule with appropriate restriction enzymes, as described above.

When a full length amplification probe is employed to detect a target nucleic acid sequence, the probe may be utilized in amplification reactions such as PCR, without having to use the ligation step described above. This latter approach, in particular, simplifies the assay and is especially useful when at least $10^4$ target nucleic acid molecules are available in the testing sample, so that the chances of non-specific binding in a ligation independent detection reaction are reduced. In most clinical detection assays, the target nucleic acid (such as a pathogen), is present at $>10^5$ molecules/ml. of sample, and thus would be amenable to detection and amplification by this method.

A still further aspect of the present invention utilizes one or more capture/amplification probes, each containing a biotin moiety, and a single amplification probe, also referred to as an amplification sequence, that hybridizes to the target nucleic acid and circularizes upon ligation of its free termini, as shown in FIG. 7. The amplification probe may be designed so that complementary regions (see e.g. the region shown in bold in FIG. 7) of the probe that are hybridizable to the target nucleic acid sequence are located at each end of the probe (as described in Nilsson et al., 1994, Science 265:2085-2088). When the probe hybridizes with the target, its termini are placed adjacent to each other, resulting in the formation of a closed circular molecule upon ligation with a linking agent such as a ligase enzyme. This circular molecule may then serve as a template during an amplification step, e.g. PCR, using primers such as those depicted in FIG. 7. The circular molecule may also be amplified by RAM, as described hereinbelow, or detected by a modified HSAM assay, as described hereinbelow.

For example, the probe, described above, can be used to detect different genotypes of a pathogen, e.g. different genotypes of HCV from serum specimens. Genotype specific probes can be designed, based on published HCV sequences (Stuyver et al., 1993, J. Gen. Virol. 74: 1093-1102), such that a mutation in the target nucleic acid is detectable since such a mutation would interfere with (1) proper hybridization of the probe to the target nucleic acid and (2) subsequent ligation of the probe into a circular molecule. Because of the nature of the circularized probe, as discussed below, unligated probes may be removed under stringent washing conditions.

The single, full length, ligation-dependent circularizable probe, as utilized in the method, affords greater efficiency of the detection and amplification of the target nucleic acid sequence. Due to the helical nature of double-stranded nucleic acid molecules, circularized probes are wound around the target nucleic acid strand. As a result of the ligation step, the probe may be covalently bound to the target molecule by means of catenation. This results in immobilization of the probe on the target molecule, forming a hybrid molecule that is substantially resistant to stringent washing conditions. This results in significant reduction of non-specific signals during the assay, lower background noise and an increase in the specificity of the assay.

Another embodiment of the present invention provides a method of reducing carryover contamination and background in amplification methods utilizing circular probes. The present ligation-dependent amplification methods, unlike conventional amplification methods, involve amplification of the ligated probe(s) rather than the target nucleic acid. When the ligated probe is a closed circular molecule, it has no free ends susceptible to exonuclease digestion. After probe ligation, i.e. circularization, treatment of the reaction mixture with an exonuclease provides a "cleanup" step and thus reduces background and carryover contamination by digesting unligated probes or linear DNA fragments but not closed circular molecules. The covalently linked circular molecules remain intact for subsequent amplification and detection. In conventional PCR, the use of exonuclease to eliminate single stranded primers or carry-over DNA fragments poses the risk that target nucleic acid will also be degraded.

The present invention does not suffer this risk because target nucleic acid is not amplified. In a preferred embodiment, the exonuclease is exonuclease III, exonuclease VII, mung bean nuclease or nuclease BAL-31. Exonuclease is added to the reaction after ligation and prior to amplification, and incubated, for example at 37° C. for thirty minutes.

It is further contemplated to use multiple probes which can be ligated to form a single covalently closed circular probe. For example, a first probe is selected to hybridize to a region of the target. A second probe is selected such that its 3' and 5' termini hybridize to regions of the target that are adjacent but not contiguous with the 5' and 3' termini of the first probe. Two ligation events are then required to provide a covalently closed circular probe. By using two ligases, e.g. an enzymatic and a chemical ligase, to covalently close the probe, the order of the ligations can be controlled. This embodiment is particularly useful to identify two nearby mutations in a single target.

Figure 9:
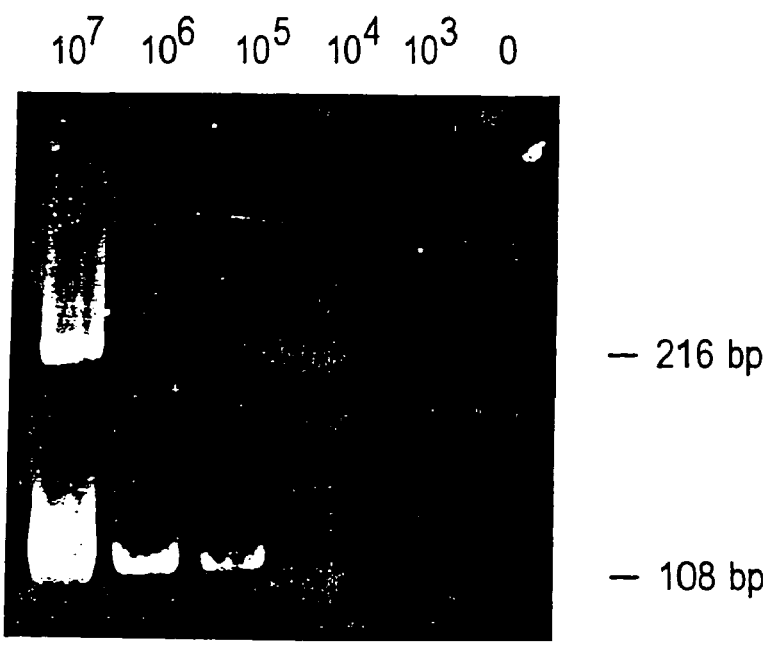
FIG. 9 is a photograph of ethidium bromide stained DNA depicting PCR amplified single, full length ligation-dependent and circularizable probes used to detect HCV RNA in a sample. The amount of HCV RNA in the sample is determined by comparing sample band densities to those of standard serial dilutions of HCV transcripts.
Figure 16:
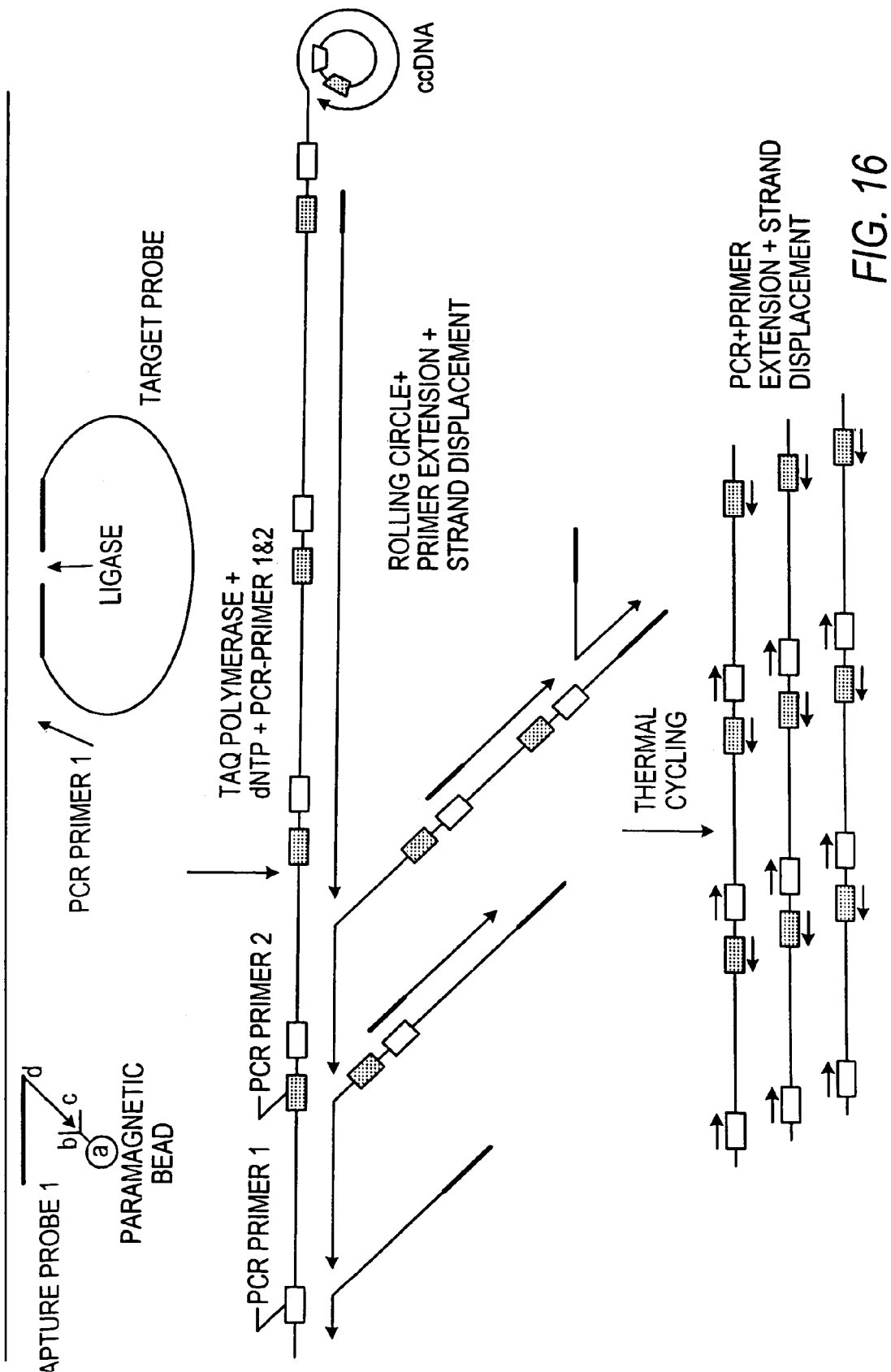
FIG. 16 is a schematic diagram of amplification of a circularized probe by primer-extension/displacement and PCR.

The circularized probe can also be amplified and detected by the generation of a large polymer. The polymer is generated through the rolling circle extension of primer 1 along the circularized probe and displacement of downstream sequence. This step produces a single stranded DNA containing multiple units which serves as a template for subsequent PCR, as depicted in FIGS. 9 and 16. As shown therein, primer 2 can bind to the single stranded DNA polymer and extend simultaneously, resulting in displacement of downstream primers by upstream primers. By using both primer-extension/displacement and PCR, more detectable product is produced with the same number of cycles.

The circularized probe may also be detected by a modification of the HSAM assay. In this method, depicted in FIG. 14, the circularizable amplification probe contains, as described hereinabove, 3'- and 5' regions that are complementary to adjacent regions of the target nucleic acid. The circularizable probes further contain a non-complementary, or generic linker region. In the present signal amplification method, the linker region of the circularizable probe contains at least one pair of adjacent regions that are complementary to the 3' and 5' regions of a first generic circularizable signal probe (CS-probe). The first CS-probe contains, in its 3' and 5' regions, sequences that are complementary to the adjacent regions of the linker region of the circularizable amplification probe. Binding of the circularizable amplification probe to the target nucleic acid, followed by ligation, results in a covalently linked circular probe having a region in the linker available for binding to the 3' and 5' ends of a first CS-probe. The addition of the first CS-probe results in binding of its 3' and 5' regions to the complementary regions of the linker of the circular amplification probe. The 3' and 5' regions of the CS-probe are joined by the ligating agent to form a closed circular CS-probe bound to the closed circular amplification probe. The first CS-probe further contains a linker region containing at least one pair of adjacent contiguous regions designed to be complementary to the 3' and 5' regions of a second CS-probe.

The second CS-probe contains, in its 3' and 5' regions, sequences that are complementary to the adjacent regions of the linker region of the first CS-probe. The addition of the second CS-probe results in binding of its 3' and 5' regions to the complementary regions of the linker of the first CS-probe. The 3' and 5' regions of the second CS-probe are joined by the ligating agent to form a closed circular CS-probe, which is in turn bound to the closed circular amplification probe.

By performing the above-described method with a multiplicity of CS-probes having multiple pairs of complementary regions, a large cluster of chained molecules is formed on the target nucleic acid. In a preferred embodiment, three CS-probes are utilized. In addition to the 3' and 5' regions, each of the CS-probes has one pair of complementary regions that are complementary to the 3' and 5' regions of a second CS-probe, and another pair of complementary regions that are complementary to the 3' and 5' regions of the third CS-probe. By utilizing these "trivalent" CS-probes in the method of the invention, a cluster of chained molecules as depicted in FIG. 14 is produced.

Following extensive washing to remove non-specific chain reactions that are unlinked to the target, the target nucleic acid is then detected by detecting the cluster of chained molecules. The chained molecules can be easily detected by digesting the complex with a restriction endonuclease for which the recognition sequence has been uniquely incorporated into the linker region of each CS-probe. Restriction endonuclease digestion results in a linearized monomer that can be visualized on a polyacrylamide gel. Other methods of detection can be effected by incorporating a detectable molecule into the CS-probe, for example digoxigenin, biotin, or a fluorescent molecule, and detecting with anti-digoxinin, streptavidin, or fluorescence detection. Latex agglutination, as described for example by Essers et al. (1980) *J. Clin. Microbiol.* 12, 641, may also be used. Such nucleic acid detection methods are known to one of ordinary skill in the art.

Moreover, in a special application, the amplification probes and/or amplification sequences as described above, can be used for in situ LD-PCR assays. In situ PCR may be utilized for the direct localization and visualization of target viral nucleic acids and may be further useful in correlating viral infection with histopathological finding.

Current methods assaying for target viral RNA sequences have utilized RT PCR techniques for this purpose (Nuovo et al., 1993, Am. J. Surg. Pathol. 17(7):683-690). In this method cDNA, obtained from target viral RNA by in situ reverse transcription, is amplified by the PCR method.

Subsequent intracellular localization of the amplified cDNA can be accomplished by in situ hybridization of the amplified cDNA with a labeled probe or by the incorporation of labeled nucleotide into the DNA during the amplification reaction.

However, the RT PCR method suffers drawbacks which are overcome by the present invention. For example, various tissue fixatives used to treat sample tissues effect the crosslinking of cellular nucleic acids and proteins, e.g. protein-RNA and RNA-RNA complexes and hinder reverse transcription, a key step in RT-PCR. Moreover, secondary structures in target RNA may also interfere with reverse transcription. Further, the application of multiplex PCR to RT PCR for the detection of multiple target sequences in a single cell can present significant problems due to the different efficiencies of each primer pair.

The method of the present invention utilizes one or more amplification probes and/or amplification sequences, as described above, and the LD-PCR technique to locate and detect in situ target nucleic acid, which offers certain advantages over the RT-PCR method. First, since hybridization of the probe to target nucleic acid and subsequent amplification of the probe sequences eliminates the reverse transcription step of the RT-PCR method, the secondary structure of the target RNA does not affect the outcome of the assay. Moreover, the crosslinking of target nucleic acids and cellular proteins due to tissue fixatives, as discussed above, does not interfere with the amplification of probe sequences since there is no primer extension of the target RNA as in the RT-PCR method.

In particular, amplification probes according to the present invention may be designed such that there are common primer-binding sequences within probes detecting different genotypic variants of a target pathogen. This enables the assay to detect multiple targets in a single sample. For example, and not by way of limitation, the assay may utilize two or more amplification probes according to this method to detect HCV RNA and β-actin RNA, whereby the β-actin probe serves as an internal control for the assay.

Furthermore, the primer-binding sequences in the probe may be designed to (1) minimize non-specific primer oligomerization and (2) achieve superior primer-binding and increased yield of PCR products, thereby increasing sensitivity of the assay.

Since the amplification probe circularizes after binding to target nucleic acid to become a circular molecule, multimeric products may be generated during polymerization, so that amplification products are easily detectable, as described above, as shown in FIGS. 9 and 16.

An in situ LD-PCR assay to detect target nucleic acids in histological specimens according to the present invention utilizes a ligation dependent full length amplification probe, and involves the following steps:

Sample tissue, e.g. liver, that may be frozen, or formalin-fixed and embedded in paraffin, is sectioned and placed on silane-coated slides. The sections may be washed with xylene and ethanol to remove the paraffin. The sections may then be treated with a proteolytic enzyme, such as trypsin, to increase membrane permeability. The sections may be further treated with RNAase-free DNAase to eliminate cellular DNA.

An amplification probe may be suspended in a suitable buffer and added to the sample sections on the slide and allowed to hybridize with the target sequences. Preferably, the probe may dissolved in 2×SSC with 20% formamide, added to the slide, and the mixture incubated for 2 hours at 37° C. for hybridization to occur. The slide may be washed once with 2×SSC and twice with 1× ligase buffer before DNA ligase may be applied to the sample. Preferably, 1U/20 μl of the ligase enzyme may be added to each slide, and the mixture incubated at 37° C. for 2 hours to allow circularization of the probe. The slide may be washed with 0.2×SSC (high stringency buffer) and 1×PCR buffer to remove unligated probes before the next step of amplification by PCR. The PCR reaction mixture, containing the amplification primers and one or more labeled nucleotides is now added to the sample on the slide for the amplification of the target sequences. The label on the nucleotide(s) may be any signal generating moiety, including, inter alia, radioisotopes, e.g., $^{32}P$ or $^{3}H$, fluorescent molecules, e.g., fluorescein and chromogenic molecules or enzymes, e.g., peroxidase, as described earlier. Chromogenic agents are preferred for detection analysis, e.g., by an enzyme linked chromogenic assay.

In a still preferred aspect, digoxinin-labeled nucleotides are utilized. In such cases the PCR product, tagged with digoxinin-labeled nucleotides is detectable when incubated with an antidigoxinin antibody-alkaline phosphatase conjugate. The alkaline phosphatase-based calorimetric detection utilizes nitroblue tetrazolium, which, in the presence of 5-Bromo-4-chloro-3-indolylphosphate, yields a purple-blue precipitate at the amplification site of the probe.

In one aspect of the present invention, the ligation and the PCR amplification step of the in situ LD-PCR detection method can be carried out simultaneously and at a higher temperature, by using a thermostable ligase enzyme to circularize the amplification probe.

In accordance with the present invention, further embodiments of in situ LD-PCR may utilize amplification probes that are designed to detect various genotypic variants of a pathogen e.g. HCV, that are based on the known HCV sequences of these variants (Stuyver et al., 1993, J. Gen. Vir. 74:1093-1102). For example, different type-specific probes may be added together to the sample, and detection of HCV sequences and amplification of the probe sequences carried out by in situ LD-PCR as described above. Next, the amplified probe sequences are assayed for the presence of individual variant genotypes by in situ hybridization with type specific internal probes that are labeled to facilitate detection.

In certain aspects of the invention, the target nucleic acid sequence may be directly detected using the various amplification probes and/or amplification sequences described above, without amplification of these sequences. In such aspects, the amplification probes and/or amplification sequences may be labeled so that they are detectable.

In an embodiment of the invention the RAM amplification method described herein may be used in a gel matrix format or slide format combined with fluorescent primers to detect aneusomy or gene mutation in situ in a single cell. Embedding single cells in a gel matrix allows for enzymatic manipulation of the cell, i.e., proteinase digestion to release DNA, without the lose of genomic material. The gel matrix also protects the DNA from shearing damage and allows for maintenance of the cell's original three dimensional configuration.

In yet another embodiment of the invention, a method is provided wherein nucleic acid molecules or proteins are embedded within a matrix for in situ detection of target molecules. The method of the invention provides a means for maintaining the signal in a particular location and may be used in DNA and protein array technology in conjunction with the amplification methods described herein, i.e., RAM and HSAM.

In a specific embodiment of the invention, a ligand moiety is linked to a gel matrix material. Such linkage may be provided by interactions between the ligand moiety and chemical groups or proteins within the matrix. C-probe linked to a ligand binding moiety is then added to the gel matrix resulting in binding of the C-probe to the matrix through interaction between the ligand and ligand binding moiety. In the presence of target nucleic acid molecules, C-probe will bind to the target nucleic acid molecule through complementary sequences. Addition of ligase results in formation of closed C-probe that is subsequently amplified by rolling circle amplification or RAM. Alternatively, the C-probe can be linked to the gel matrix through either direct linkage to the gel matrix or through binding to a ligand previously linked to the gel matrix. The target nucleic acid molecule is then hybridized to a primer and primer extension is carried out for amplification and detection of the target nucleic acid molecule.

Examples of ligand/ligand binding moiety pairs include biotin with avidin/streptavidin, antigens or haptens with antibodies, heavy metal derivatives with thiogroups, various polynucleotides such as homopolynucleotides as poly dG with poly dC, poly dA with poly dT and poly dA with poly U. Any component pairs with strong affinity for each other can be used as the affinity pair, ligand-ligand binding moiety. Suitable affinity pairs are also found among ligands and conjugates used in immunological methods. The preferred ligand-ligand binding moiety for use in the present invention is the biotin/streptavidin affinity pair.

In a further embodiment of the invention, labeled nucleotides may be used during amplification to detect the amplified products. Such labels include but are not limited to fluorescent, chemiluminescent or radioactive labels.

In yet another embodiment of the invention, an oligonucleotide probe can be fixed on a solid support, such as for example glass or nitrocellulose membranes, followed by an overlay of a gel matrix material. Following addition of C-probe to the gel matrix, target nucleic acid molecules are added to the matrix and an amplification reaction is carried out thereby allowing the signal to be retained in situ.

In a further embodiment of the invention, the matrix material may be prepared as a bead form, i.e., sepharose, cellulose or nanoparticles, in which ligand/ligand binding moieties have been embedded.

In another embodiment of the invention, a protein, antibody or antigen may be embedded within a gel matrix. Such protein, antibody or antigen is then detected by addition of a "binding partner" having an affinity for such molecules. The binding partner is linked to a nucleic acid molecule which can then be detected using the amplification methods described herein, i.e., HSAM and RAM and rolling circle amplification.

The probe hybridization, ligation, and amplification may be carried out in a gel matrix such as polyacrylamide or agarose (See, for example, Dubiley S. et al., 1999, Nucleic Acids Research 27:i-iv). The large mutimeric amplicons generated by primer extension amplification and/or subsequent ramification amplification can be visualized with a fluorescent microscope. Because the gel matrix prevents diffusion, any positive signal will appear as distinct "dots". Alternatively, the bound RAM probe can be detected using the hybridization signal amplification method (HSAM).

Figure 19:
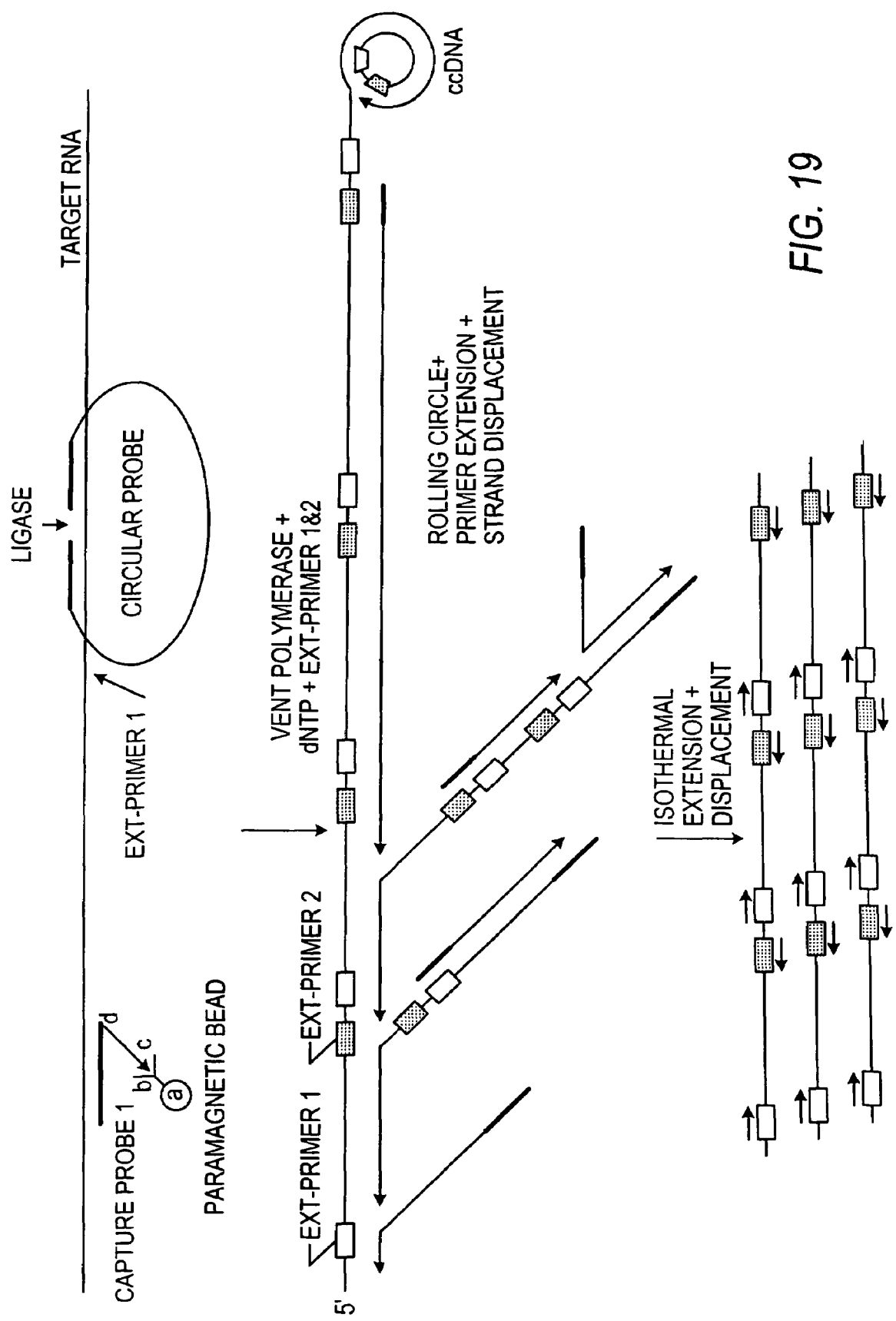
FIG. 19 is a schematic diagram of amplification of a circularized probe by the ramification-extension amplification method (RAM).

In embodiments of the present invention utilizing a ligation dependent circularizable probe, the resulting circular molecule may be conveniently amplified by the ramification-extension amplification method (RAM), as depicted in FIG. 19. Amplification of the circularized probe by RAM adds still further advantages to the methods of the present invention by allowing up to a million-fold amplification of the circularized probe under isothermal conditions. RAM is illustrated in FIG. 19.

The single, full length, ligation dependent circularizable probe useful for RAM contains regions at its 3' and 5' termini that are hybridizable to adjacent but not contiguous regions of the target molecule. The circularizable probe is designed to contain a 5' region that is complementary to and hybridizable to a portion of the target nucleic acid, and a 3' region that is complementary to and hybridizable to a portion of the target nucleic acid adjacent to the portion of the target that is complementary to the 5' region of the probe. The 5' and 3' regions of the circularizable probe may each be from about 20 to about 35 nucleotides in length. In a preferred embodiment, the 5' and 3' regions of the circularizable probe are about 25 nucleotides in length. The circularizable probe further contains a region designated as the linker region. In a preferred embodiment the linker region is from about 30 to about 60 nucleotides in length. The linker region is composed of a generic sequence that is neither complementary nor hybridizable to the target sequence.

The circularizable probe suitable for amplification by RAM is utilized in the present method with one or more capture/amplification probes, as described hereinabove. When the circularizable probe hybridizes with the target nucleic acid, its 5' and 3' termini become juxtaposed. Ligation with a linking agent results in the formation of a closed circular molecule.

Amplification of the closed circular molecule is effected by adding a first extension primer (Ext-primer 1) to the reaction. Ext-primer 1 is complementary to and hybridizable to a portion of the linker region of the circularizable probe, and is preferably from about 15 to about 30 nucleotides in length. Ext-primer 1 is extended by adding sufficient concentrations of dNTPs and a DNA polymerase to extend the primer around the closed circular molecule. After one revolution of the circle, i.e., when the DNA polymerase reaches the Ext-primer 1 binding site, the polymerase displaces the primer and its extended sequence. The polymerase thus continuously "rolls over" the closed circular probe to produce a long single strand DNA, as shown in FIG. 19.

The polymerase useful for amplification of the circularized probe by RAM may be any polymerase that lacks 3'→5' exonuclease activity, that has strand displacement activity, and that is capable of primer extension of at least about 1000 bases. (Bxo-)Klenow fragment of DNA polymerase, *Thermococcus litoralis* DNA polymerase (Vent (exo) DNA polymerase, New England Biolabs) and phi29 polymerase (Blanco et al., 1994, Proc. Natl. Acad. Sci. USA 91:12198) are preferred polymerases. *Thermus aguaticus* (Taq) DNA polymerase is also useful in accordance with the present invention. Contrary to reports in the literature, it has been found in accordance with the present invention that Taq DNA polymerase has strand displacement activity.

Extension of Ext-primer 1 by the polymerase results in a long single stranded DNA of repeating units having a sequence complementary to the sequence of the circularizable probe. The single stranded DNA may be up to 10 Kb, and for example may contain from about 20 to about 100 units, with each unit equal in length to the length of the circularizable probe, for example about 100 bases. As an alternative to RAM, detection may be performed at this step if the target is abundant or the single stranded DNA is long. For example, the long single stranded DNA may be detected at this stage by visualizing the resulting product as a large molecule on a polyacrylamide gel.

In the next step of amplification by RAM, a second extension primer (Ext-primer 2) is added. Ext-primer 2 is preferably from about 15 to about 30 nucleotides in length. Ext-primer 2 is identical to a portion of the linker region that does not overlap the portion of the linker region to which Ext-primer 1 is complementary. Thus each repeating unit of the long single stranded DNA contains a binding site to which Ext-primer 2 hybridizes. Multiple copies of the Ext-primer 2 thus bind to the long single stranded DNA, as depicted in FIG. 19, and are extended by the DNA polymerase. The primer extension products displace downstream primers with their corresponding extension products to produce multiple displaced single stranded DNA molecules, as shown in FIG. 19. The displaced single strands contain binding sites for Ext-primer 1 and thus serve as templates for further primer extension reactions to produce the multiple ramification molecule shown in FIG. 19. The reaction comes to an end when all DNA becomes double stranded.

The DNA amplified by RAM is then detected by methods known in the art for detection of DNA. Because RAM results in exponential amplification, the resulting large quantities of DNA can be conveniently detected, for example by gel electrophoresis and visualization for example with ethidium bromide. Because the RAM extension products differ in size depending upon the number of units extended from the closed circular DNA, the RAM products appear as a smear or ladder when electrophoresed. In another embodiment, the circularizable probe is designed to contain a unique restriction site, and the RAM products are digested with the corresponding restriction endonuclease to provide a large amount of a single sized fragment of one unit length i.e., the length of the circularizable probe. The fragment can be easily detected by gel electrophoresis as a single band. Alternatively, a ligand such as biotin or digoxigenin can be incorporated during primer extension and the ligand-labeled single stranded product can be detected as described hereinabove.

The RAM extension products can be detected by other methods known in the art, including, for example, ELISA, as described hereinabove for detection of PCR products.

In other embodiments of the present invention, the RAM assay is modified to increase amplification. In one embodiment, following the addition of Ext-primer 2, the reaction temperature is periodically raised to about 95° C. The rise in temperature results in denaturation of double stranded DNA, allowing additional binding of Ext-primers 1 and 2 and production of additional extension products. Thus, PCR can be effectively combined with RAM to increase amplification, as depicted in FIG. 16.

Figure 17:
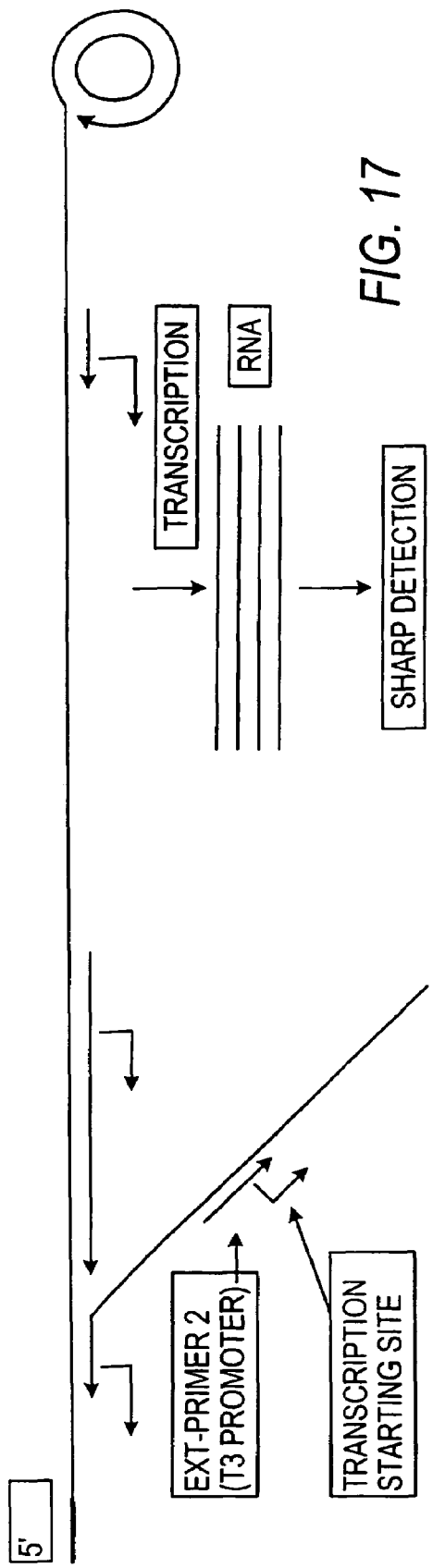
FIG. 17 is a schematic diagram of an embodiment of RAM in which a T3 promoter has been incorporated into Ext-primer 2, allowing amplification of the circular probe by transcription.

In another embodiment, the Ext-2 primer (and thus the identical portion of the linker region of the circularizable probe) is designed to contain a promoter sequence for a DNA-dependent RNA polymerase. RNA polymerases and corresponding promoter sequences are known in the art, and disclosed for example by Milligan et al. (1987) Nucleic Acid Res. 15:8783. In a preferred embodiment the RNA polymerase is bacteriophage T3, T7, or SP6 RNA polymerase. Addition of the Ext-primer 2 containing the promoter sequence, the corresponding RNA polymerase and rNTPs, allows hybridization of Ext-primer 2 to the growing single-stranded DNA to form a functional promoter, and transcription of the downstream sequence into multiple copies of RNA. This embodiment of the invention is illustrated in FIG. 17. In this embodiment, both RAM and transcription operate to produce significant amplification of the probe. The RNA can be detected by methods known to one of ordinary skill in the art, for example, polyaciylamide gel electrophoresis, radioactive or nonradioactive labeling and detection methods (Boehringer Mannheim), or the Sharp detection assay (Digene, Md.). Detection of the RNA indicates the presence of the target nucleic acid.

Figure 24:
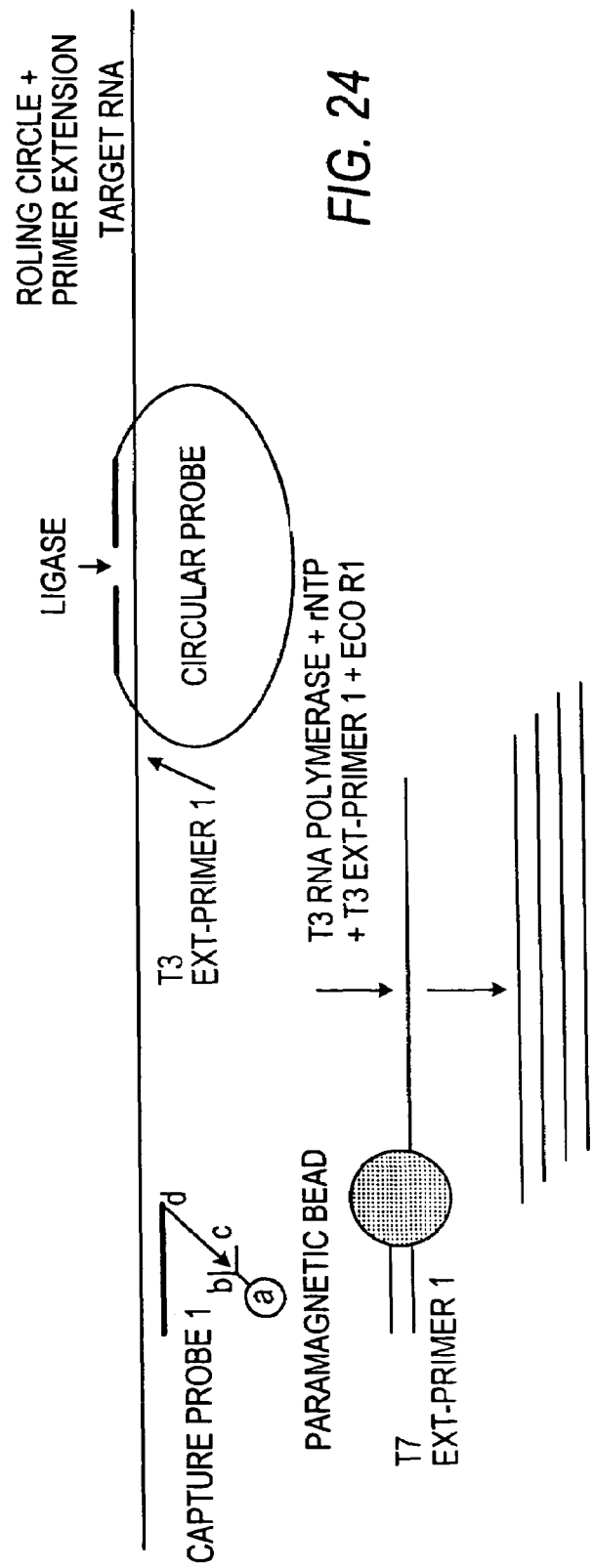
FIG. 24 is a diagram of a RAM assay in which an RNA polymerase promoter sequence is incorporated into the primer.

In another embodiment, Ext-primer 1 and the corresponding part of the linker region of the circular probe are designed to have a DNA-dependent RNA polymerase promoter sequence incorporated therein. Thus when Ext-primer 1 binds the circularized probe, a functional promoter is formed and the circularized probe acts as a template for RNA transcription upon the addition of RNA polymerase and rNTPs. The downstream primer and its RNA sequence are displaced by the RNA polymerase, and a large RNA polymer can be made. The RNA polymer may be detected as described hereinabove. Alternatively, the circular probe can be cleaved into a single stranded DNA by adding a restriction enzyme such as EcoRI. The restriction site is incorporated into the 5' end of extension primer 1, as shown in FIG. 24.

In another embodiment of the invention, an oligonucleotide primer pair is designed to provide a signal in the presence of circular probe specific RAM amplification. The first primer of the pair comprises a first sequence that is complementary to the circular probe and serves as a primer for RAM mediated amplification and a second sequence which is complementary to the second primer. In addition, the first primer is labeled with a signal generating moiety which is detectable in the presence of the first sequence generated from the circular probe by primer extension. Preferably the primer is labeled at its 5' end with the signal generating moiety. Such signal generating moieties include but are not limited to fluorescent, chemiluminescent or enzymes. Examples include but are not limited to luciferase and fluorescein and quantum dots.

Figure 20:
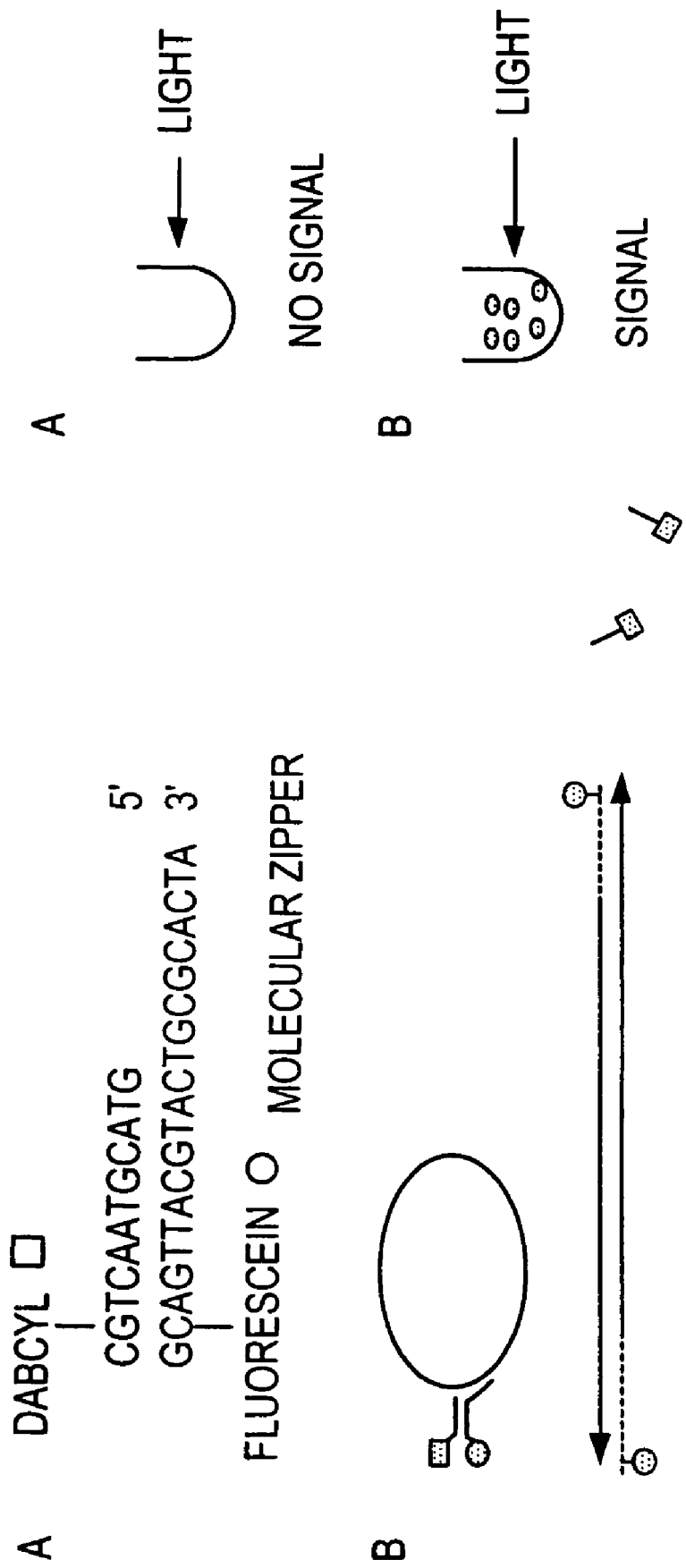
FIG. 20 is a diagram of amplification of a circularized probe by the ramification extension amplification method using a molecular "zipper" associated with a signal generating moiety.

The second primer of the pair comprises a sequence that is complementary to the second sequence of the first primer such that a "zipper region" is formed when the primers hybridize to one another. In addition, the second primer is labeled, preferable at the 3' end, with a moiety capable of quenching, masking or inhibiting the activity of the signal generating moiety when located adjacent to or in close proximity to said signal (See, for example, FIG. 20). Such inhibitory molecules include but are not limited to quenchers of fluorescent or chemiluminescent signals or inhibitors of enzyme activity.

In another embodiment of the invention, the first primer of the pair comprises a first sequence that is complementary to the target nucleic acid and serves as a primer for amplification of target nucleic acid molecules using a variety of different amplification methods including but not limited to RAM, polymerase chain reaction, transcription mediated assay (Sarrazin C. et al., 2001, J Clin Microbiol. 39:2850-5) and strand displacement amplification assay (Nadeau et al., 1999, 276:177-87) and a second sequence which is complementary to the second primer. In addition, the first primer is labeled with a signal generating moiety.

Figure 32:
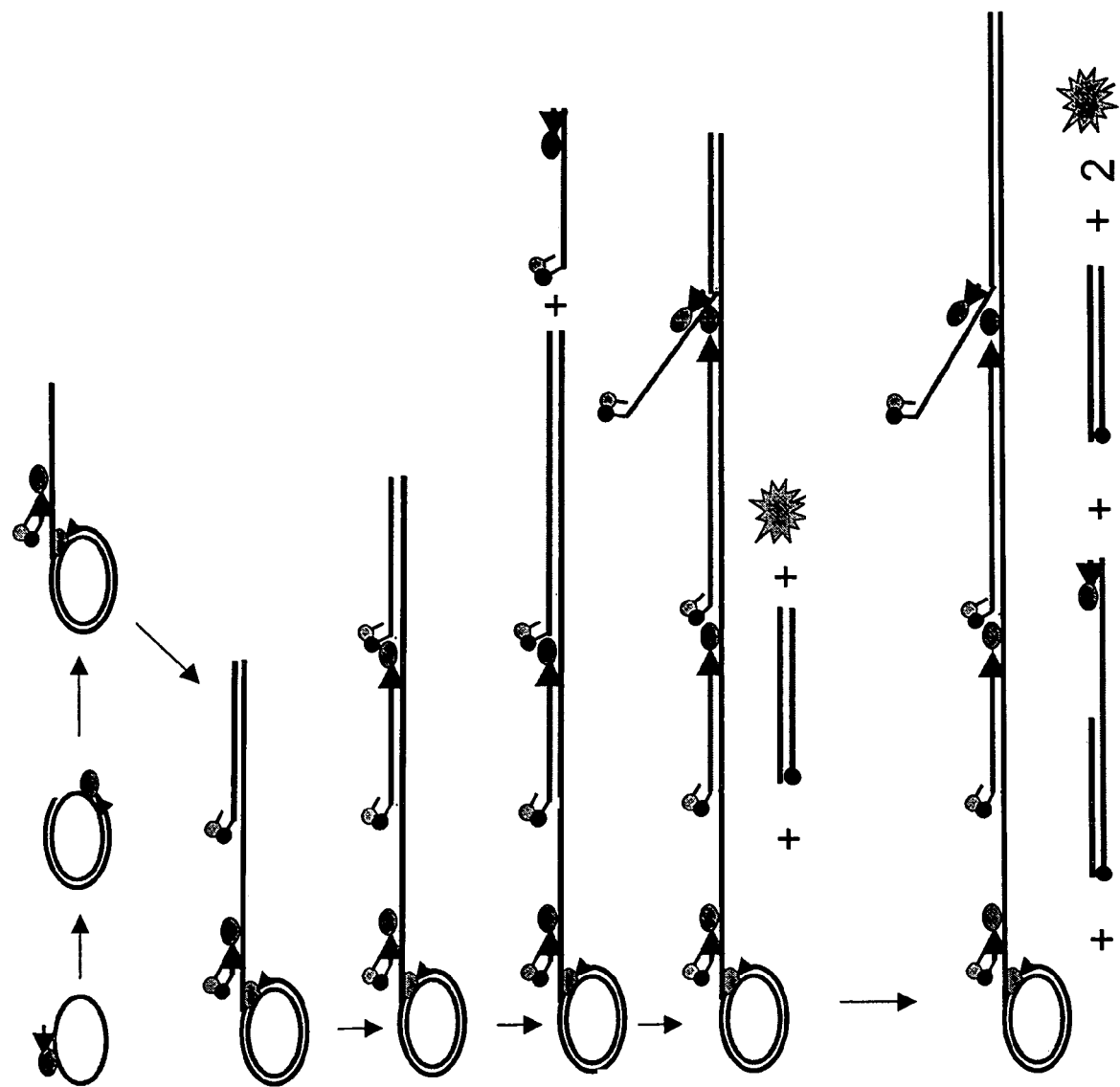
FIG. 32 is a schematic depiction of RAM amplification using molecular zipper probes.

The primers are designed in such a way that the signal generating moiety and the inhibitory moiety are adjacent to, or in close proximity to one another, thereby inhibiting the generation of a detectable signal. However, upon binding to a circular probe, and following primer extension, the primers are "unzippered" or spatially separated from one another, thereby permitting the detection of signal. In addition, primers conjugated to signal generating and inhibitory moieties may be used to detect amplification of target nucleic acid molecules using a variety of different amplification methods including but not limited to RAM, polymerase chain reaction, transcription mediated assay (Sarrazin C. et al., 2001, J Clin Microbiol. 39:2850-5) and strand displacement amplification assay (Nadeau et al., 1999, Anal. Biochem. 276:177-87). The only requirement is that the amplification method results in the spatial separation of the signal generating moiety and the inhibitory moiety. Such amplification methods are well known to those of skill in the art. (FIG. 32)

In another embodiment of the invention, the circular probe specific RAM amplification may be carried out using: at least one forward primer, each of which comprises a sequence complementary to a portion of the circular probe; at least one reverse primer, each of which comprises a sequence that is substantially identical to a portion of the circular probe; and an oligonucleotide primer pair comprising a first primer and a second primer. The first primer of the oligonucleotide primer pair may be comprised of a first sequence that is identical to a portion of the circular probe and serves as a primer for RAM mediated amplification and a second sequence which is complementary to the second primer. In addition, the first primer may be labeled with a signal generating moiety which is detectable in the presence of the first sequence generated from the circular probe by primer extension. The second primer of the oligonucleotide primer pair may comprise a sequence that is complementary to the first primer. In addition, the second primer may be labeled with a moiety capable of quenching, masking or inhibiting the activity of the signal generating moiety when located adjacent to or in close proximity to said signal.

In another embodiment of the invention, the circular probe specific RAM amplification may be carried out using: at least one first oligonucleotide primer pair comprising a first primer and a second primer and at least one second oligonucleotide primer pair comprising a first primer and a second primer. The first primer of the first primer pair may comprise a first sequence that is complementary to the circular probe and thus serves as a forward primer in the RAM mediated amplification and a second sequence that is complementary to the second primer of the first primer pair. In addition, the first primer of the first primer pair may be labeled with a signal generating moiety. The second primer of the first primer pair may comprise a sequence that is complementary to the first primer of the first primer pair. In addition, the second primer of the first primer pair may be labeled with an inhibitory or quenching moiety.

The first primer of the second primer pair may comprise a first sequence that is identical to the circular probe and thus serves as a reverse primer in the RAM mediated amplification and a second sequence that is complementary to the second primer of the second primer pair. In addition, the first primer of the second primer pair may be labeled with a signal generating moiety. The second primer of the second primer pair may comprise a sequence that is complementary to the first primer of the second primer pair. In addition, the second primer of the second primer pair may be labeled with an inhibitory or quenching moiety.

In a further embodiment of the invention, the circular probe specific RAM amplification may be carried out using: a reverse primer, comprising a sequence that is substantially identical to a portion of the circular probe, and a multiple oligonucleotide primer comprising a first primer, a second primer and a third primer. The first primer may comprise a first sequence that is complementary to the circular probe and thus serves as a forward primer in the RAM mediated amplification; a second sequence that is complementary to the second primer and a third sequence that is complementary to the third primer. The second primer may comprise a sequence that is complementary to the first primer and is labeled with a signal generating moiety. The signal generating moiety may be located on either the 5' or 3' end of the second primer. The third primer may comprise a sequence that is complementary to the first primer and is labeled with an inhibitory or quenching moiety. The quenching moiety may be located on either the 5' or 3' end of the third primer, so long as when the first, second and third primers are bound to one another the signal generating moiety and the quenching moiety are adjacent to or in close proximity to each other so as to inhibit the signal from being emitted. Upon completion of the RAM amplification the first and second primers will be displaced, thus allowing a signal to be emitted from the signal generating moiety.

In an additional embodiment of the invention, the circular probe specific RAM amplification may be carried out using: a forward primer, comprising a sequence that is complementary to a portion of the circular probe, and a multiple oligonucleotide primer comprising a first primer, a second primer and a third primer. The first primer may comprise a first sequence that is substantially identical to the circular probe and thus serves as a reverse primer in the RAM mediated amplification; a second sequence that is complementary to the second primer and a third sequence that is complementary to the third primer. The second primer may comprise a sequence that is complementary to the first primer and is labeled with a signal generating moiety. The signal generating moiety may be located on either the 5' or 3' end of the second primer. The third primer may comprise a sequence that is complementary to the first primer and is labeled with an inhibitory or quenching moiety. The quenching moiety may be located on either the 5' or 3' end of the third primer, so long as when the first, second and third primers are bound to one another the signal generating moiety and the quenching moiety are adjacent to or in close proximity to each other so as to inhibit the signal from being emitted. Upon completion of the RAM amplification the first and second primers will be displaced, thus allowing a signal to be emitted from the signal generating moiety.

In a further embodiment the target nucleic acid may be amplified using: at least one oligonucleotide primer pair comprising a first primer and a second primer and at least one reverse oligonucleotide primer, comprising a sequence that is substantially identical to a portion of the target nucleic acid. The first primer of the oligonucleotide primer pair may comprise a first sequence that is complementary to the target nucleic acid and a second sequence that is complementary to the second primer of the oligonucleotide primer pair. In addition, the first primer of the oligonucleotide primer pair may be labeled with a signal generating moiety. The second primer of the oligonucleotide primer pair may comprise a sequence that is complementary to the first primer of the oligonucleotide primer pair. In addition, the second primer of the oligonucleotide primer pair may be labeled with an inhibitory or quenching moiety.

The first and second primers of the oligonucleotide primer pair are designed in such a way that the signal generating moiety and the inhibitory moiety are adjacent to, or in close proximity to one another, thereby inhibiting the generation of a detectable signal. Upon binding to a target nucleic acid, the primer is extended and the reverse primer can bind to the nascent primer extension product. Upon primer extension of the reverse primer, the first and second primers of the oligonucleotide primer pair are "unzippered" or spatially separated from one another, thereby permitting the detection of signal.

In addition, primers conjugated to signal generating and inhibitory moieties may be used to amplify and detect target nucleic acid molecules using a variety of different amplification methods including but not limited to RAM, polymerase chain reaction, transcription mediated assay (Sarrazin C. et al., 2001, J Clin Microbiol. 39:2850-5) and strand displacement amplification assay (Nadeau et al., 1999, Anal. Biochem. 276:177-87). The only requirement is that the amplification method results in the spatial separation of the signal generating moiety and the inhibitory moiety. Such amplification methods are well known to those of skill in the art.

Figure 21A:
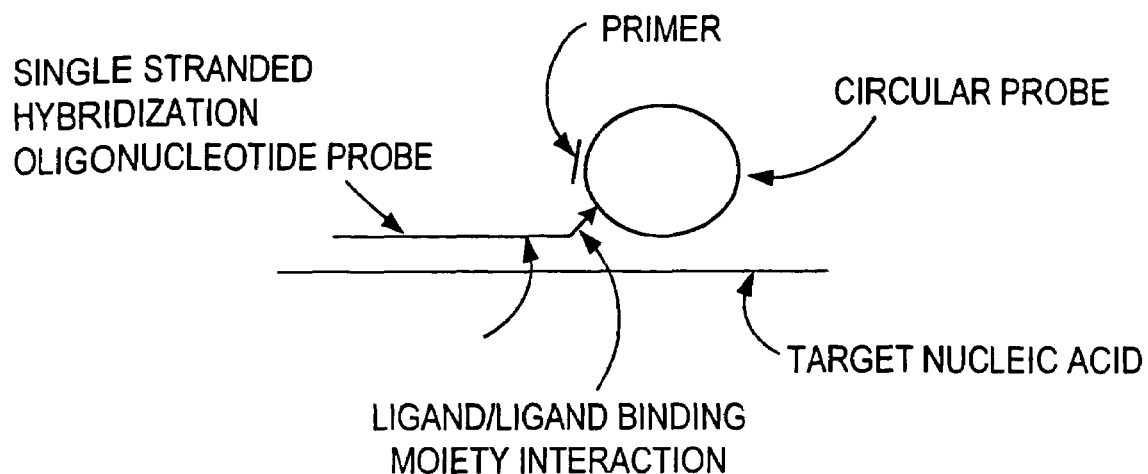
FIG. 21A-B is a diagram an anchoring primer extension amplification methods using hybridization probes associated with ligand binding moieties.
Figure 21B:
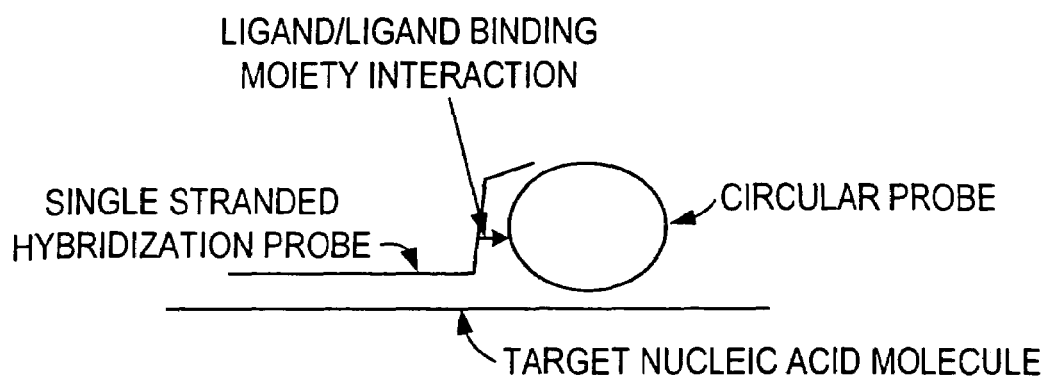

In an additional embodiment of the invention a single stranded oligonucleotide hybridization probe (Cap-Amp probe), PNA probe (Demidov VV et al., 2001, Methods 23:123-31), or LNA probe (Koshkin AA et al., 1998, Tetrahedron 54: 3607-3630) that binds specifically to target nucleic acid, is synthesized with a ligand moiety, such as for example, biotin, attached to its end. Although the probes may be of various lengths, it is preferred that such probes range in size from 15 to 40 nucleotides in length. In addition, a circular probe is designed to also contain ligand moieties in their linker region. Once the circular probe is ligated to form a circle, it is incubated with hybridization probe in the presence of a ligand binding moiety, such as for example streptavidin, resulting in the formation of a hybridization probe/ligand binding moiety/circular probe complex. If target sequences are present, the hybridization probe will bind to the target nucleic acid thereby anchoring the C-probe onto the target. In the test, the Cap-Amp probe can be incubated with test sample, followed by addition of ligand binding moieties and ligand labeled circular probe. The circular probe is then amplified by addition of primers and DNA polymerase as described above. Alternatively, the Cap-Amp probe can be designed with a region complementary to the target, a 3' region complementary to C-probe and an internal ligand moiety in between. In this way, when bound to the C-probe internally, the 3' end of the Cap-Amp probe that hybridizes to the C-probe can serve as a primer for initial primer extension and ramification amplification. (FIG. 21A-B)

Figure 21C:
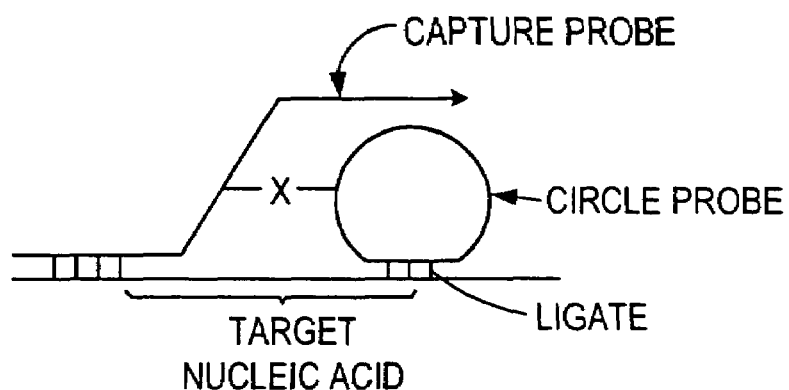
FIG. 21C-D is a diagram of primer extension amplification methods using hybridization probes.

In addition the present invention provides a method for detection of a target nucleic acid in a sample comprising contacting the nucleic acid with a hybridization probe which comprises a single stranded oligonucleotide having (i) a region that is complementary to the target nucleic acid and (ii) a region complementary to the circular probe. In addition, the target nucleic acid is contacted with a circular probe comprising a single stranded oligonucleotide having (i) a region that is complementary to the target nucleic acid and a region complementary to the hybridization probe, wherein said hybridization probe acts as a primer for amplification of the circular probe in the presence of the target nucleic acid. The hybridization probe is then extended by addition of DNA polymerase followed by amplification of the circular probe wherein detection of amplification of the circular probe indicates the presence of the target nucleic acid. (FIG. 21C)

Figure 21D:
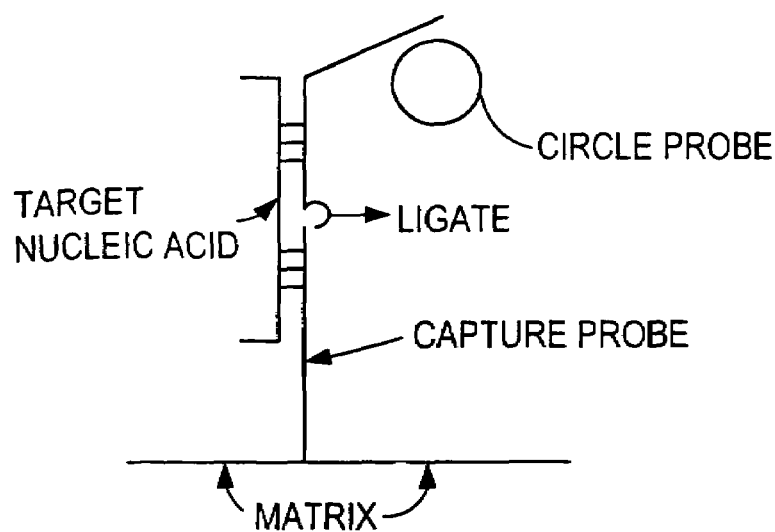

In yet another embodiment of the invention a method is provided for detection of a target nucleic acid in a sample comprising contacting said nucleic acid with a first hybridization probe linked to a solid support wherein said hybridization probe comprises a single stranded oligonucleotide having (i) a region that is complementary to the target nucleic acid; and (ii) a circular probe bound by complementary sequences to said-second hybridization probe. In the presence of a target nucleic acid molecule the first hybridization probe and second hybridization probe are adjacent to one another thereby permitting ligation of the first hybridization probe to the second hybridization probe following addition of ligase. The circular probe is then amplified wherein detection of amplification of the circular probe indicates the presence of the target nucleic acid molecule. (FIG. 21D)

An additional embodiment of the invention provides for a method for detection of a target antigen or antibody in a sample. The target antigen or target antibody is contacted by an antibody that will bind specifically to the target. The antibody is attached to an anchoring oligonucleotide comprising a ligand moiety, such as for example, biotin, attached to its end. A circular probe comprising the ligand moiety is added in the presence of a ligand binding moiety, such as for example streptavidin, resulting in the formation of an antibody-anchoring oligonucleotide/ligand binding moiety/circular probe complex. The circular probe is then amplified by addition of primers and DNA polymerase as described above. Alternatively, the anchoring oligonucleotide can be designed with a region complementary to the circular probe and an internal ligand moiety. In this way, when bound to the circular probe internally, the end that hybridizes to the circular probe can serve as a primer for initial primer extension and ramification.

Figure 27:
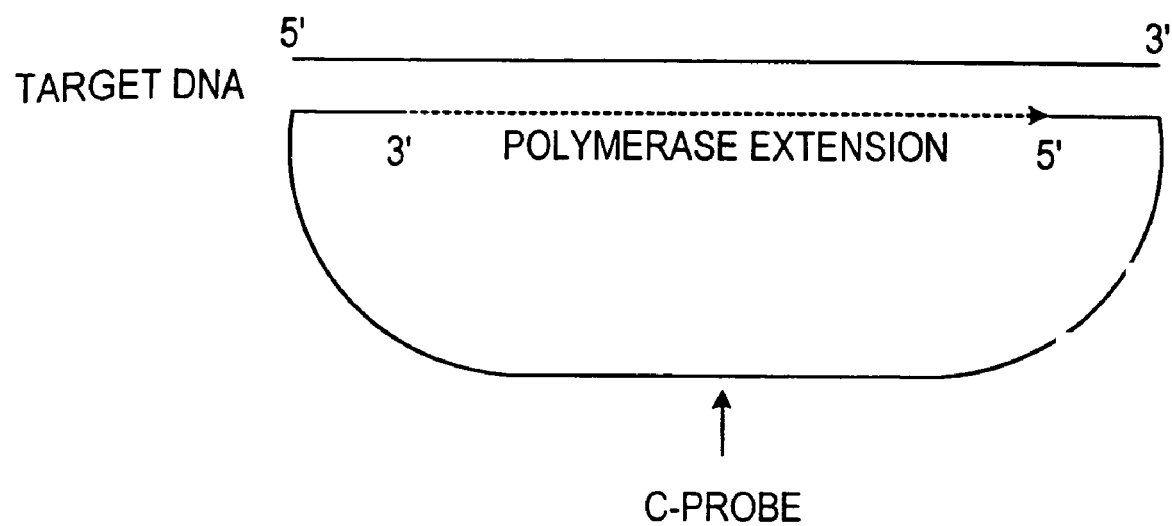
FIG. 27 depicts a RAM assay where target sequences of increased lengths are amplified.

In the methods described above RAM amplification is used to amplify the probe. However, modification of the design of the Amp-probe-2 may be used to amplify target sequences. In such instances, the 3' and 5' end of the Amp-probe-2 are separated by the target sequences that are intended to be amplified (FIG. 27). The sequences may range in size from a few nucleotides to several thousand nucleotides. The gap between the 3' end and the 5' end of the probe will be filled using a DNA polymerase which lacks 5'-3' exonuclease and displacement activities. Such polymerases are well known to those skilled in the art and include but are not limited to T4 DNA polymerase and modified polymerases lacking exonuclease activity. If the target nucleic acid is RNA, the gap between the 3' end and the 5' end of the probe will be filled using reverse transcriptase. Following extension, the gap is closed in with ligase and amplification of the DNA is performed using an ext-primer 1 to generate a long single stranded DNA. Addition of a second primer, ext-primer 2 allows amplification of the single stranded DNA by RAM as described above.

As described above, the methods of the invention may be used in assays to specifically detect infectious pathogenic agents and normal and abnormal genes. The present invention further provides methods for general amplification of total genomic DNA or mRNA expressed within a cell. The use of such methods provides a means for generating increased quantities of DNA and/or mRNA from small numbers of cells. Such amplified DNA and/or mRNA may then be used in techniques developed for detection of infectious agents, and detection of normal and abnormal genes.

Figure 30:
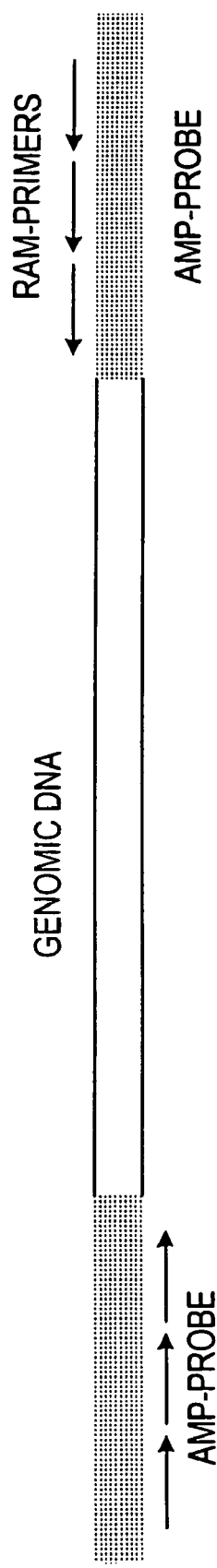
FIG. 30 depicts the genetic amplification of genomic DNA using adaptor molecules.
Figure 31:
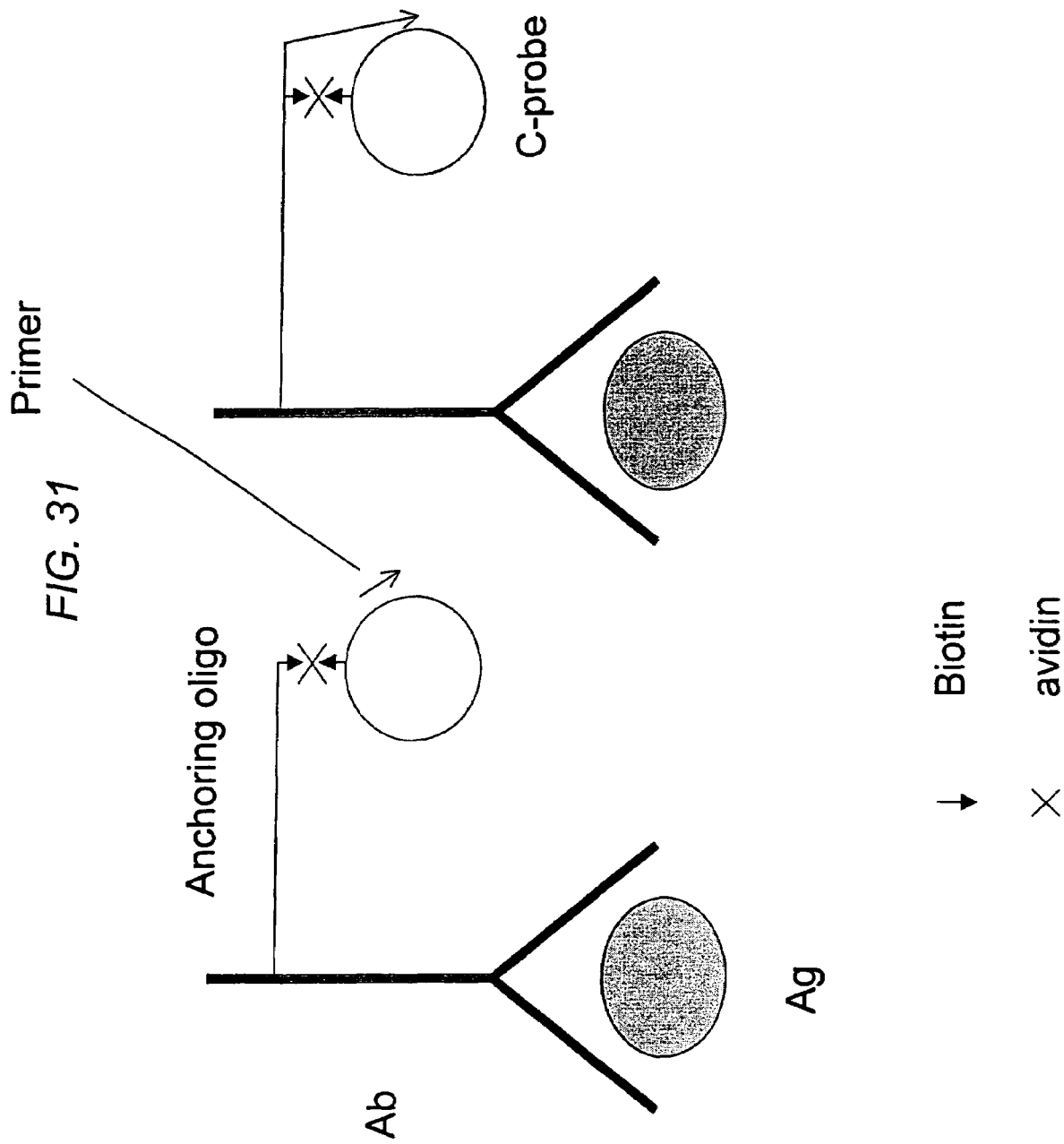
FIG. 31 is a diagram of the detection of an antigen using an antibody conjugated to an Anchoring oligonucleotide.

To amplify genomic DNA, a genomic DNA sample is prepared from cells using any of a variety of different methods well known in the art. Once isolated, the genomic DNA sample is digested with a selected restriction endonuclease. Restriction endonucleases that may be utilized for digestion of genomic DNA include, for example, any of those various enzymes commercially available. After digestion of genomic DNA, a double-stranded amp-probe is added to the reaction. The amp-probe is a double stranded DNA fragment of approximately 70-130 nucleotides containing a protruding sequence complimentary to the restriction endonuclease site of the digested genomic DNA. The amp-probe is designed to contain multiple primer sites that will be used to RAM amplify the genomic DNA. In instances where multiple restriction endonucleases are used to digest the DNA, multiple Amp-probes will be added with protruding sites complimentary to the different restriction sites. After annealing the amp-probes, ligase is added to the reaction to ligate the amp-probe sequences to the fragmented genomic DNA. This process may be repeated a number of times to ensure complete digestion of genomic DNA. (FIG. 30)

In an embodiment of the invention, to reduce the possibility of adaptor self-ligation, a first strand amp-probe may be added to the reaction containing the digested genomic DNA followed by ligation of the first strand amp-probe to the genomic DNA. Following a wash step to remove the unligated first strand amp-probe, a second strand amp-probe, which will hybridize to the complementary sequences of the first strand amp-probe, is added. Ligase is added to the reaction a second time, resulting in genomic DNA fragments containing double stranded amp-probes ligated to each end.

The length of the amp-probe sequence can be increased by repeated digestion of the DNA fragments with the selected restriction endonuclease and repeated hybridization, washing and ligation steps. Because the opposite end of the amp-probe is designed to contain a restriction endonuclease site, digestion with the restriction endonuclease will create a new site for the first amp-probe to bind to. The process can be repeated multiple times thereby increasing the amp-probe length and thus increasing the number of RAM primer binding sites.

Following addition of the amp-probe, the genomic DNA is denatured and RAM primers designed to bind to sequences within the amp-probe are added. DNA polymerase and dNPTs are added to the reaction and RAM mediated amplification is initiated. The DNA polymerase to be used in the amplification reaction is preferably one with a strong displacement activity and high processivity, such as, for example, φ29 or Bst DNA polymerase.

In an embodiment of the invention, the addition of amp-probes to the ends of the digested genomic DNA can be initially performed in a gel matrix to ensure the integrity of the DNA fragments and that all the ends contain an amp-probe sequence. The efficiency of the amplification step is dependent on the number of primer binding sites available in the amp-probe sequence. Thus, for efficient amplification multiple primer binding sites should be available within the amp-probe sequences. The DNA fragments can be removed from the gel matrix and subsequent amplification carried out in a reaction vessel. The advantage this method of general genomic amplification provides over other PCR based methods is the absence of a requirement for multiple cycling and it ensures that all DNA fragments are amplified.

Total mRNA may also be amplified using the RAM techniques of the present invention. Cellular mRNAs may be purified using methods well known for isolation of RNA including but not limited to capture onto support matrices, such as magnetic beads, or nitrocellulose membranes using oligo(dT) Capture/Amp-probe-1 probes. The Capture/Amp-probe-1 is designed to contain an anchor sequence followed by a stretch of 20 nucleotides of T which is followed by a RAM primer binding sequence. Reverse transcription by incubation with a reverse transcriptase results in generation of a single stranded cDNA. The single stranded cDNA is then converted to dsDNA using methods well known to those of skill in the art. A second dsDNA AMP-probe-2 is ligated to the 5' end of the cDNA. The resulting total cDNA is then amplified as described above for genomic DNA.

The present invention also provides a novel method for analyzing differential mRNA expression patterns between cells, referred to herein as differential display RAM (DD-RAM). The method involves (i) reverse transcription of mRNA using a 5' Capture/Amp probe-1 sequence as primer; (ii) ligation of the 3' end of the extended sequence to the 5' end of a Arbitrary/Amp probe-2 annealed to the mRNA; (iii) RAM amplification using a set of RAM primers (forward and reverse primers); and (iv) electrophoretic separation of the resulting fragments. The resulting fragments from different types of cells are compared to identify differentially expressed mRNAs. The method of the invention may further comprise digestion of the resulting cDNA with a restriction endonuclease that recognizes a site in the primer.

In addition to the 3' complementary region, each 5' Capture/Amp-probe will contain a generic sequence for RAM primers to bind and, for example, a biotin moiety at the probe 5' end. The 5' Capture/Amp probe-1 is designed to bind to the 3' end of the mRNA and will serve both as a capture probe for mRNA isolation and primers for reverse transcription. The 3' Arbitrary/Amp probe-2 is designed to contain a 5' degenerative sequence for binding to the 5' end of the mRNA and a generic sequence for RAM primers to bind.

In a specific embodiment of the invention, following hybridization of the probes with mRNA, the probe/mRNA complex is isolated by capture onto a support matrix, such as magnetic streptavidin beads via biotin, or oligo (dT) nitrocellulose through the 5' anchor probes. Extensive washes are performed to remove any unbound probe and cellular DNA. Addition of reverse transcriptase results in production of a first strand cDNA which terminates at the 5' end of the Arbitrary/Amp probe-2. Ligation joins the two fragments, i.e., the 5' end of the Arbitrary/Amp probe-2 and the extended sequence, which then serve as template for subsequent RAM amplification.

To increase the assay sensitivity, a subtraction step may be performed before reverse transcription is performed. For subtraction, primers 12-15 nucleotides in length and complementary to known housekeeping and/or structural gene sequences are added to the hybridization mix. The primers are designed to bind to the 3' region of the housekeeping and/or structural mRNAs with a few nucleotides overlapping with the anchor probe, thereby, competing with the Capture/Amp probe-1 for binding to mRNA. For example, 12-15 nucleotide long primers synthesized to complement the 3' end of housekeeping and/or structural mRNAs such as keratin, laminin, tubulin, acetylcoenzyme, adenosine deaminase, adenylate kinase, and aldolase A will be added to the hybridization mix. Before adding reverse transcriptase, the reaction is incubated with an RNA specific enzyme which specifically cleaves the RNA strand of an RNA-DNA duplex. Such enzymes, include for example, RNases such as RNaseH. The RNase treatment is designed to eliminate the large number of highly expressed housekeeping mRNAs thereby increasing the sensitivity of the assay.

In addition a single probe may be designed to comprise a 5' anchor sequence and a 5' arbitrary sequence. The probe may be labeled with a binding moiety, such as biotin, to facilitate isolation of the hybrid molecules from the reaction mixture (for example, using streptavidin beads). A reverse transcriptase reaction is carried out to extend the region between both ends of the primer followed by ligation to form closed circular molecules which can be subsequently amplified by RAM. After digestion with a restriction endonuclease, the resulting products can be examined on a sequencing gel.

The present invention provides advantages over other types of differential display methods in that (i) each mRNA has only one corresponding RAM product because only the first available 3' Arbitrary/Amp-probe will be ligated to the extended sequence, therefore, reducing the redundant presentation of the same mRNA; (ii) all ligated probes are amplified by the same pair of primers, therefore, minimizing different primer amplification efficiencies; and (iii) with the addition of a subtraction step, housekeeping and/or structural mRNAs are eliminated from the reaction, thus increasing assay sensitivity and specificity.

The DD-RAM techniques described herein can be utilized to identify mRNAs that are differentially expressed within different cell types. For example, the technique will permit rapid screening of large numbers of tumor cells at different stages of tumorgenesis thereby providing a method for the identification of important genes that are closely related to tumorogenesis.

Reagents for use in practicing the present invention may be provided individually or may be packaged in kit form. For example, kits might be prepared comprising one or more first, e.g., capture/amplification-1 probes and one or more second, e.g., amplification-probe-2 probes, preferably also comprising packaged combinations of appropriate generic primers. Kits may also be prepared comprising one or more first, e.g., capture/amplification-1 probes and one or more second, full length, ligation-independent probes, e.g., amplification-probe-2. Still other kits may be prepared comprising one or more first, e.g., capture/amplification-1 probes and one or more second, full length, ligation-dependent circularizable probes, e.g., amplification-probe-2. Such kits may preferably also comprise packaged combinations of appropriate generic primers. Optionally, other reagents required for ligation (e.g., DNA ligase) and, possibly, amplification may be included. Additional reagents also may be included for use in quantitative detection of the amplified ligated amplification sequence, e.g., control templates such as an oligodeoxyribonucleotide corresponding to nanovariant RNA. Further, kits may include reagents for the in situ detection of target nucleic acid sequences e.g. in tissue samples. The kits containing circular probes may also include exonuclease for carryover prevention.

The arrangement of the reagents within containers of the kit will depend on the specific reagents involved. Each reagent can be packaged in an individual container, but various combinations may also be possible.

The present invention is illustrated with the following examples, which are not intended to limit the scope of the invention.

EXAMPLE 1

Detection of HIV-1 RNA in a Sample

Preparation of Oligonucleotide Probes

A pair of oligodeoxyribonucleotide probes, designated Capture/Amp-probe-1 (HIV) and Amp-probe-2 (HIV), respectively for detecting the gag region of HIV-1 RNA were prepared by automated synthesis via an automated DNA synthesizer (Applied Biosystems, Inc.) using known oligonucleotide synthetic techniques. Capture/Amp-probe-1 (HIV) is an oligodeoxyribonucleotide comprising 59 nucleotides and a 3' biotin moiety, which is added by using a 3'-biotinylated nucleoside triphosphate as the last step in the synthesis. The Capture/Amp-probe-1 (HIV) used in this Example has the following nucleotide sequence (also listed below as SEQ ID NO. 1):

```
         1          11         21
5'-CCATCTTCCT GCTAATTTTA AGACCTGGTA 31          41         51
   ACAGGATTTC CCCGGGAATT CAAGCTTGG-3'
```

The nucleotides at positions 24-59 comprise the generic 3' end of the probe. Within this region are recognition sequences for SmaI (CCCGGG), EcoRI (GAATTC) and HindIII (AAGCTT) at nucleotides 41-46, 46-51 and 52-57, respectively. The 5' portion of the sequence comprising nucleotides 1-23 is complementary and hybridizes to a portion of the gag region of HIV-1 RNA.

Amp-probe-2 (HIV) is a 92 nucleotide oligodeoxyribonucleotide which has the following sequence (also listed below as SEQ ID NO. 2):

```
         1          11         21         31         41
5'-GGGTTGACCC GGCTAGATCC GGGTGTGTCC TCTCTAACTT TCGAGTAGAG 51         61         71         81         91
   AGGTGAGAAA ACCCCGTTAT CTGTATGTAC TGTTTTTACT GG-3'
```

The nucleotides at positions 71-92 comprise the 3' specific portion of this probe, complementary and hybridizable to a portion of the gag region of HIV-1 RNA immediately adjacent to the portion of the gag region complementary to nucleotides 1-23 of Capture/Amp-probe-1 (HIV). Nucleotides 1-70 comprise the generic 5' portion of Amp-probe-2 (HIV).

Ligation of the 5' end of Capture/Amp-probe-1 (HIV) to the 3' end of Amp-probe-2 (HIV) using $T_4$ DNA ligase creates the ligated amplification sequence (HIV) having the following sequence (also listed below as SEQ ID NO. 3):

```
         1          11         21         31
5'-GGGTTGACCC GGCTAGATCC GGGTGTGTCC TCTCTAACTT 41         51         61         71
   TCGAGTAGAG AGGTGAGAAA ACCCCGTTAT CTGTATGTAC 81         91        101        111
   TGTTTTTACT GGCCATCTTC CTGCTAATTT TAAGACCTGG 121        131        141        151
   TAACAGGATT TCCCCGGGAA TTCAAGCTTG G-3'
```

This ligated amplification sequence is 151 nucleotides long, which provides an ideal sized template for PCR.

The generic nucleotide sequences of the ligated amplification sequence (HIV) comprising nucleotides 116-135 (derived from nucleotides 24-43 of Capture/Amp-probe-1 (HIV) and nucleotides 1-70 (derived from nucleotides 1-70 of Amp-probe-2 (HIV)) correspond in sequence to nucleotides 1-90 of the (−) strand of the WSI nanovariant RNA described by Schaffner et al., J. Molec. Biol. 117:877-907 (1977). WSI is one of a group of three closely related 6 S RNA species, WSI, WSII and WSIII, which arose in Qβ replicase reactions without added template. Schaffher et al. termed the three molecules, "nanovariants."

The 90 nucleotide long oligodeoxyribonucieotide corresponding to nucleotides 1-90 of the WSI (−) strand has the following sequence (also listed below as SEQ ID NO. 4):

```
     1          11         21         31         41
5'-GGGTTGACCC GGCTAGATCC GGGTGTGTCC TCTCTAACTT
TCGAGTAGAG
    51         61         71         81
   AGGTGAGAAA ACCCCGTTAT CCTGGTAACA GGATTTCCCC-3'
```

Two generic oligodeoxynucleotide primers were also-synthesized for use in PCR amplification of the ligated amplification sequence. Primer-1, which has a length of 21 nucleotides, is complementary to the 3' sequence of Capture/Amp-probe-1 (HIV) (nucleotides 38-58) and has the sequence (also listed below as SEQ ID NO. 5):

```
       1          11
    5'-CAAGCTTGAA TTCCCGGGGA A-3'
```

Primer-2, which has a length of 20 nucleotides, corresponds in sequence to the 5' sequence of Amp-probe-2 (HIV) (nucleotides 1-20) and has the sequence (also listed below as SEQ ID NO. 6):

```
       1          11
    5'-GGGTTGACCC GGCTAGATCC-3'
```

Capture and Detection of HIV-1 RNA

Target HIV-1 RNA (100 µl) is dissolved in an equal volume of lysis buffer comprising SM GnSCN, 100 mM EDTA, 200 mM Tris-HCl (pH 8.0), 0.5% NP-40 (Sigma Chemical Co., St. Louis, Mo.), and 0.5% BSA in a 1.5 ml microfuge tube. Next, the 3'-biotinylated Capture/Amp-probe-1 (HW) (SEQ ID NO. 1) and Amp-probe-2 (HIV) (SEQ ID NO. 2), together with streptavidin-coated paramagnetic beads (obtained from Promega Corp.) were added to the lysed sample in the lysis buffer. A complex comprising target RNA/Capture/Amp-probe-1 (HIV)/Amp-probe-2 (HIV)/paramagnetic beads was formed and retained on the beads. A magnetic field generated by a magnet in a microfuge tube holder rack (obtained from Promega Corp.) was applied to the complex to retain it on the side of the reaction tube adjacent the magnet to allow unbound material to be siphoned off. The complex was then washed twice with a 1.5M GnSCN buffer to remove any unbound proteins, nucleic acids, and probes that may be trapped with the complex. The magnetic field technique facilitated the wash steps. The GnSCN then was removed by washing the complex with 300 mM KCl buffer (300 mM KCl, 50 mM Tris-HCl, pH 7.5, 0.5% Non-IDEP-40 1 mM EDTA).

The two probes were then covalently joined using $T_4$ DNA ligase (Boehringer Manheim) into a functional ligated amplification sequence (HIV) (SEQ ID NO. 3), which can serve as a template for PCR amplification. The ligation reaction was carried out in the presence of a 1× ligation buffer comprising a 1:10 dilution of 10×$T_4$ DNA ligase ligation buffer (660 mM Tris-HCl, 50 mM $MgCl_2$, 10 mM dithioeryritol, 10 mM ATP—pH 7.5 at 20° C.) obtained from Boehringer Manheim.

The paramagnetic beads containing bound ligated amplification sequence (HIV) were washed with 1×$T_4$ DNA ligase ligation buffer and resuspended in 100 µl of 1×$T_4$ DNA ligase ligation buffer. 20 µl of bead suspension was removed for the ligation reaction. 2 µl $T_4$ DNA ligase was added to the reaction mixture, which was incubated at 37° C. for 60 minutes.

For PCR amplification of the bound ligated amplification sequence (HIV), 80 µl of a PCR reaction mixture comprising Taq DNA polymerase, the two generic PCR primers (SEQ ID NOS. 5 and 6), a mixture of deoxynucleoside triphosphates and $^{32}$P-dCTP was added to the ligation reaction. A two temperature PCR reaction was carried out for 30 cycles in which hybrid formation and primer extension was carried out at 65° C. for 60 seconds and denaturation was carried out at 92° C. for 30 seconds.

Figure 3:
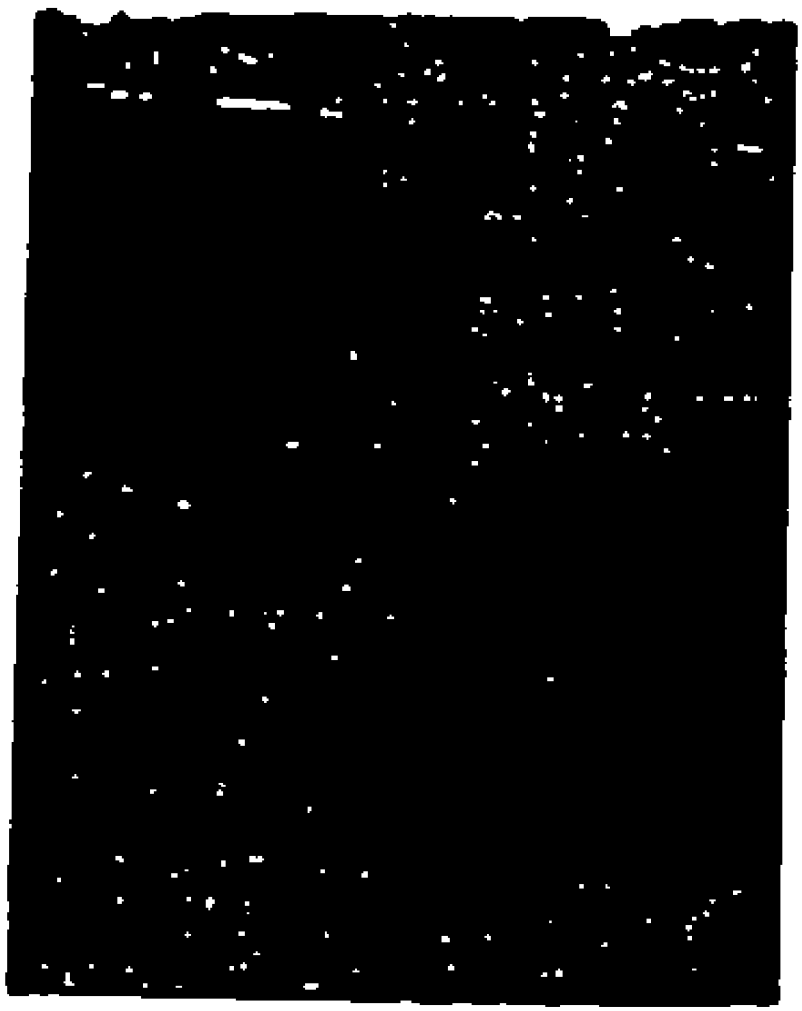
FIG. 3 is an autoradiograph depicting the detection of a PCR amplified probe that detects HIV-1 RNA. Lane A is the ligated amplification sequence according to the invention; Lane B, which is a control, is PCR amplified nanovariant DNA, that does not contain any HIV-1-specific sequences.

After 30 cycles, 10 p.l of the reaction mixture was subjected to electrophoresis in a 10% polyacrylamide gel and detected by autoradiography (FIG. 3, Lane A). As a control, nanovariant DNA (SEQ ID NO. 4) was also subjected to 30 cycles of two temperature PCR, under the same conditions as for the ligated amplification sequence (HIV), electrophoresed and autoradiographed (FIG. 3, Lane B). As can be seen from FIG. 3, the amplified ligated amplification sequence (HIV) migrated in a single band (151 nucleotides) at a slower rate than the amplified nanovariant DNA (90 nucleotides). The results also indicated that unligated first and second probes were either not amplified or detected.

EXAMPLE 2

Direct Detection of HIV-1 RNA in a Sample

The ability of the present method to directly detect the presence of HIV-1 RNA in a sample was also determined. The probes used in this Example are the same as in Example 1 (SEQ ID NOS. 1 and 2). For direct detection, Amp-probe-2 (HIV) (SEQ ID NO. 2) was labeled at its 5' end with $^{32}$P by the $T_4$ phosphokinase reaction using $^{32}$P-γ-ATP. The various reaction mixtures were as follows:

1. Streptavidin-coated paramagnetic beads, 3'-biotinylated Capture/Amp-probe-1 (HIV) (SEQ ID NO. 1), Amp-probe-2 (HIV) (SEQ ID NO. 2) 5'($^{32}$P), HIV-1 RNA transcript.

2. Streptavidin-coated paramagnetic beads, 3'-biotinylated Capture/Amp-probe-1 (HIV), Amp-probe-2 (HIV) 5'($^{32}$P).

3. Streptavidin-coated paramagnetic beads, Amp-probe-2 (HIV) 5'($^{32}$P), HIV-1 RNA transcript.

Hybridizations, using each of the above three reaction mixtures, were carried out in 20 µl of a 1M GnSCN buffer comprising 1M GnSCN, 0.5% NP-40 (Nonidet P-40, N-lauroylsarcosine, Sigma Chemical Co., St Louis, Mo.), 80 mM EDTA, 400 mM Tris HCl (pH 7.5) and 0.5% bovine serum albumin.

The reaction mixtures were incubated at 37° C. for 60 minutes. After incubation, the reaction mixtures were subjected to a magnetic field as described in Example 1 and washed (200 p.l/wash) two times with iM GnSCN buffer and three times with a 300 mM KCl buffer comprising 300 mM KCL, 50 mM Tris-HCl (pH 7.5), 0.5% NP-40 and 1 mM BDTA. The amount of $^{32}$P-labeled Amp-probe-2 (HIV) that was retained on the paramagnetic beads after washing is reported in Table 1 as counts-per-minute (CPM). The results indicate that, only in the presence of both target HIV RNA and Capture/Amp-probe-1 (HIV), is a significant amount of Amp-probe-2 retained on the beads and detected by counting in aβscintillation counter.

TABLE 1

Capture of target HIV RNA with Capture/Amp-probe-i (HIV)

| Reaction Mixture | CPM (after 2 washes with 1M GnSCN) | CPM (after 3 washes with 0.3M KCl) |
|---|---|---|
| 1. | 6254 | 5821 |
| 2. | 3351 | 2121 |
| 3. | 3123 | 2021 |

EXAMPLE 3

Detection of *Mycobacterium Avium-Intracellulaire* (MAI) in Patient Samples

A recent paper (Boddinghaus et al., J. Clin. Microbiol. 28:175i, 1990) has reported successful identification of *Mycobacteria* species and differentiation among the species by amplification of 16S ribosomal RNAs (rRNAs). The advantages of using bacterial 16S rRNAs as targets for amplification and identification were provided by Rogall et al., J. Gen. Microbiol., 136:1915, 1990 as follows: 1) rRNA is an essential constituent of bacterial ribosomes; 2) comparative analysis of rRNA sequences reveals some stretches of highly conserved sequences and other stretches having a considerable amount of variability; 3) rRNA is present in large copy numbers, i.e. $10^3$ to $10^4$ molecules per cell, thus facilitating the development of sensitive detection assays; 4) the nucleotide sequence of 16S rRNA can be rapidly determined without any cloning procedures and the sequence of most Mycobacterial 16S rRNAs are known.

Three pairs of Capture/Amp-probe-1 and Amp-probe-2 probes are prepared by automated oligonucleotide synthesis (as above), based on the 16S rRNA sequences published by Boddinghaus et al., and Rogall et al. The first pair of probes (MYC) is generic in that the specific portions of the first and second probes are hybridizable to 16S RNA of all *Mycobacteria* spp; this is used to detect the presence of any mycobacteria in the specimen. The second pair of probes (MAV) is specific for the 16S rRNA of *M. avium*, and the third pair of probes (MIN) is specific for the 16S rRNA of *M intracellulaire*. The extremely specific ligation reaction of the present method allows the differentiation of these two species at a single nucleotide level.

A. The probes that may be used for generic detection of all *Mycobacter* spp. comprise a first and second probe as in Example 1. The first probe is a 3' biotinylated-Capture/Amp-probe-1 (MYC), an oligodeoxyribonucleotide of 54 nucleotides in length with the following sequence (also listed below as SEQ ID NO: 7):

```
        1         11         21         31
5'-CAGGCTTATC CCGAAGTGCC TGGTAACAGG ATTTCCCCGG 41         51
   GAATTCAAGC TTGG-3'
```

Nucleotides 1-18, at the 5' end of the probe are complementary to a common portion of Mycobacterial 16S rRNA, i.e., a 16S rRNA sequence which is present in all *Mycobacteria* spp. The 3' portion of the probe, comprising nucleotides 19-54 is identical in sequence to the 36 nucleotides comprising the generic portion of Capture/Amp-probe-1 (HIV) of Example 1.

The second probe is Amp-probe-2 (MYC), an oligodeoxyribonucleotide of 91 nucleotides in length, with the following sequence (also listed below as SEQ ID NO. 8):

```
        1         11         21         31
5'-GGGTTGACCC GGCTAGATCC GGGTGTGTCC TCTCTAACTT 41         51         61         71
   TCGAGTAGAG AGGTGAGAAA ACCCCGTTAT CCGGTATTAG 81         91
   ACCCAGTTTC C-3'
```

Nucleotides 71-91 at the 3' end of the probe are complementary to a common portion of 16S rRNA adjacent the region complementary to nucleotides 1-18 or Capture/Amp-probe-1 (MYC) disclosed above, common to all *Mycobacteria* spp. Nucleotides 1-70 at the 5' end of the probe comprise the same generic sequence set forth for Amp-probe-2 (HIV) in Example 1.

End to end ligation of the two probes, as in Example 1, provides ligated amplification sequence (MYC), 145 nucleotides in length, for detection of all *Mycobacteria* spp., having the following sequence (also listed below as SEQ ID NO. 9):

```
        1         11         21         31
5'-GGGTTGACCC GGCTAGATCC GGGTGTGTCC TCTCTAACTT 41         51         61         71
   TCGAGTAGAG AGGTGAGAAA ACCCCGTTAT CCGGTATTAG 81         91        101        111
   ACCCAGTTTC CCAGGCTTAT CCCGAAGTGC CTGGTAACAG 121        131        141
   GATTTCCCCG GGAATTCAAG CTTGG-3'
```

B. The pair of probes for specific detection of *M. avium* are as follows:

The first probe is a 3' biotinylated-Capture/Amp-probe-1 (MAV), an oligodeoxyribonucleotide of 56 nucleotides in length with the following sequence (also listed below as SEQ ID NO. 10):

```
        1         11         21         31
5'-GAAGACATGC ATCCCGTGGT CCTGGTAACA GGATTTCCCC 41         51
   GGGAATTCAA GCTTGG-3'
```

Nucleotides 1-20 at the 5'-end are complementary to a portion of 16S rRNA specific for *M. avium*. Nucleotides 21-56 comprise the same generic sequence, as above.

The second probe is Amp-probe-2 (MAV), an oligodeoxyribonucleotide of 90 nucleotides in length, with the following sequence (also listed below as SEQ ID NO. 11):

```
        1         11         21         31
5'-GGGTTGACCC GGCTAGATCC GGGTGTGTCC TCTCTAACTT 41         51         61         71
   TCGAGTAGAG AGGTGAGAAA ACCCCGTTAT CGCTAAAGCG

81
   CTTTCCACCA-3'
```

Nucleotides 71-90 at the 3' end of the probe comprise the specific nucleotide sequence complementary to a region of 16S rRNA specific for *M. avium*, adjacent the specific sequence recognized by Capture/Amp-probe-1 (MAV). Nucleotides 1-70 comprise the same generic sequence as above.

End to end ligation of the two probes provides a 146 nucleotide long ligated amplification sequence (MAV) for detection of *M. avium* having the following sequence (also listed below as SEQ ID NO. 12):

```
      1         11         21         31
5'-GGGTTGACCC GGCTAGATCC GGGTGTGTCC TCTCTAACTT 41         51         61         71
   TCGAGTAGAG AGGTGAGAAA ACCCCGTTAT CGCTAAAGCG 81         91        101        111
   CTTTCCACCA GAAGACATGC ATCCCGTGGT CCTGGTAACA 121        131        141
   GGATTTCCCC GGGAATTCAA GCTTGG-3'
```

C. The pair of probes for specific detection of *M. intracellulaire* are as follows:

The first probe is a 3'-biotinylated Capture/Amp-probe-1 (MIN), an oligonucleotide of 56 nucleotides in length with the following sequence (also listed below as SEQ ID NO. 13):

```
      1         11         21         31
5'-AAAGACATGC ATCCCGTGGT CCTGGTAACA GGATTTCCCC 41         51
   GGGAATTCAA GCTTGG-3'
```

Nucleotides 1-20 at the 5' end are complementary to a portion of 16S rRNA specific for *M. intracellulaire*. Nucleotides 21-56 comprise the same generic sequence as above.

The second probe is Amp-probe-2 (MIN), an oligodeoxyribonucleotide or 90 nucleotides in length, with the following sequence (also listed below as SEQ ID NO. 14):

```
      1         11         21         31
5'-GGGTTGACCC GGCTAGATCC GGGTGTGTCC TCTCTAACTT 41         51         61         71
   TCGAGTAGAG AGGTGAGAAA ACCCCGTTAT CGCTAAAGCG

81
   CTTTCCACCT-3'
```

Nucleotides 71-90 at the 3' end of the probe comprise the specific nucleotide sequence complementary to a region of *M. intracellulaire* 16S rRNA adjacent the specific sequence recognized by Capture/Amp-probe-1 (MIN).

End to end ligation of the two probes provides a 146 nucleotide long ligated amplification sequence (MIN) for detection of *M. intracellulaire*, having the following sequence (also listed below as SEQ ID NO. 15):

```
      1         11         21         31
5'-GGGTTGACCC GGCTAGATCC GGGTGTGTCC TCTCTAACTT 41         51         61         71
   TCGAGTAGAG AGGTGAGAAA ACCCCGTTAT CGCTAAAGCG 81         91        101        111
   CTTTCCACCT AAAGACATGC ATCCCGTGGT CCTGGTAACA 121        131        141
   GGATTTCCCC GGGAATTCAA GCTTGG-3'
```

D. In order to detect the presence of the above *Mycobacteria* spp., patients' blood specimens are collected in Pediatric Isolator Tubes (Wampole Laboratories, NJ). The Isolator's lysis centrifugation technique enables separation of blood components, followed by lysis of leukocytes to improve recovery of intracellular organisms (Shanson et al., J. Clin. Pathol. 41:687, 1988). After lysis, about 120 p.l of concentrated material is dissolved in an equal volume of the 5M GnSCN buffer of Example 1. The mixture is boiled for 30 minutes, which because of the nature of mycobacterial cell walls, is required for lysis of *Mycobacteria* spp. The subsequent procedures (i.e., capture, ligation, PCR and detection) are the same as those employed in Example 1.

Before the PCR amplification, a direct detection is made by measuring radioactivity representing $^{32}$P-5'-AMP-probe-2 captured on the magnetic beads. After the unbound radioactively-labeled Amp-probe-2 is removed by extensive washing, the target 16S rRNA molecules that are present in concentrations of more than $10^6$/reaction is detectable. Target 16S rRNA that cannot be detected directly is subjected to PCR amplification of the ligated amplification sequences as per Example 1. The primers for use in amplification are the same two generic primers of Example 1 (SEQ ID NOS. 5 and 6).

EXAMPLE 4

Detection of HCV RNA in a Sample

Hepatitis C virus (HCV), an RINA virus, is a causative agent of post transfusion hepatitis. HCV has been found to be distantly related to flavivirus and pestivirus and thus its genome has a 5' and a 3' untranslated region (UTR) and encodes a single large open reading frame (Lee et al., J. Clin. Microbiol. 30:1602-1604, 1992). The present method is useful for detecting the presence of HCV in a sample.

A pair of oligodeoxynucleotide probes, designated Capture/Amp-probe-1 (HCV) and Amp-probe-2 (HCV), respectively, for targeting the 5' UTR of HCV RNA are prepared as in Example 1.

Capture/Amp-probe-i (HCV), which is biotinylated at the 3' end, is a 55 nucleotide long oligodeoxyribonucleotide having the following nucleotide sequence (also listed below as SEQ ID NO. 16):

```
      1         11         21         31
5'-GCAGACCACT ATGGCTCTCC CTGGTAACAG GATTTCCCCG 41         51
   GGAATTCAAG CTTGG -3'
```

Nucleotides 1-19 at the 5' end of Capture/Amp-probe-1 (HCV) comprise a specific sequence complementary to a portion of the 5' UTR of the HCV genome. Nucleotides 20-55 at the 3' end of the probe comprise the same 36 nucleotide generic sequence as in Capture/Amp-probe-1 (HIV) of Example 1.

Amp-probe-2 (HCV) is a 90 nucleotide long oligodeoxyribonucleotide having the following nucleotide sequence (also listed below as SEQ ID NO. 17):

```
      1         11         21         31
5'-GGGTTGACCC GGCTAGATCC GGGTGTGTCC TCTCTAACTT 41         51         61         71
   TCGAGTAGAG AGGTGAGAAA ACCCCGTTAT CCGGTGTACT

81
   CACCGGTTCC-3'
```

Nucleotides 71-90 comprise the 3' specific portion of the probe, complementary and hybridizable to a portion of the HCV 5' UTR immediately adjacent to the portion of the HCV genome hybridizable to nucleotides 1-19 of Capture/Amp-probe-2 (HCV). Nucleotides 1-70 comprise the same generic sequence as in Amp-probe-2 (HIV) of Example 1.

End to end ligation of the two probes as in Example 1 provides a 145 nucleotide long ligated amplification sequence (HCV) for detection of HCV in a sample, having the sequence (also listed below as SEQ ID NO. 18):

```
        1          11          21          31
5'-GGGTTGACCC GGCTAGATCC GGGTGTGTCC TCTCTAACTT 41          51          61          71
   TCGAGTAGAG AGGTGAGAAA ACCCCGTTAT CCGGTGTACT 81          91         101         111
   CACCGGTTCC GCAGACCACT ATGGCTCTCC CTGGTAACAG 121         131         141
   GATTTCCCCG GGAATTCAAG CTTGG-3'
```

The ligated amplification sequence (HCV) is amplified using a two temperature PCR reaction as in Example 1. The PCR primers used for amplification are the same two generic primers (SEQ ID NOS. 5 and 6) of Example 1.

EXAMPLE 5

Use of Multiple Capture and Amplification Probes to Detect HCV RNA in a Sample

A pair of amplication probes and two capture/amplification probes were used to assay for and detect HCV RNA in a sample, thereby increasing the capture efficiency of the assay.

The capture/amplification probes Capture/Amp-probe-1 (HCV A) (all oligomers described in this Example are designated "(HCV A)" to distinguish from the probes "(HCV)" of Example 4) having SEQ ID NO. 22 and Capture/Amp-probe-1A (HCV A) having SEQ ID NO. 23 are designed and synthesized such that their 5' termini are biotinylated and the 3' region of the probes comprises sequences complementary to and hybridizable with sequences in the 5'UTR of HCV RNA (FIG. 4). The generic nucleotide sequence at the 5' region of the probes that are not hybridizable to the target nucleic acid sequence are designed and synthesized to have random sequences and a GC content of, at least, 60%, and such that they exhibit minimal secondary structure e.g. hairpin or foldback structures.

Capture/Amp-probe-1 (HCV A) which is biotinylated at the 5' terminus, is a 45 nucleotide DNA oligomer, such that nucleotides 5 to 45 in the 3' region, are complementary to and hybridizable with sequences in the 5'UTR of the target HCV RNA, and that the oligomer has the following nucleotide sequence (also listed below as SEQ ID NO. 22):

5'-AAGAGCGTGA AGACAGTAGT TCCTCACAGG GGAGTGATTC ATGGT-3'

Capture/Amp-probe-iA (HCV A) which is also biotinylated at the 5' terminus, is also a 45 nucleotide DNA oligomer, such that nucleotides 5 to 45 in the 3' region are complementary to and hybridizable with sequences in the 5'UTR of HCV RNA that are immediately adjacent to the region of the 5'UTR of the HCV RNA hybridizable with Capture/Amp-probe-1 (HCV A) and such that the oligomer has the following nucleotide sequence (also listed below as SEQ ID NO. 23):

5'-AAGACCCAAC ACTACTCGGC TAGCAGTCTT GCGGGGGCAC GCCCA-3'

The two amplification probes Amp-probe-2 (HCV A) and Amp-probe-2A (HCV A) each contain a nucleotide sequence complementary to and hybridizable with the conserved 5'UTR of HCV RNA.

Amp-probe-2 (HCV A) is a 51 nucleotide oligomer such that nucleotides 1 to 30 in the 5' region are complementary to and hybridizable with sequences in the 5'UTR of HCV RNA, and that the nucleotides 34 to 51 at the 3' terminus bind to and hybridize with PCR primer-3 and such that the oligomer has the following nucleotide sequence (also listed below as SEQ ID NO. 24):

5'-ACTCACCGGT TCCGCAGACC ACTATGGCTC GTTGTCTGTG TATCTGCTAA-3'

Amp-probe-2A (HCV A) is a 69 nucleotide oligomer such that nucleotides 40 to 69 in the 3' region are complementary to and hybridizable with sequences in the 5'UTR of HCV RNA genome immediately adjacent to the portion of the HVC RNA genome hybridizable to nucleotides 1-30 of Amp-probe-2 (HCV A) and such that the nucleotides 1 to 18 at the 5' terminus bind to and hybridize with PCR primer-4 and such that nucleotides 19 to 36 at the 5' terminus bind to and hybridize with PCR primer-5, and such that the oligomer has the following nucleotide sequence (also listed below as SEQ ID NO. 25):

5'-CAAGAGCAAC TACACGAATT CTCGATTAGG TTACTGCAGA GGACCCGGTC GTCCTGGCAA TTCCGGTGT-3'

End to end ligation of the two probes provides a 120 nucleotide ligated product, the ligation-amplification sequence (HCV A) that serves as a detectable sequence for HCV as well as a template for amplification reactions, and has the sequence (also listed below as SEQ ID NO. 26):

5'-CAAGAGCAAC TACACGAATT CTCGATTAGG TTACTGCAGA GGACCCGGTC GTCCTGGCAA TTCCGGTGTA CTCACCGGTT CCGCAGACCA CTATGGCTCG TTGTCTGTGT ATCTGCTAAC-3'

Primer-3, used for the first series of PCR amplification of the ligated amplification sequence, SEQ ID NO. 26 (HCV A), and which has a length of 18 nucleotides, is complementary to sequence comprising nucleotides 34 to 51 at the 3' terminus of Amp-probe-2 (HCV A), and is, therefore, also complementary to the sequence comprising nucleotides 103 to 120 of the ligated amplification sequence, SEQ ID NO. 26 (HCV A), and has the sequence (also listed below as SEQ ID NO. 27):

5'-GTTAGCAGAT ACACAGAC-3'

Primer-4, used for the first series of PCR amplification of the ligated amplification sequence (HCV A), SEQ ID NO. 26, and which has a length of 18 nucleotides, is complementary to the sequence comprising nucleotides 1-18 at the 5' terminus of the Amp-probe-2A (HCV A), and is, therefore, also complementary to the sequence comprising nucleotides 1 to 18 of the ligated amplification sequence, SEQ ID NO. 26 (HCV A), and has the sequence (also listed below as SEQ ID NO. 28):

5'-CAAGAGCAAC TACACGAA-3'

Primer-5, a DNA oligomer of 18 nucleotides is used for the second series of PCR amplification of the ligated amplification sequence (HCV A), SEQ ID NO. 26, such that the primer is complementary to the sequence comprising nucleotides 19-36 of the Amp-probe-2A (HCV A), and is, therefore, also hybridizable to the sequence comprising nucleotides 19-36 of the ligated amplification sequence SEQ ID NO. 26 (HCV A), and has the sequence (also listed below as SEQ ID NO. 29):

5'-TTCTCGATTA GGTTACTG-3'

The assay utilizing the above probes and primers was used to detect HCV RNA in 24 human serum samples that were stored at −70° C. until use. For the assay, 180 µl serum sample was added to concentrated lysis buffer (prepared by condensing 250 µl of the lysis solution containing 5M GnSCN, 0.5% bovine serum albumin, 80 mM EDTA, 400 mM Tris HCl (pH 7.5), and 0.5% Nonidet P-40 so that the mixture of serum and lysis buffer would have a final concentration of 5M GnSCN) mixed well and incubated for 1 hour at 37° C. to release the target RNA from HCV particles. 80 µl of the lysis mixture was then transferred to 120 µl of hybridization buffer [0.5% bovine serum albumin, 80 mM EDTA, 400 mM Tris-HCl (pH 7.5), 0.5% Nonidet-P40] with $10^{10}$ molecules each of amplification probes, Amp-probe-2 (HCV A) and Amp-probe-2A (HCV A) oligomers, and $10^{11}$ molecules each of capture/amplification probes, Capture/Amp-probe-1A (HCV A) and Capture/Amp-probe-1A (HCV A). The addition of the hybridization buffer reduced the concentration of the guanidium isothiocyanate (GnSCN) from 5M to 2M to allow the hybridization to occur. The mixture was incubated at 37° C. for 1 hour to let the various probes hybridize with the target RNA, whereupon 30 µl of streptavidin-coated paramagnetic beads (Promega) were added to the hybridization mixture before incubation at 37° C. for 20 minutes to allow ligand binding. Next, the beads were washed with 150 µl of 2M GnSCN to eliminate any free probes, proteins, extraneous nucleic acids and potential PCR inhibitors from the hybridization mixture; this was followed by the removal of the GnSCN by washing twice with 150 µl ligase buffer [66 mM Tris-HCl (pH 7.5) 1 mM DTT, 1 mM ATP, 0.5% Nonidet P-40 and 1 mM MnCl$_2$]. At each wash-step, the magnetic separation of the bound complex from the supernatant was effected by the magnetic field technique described in Example 1.

The amplification probes, Amp-probe-2 (HCV A) and Amp-probe-2A (HCV A), bound to target RNA were then covalently joined to create the ligated amplification sequence (HCV A) that was utilized as a template for PCR amplification. The hybrid complex was resuspended in 20 µl ligase buffer with 5 units of T$_4$ DNA ligase (Boehringer) and incubated for 1 hour at 37° C. for the ligation reaction. For the subsequent PCR reaction referred to hereafter as the "first PCR reaction", 10 µl of the ligated mixture, including the beads, was added to 20 µl of PCR mixture [0.06 µ.M each of Primer-3 and Primer-4, 1.5 Units Taq DNA Polymerase, 0.2 mM each of dATP, dCTP, dGTP and dTTP, 1.5 mM MgCl$_2$, 10 mM Tris-HCl (pH 8.3) 50 mM KCl] and the mixture incubated at 95° C. for 30 seconds, 55° C. for 30 seconds and 72° C. for 1 minute, for 35 cycles. After the first PCR reaction, 5 µl of the product was transferred to a second PCR mixture [same components as the first PCR mixture except that Primer-4 was substituted with Primer-5] for "the second PCR reaction" (a semi-nested PCR approach to increase the sensitivity of the assay) carried out under the same conditions as the first PCR reaction. 10 µl of the products of the second reaction were electrophoresed on a 6% polyacrylamide gel, stained with ethidium bromide and visualized under ultraviolet light.

To establish the sensitivity and the specificity of the method, 10-fold serial dilutions of synthetic HCV RNA in HCV-negative serum were assayed according to the protocol described above, so that the concentration of HCV RNA ranged from 10 to $10^7$ molecules/reaction. After ligation and amplification, the PCR products were separated by polyacrylamide gel electrophoresis, stained with ethidium bromide and visualized under ultra violet light. The results, shown in FIG. 8, clearly indicate the specificity of the method. In the absence of HCV RNA there is no signal, indicating that probes must capture the target RNA in order to generate a PCR product. As few as 100 molecules of HCV RNA/sample were detectable with the semi-nested PCR method (FIG. 8), indicating that the sensitivity of the method is at least comparable to that of conventional RT-PCR (Clementi et al., 1993, PCR 2: 191-196).

Figure 8:
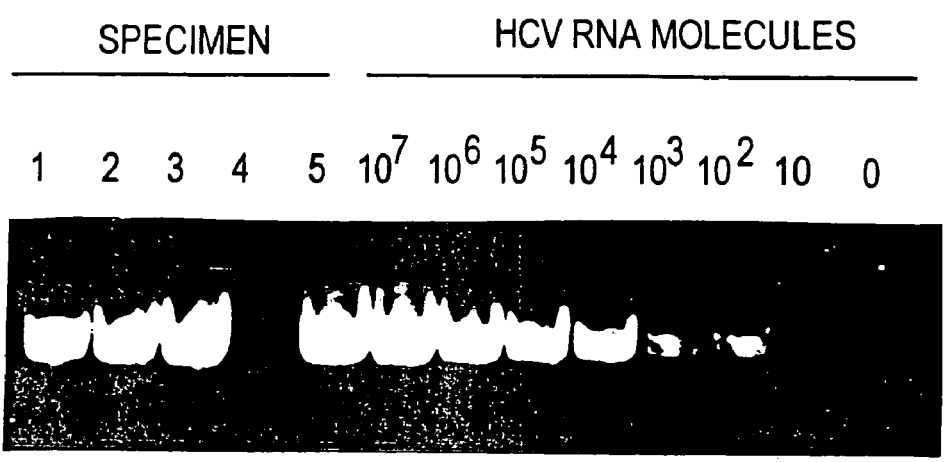
FIG. 8 is a photograph of ethidium bromide stained DNA depicting PCR amplified probes used to detect HCV RNA in a sample. The amount of HCV RNA in the sample is determined by comparing sample band densities to those of standard serial dilutions of HCV transcripts.

Further, relative amounts of the PCR product represented by the intensity of the bands as visualized in FIG. 8, were proportional to the quantity of the target RNA (HCV RNA transcripts). Therefore, the assay is quantitative over, at least, a range of $10^2$ to $10^5$ target molecules.

To determine the increased capture efficiency afforded by two capture probes, $^{32}$P-labeled target HCV RNA was assayed for capture and retention on paramagnetic beads using Capture/Amp-probe-1 (HCV A) or Capture/Amp-probe-1A (HCV A) or both. The capture was estimated by the amount of radioactivity retained on the paramagnetic beads after extensive washes with 2M-GnSCN buffer and the ligase buffer. Results showed that 25.7% of labeled HCV RNA was retained on the beads when captured by Capture/Amp-probe-1 (HCV A) alone, 35.8% retained with Capture/Amp-probe-1A (HCV A) alone and 41.5% of the target RNA was retained when both the capture probes were used. Therefore the double-capture method was more efficient than the use of a single capture probe.

EXAMPLE 6

Use of Multiple Capture and Amplification Probes to Detect HIV-1 RNA in a Sample An alternative approach to that set forth in Example 1 uses a capture/amplification probe and a pair of amplication probes to detect the presence of HIV-1 RNA. Capture/Amp-probe-1 (HIV), SEQ ID NO. 1 and a pair of amplification probes Amp-probe-2 (HIV A) (all oligomers described in this Example are designated "(HIV A)" to distinguish from the probes "(HIV)" of Example 1) (SEQ ID NO. 19) and Amp-probe-2A (HIV A), (SEQ ID NO. 20), are utilized such that the generic nucleotide sequences of the ligated amplification sequence (HIV A) (SEQ ID NO. 21) comprising nucleotides 1-26 derived from nucleotides 1-26 of Amp-probe-2 (HIV A) and nucleotides 86-112 derived from nucleotides 40-65 of Amp-probe-2A (HIV A) are designed and synthesized to have random sequences and a GC content of, at least, 60%, and such that they exhibit minimal secondary structure e.g. hairpin or foldback structures.

Amplification probe Amp-probe-2 (HIV A) is a 47 nucleotide DNA oligomer such that nucleotides 27 to 47 in the 3' region, are complementary to and hybridizable with sequences in the gag region of the target HIV-1 RNA, and that the oligomer has the following nucleotide sequence (also listed below as SEQ ID NO. 19):

5'-GGTGAAATTG CTGCCATTGT CTGTATGTTG TCTGTGTATC

TGCTAAC-3'

Amplification probe Amp-probe-2A (HIV A) is a 65 nucleotide DNA oligomer such that nucleotides 1 to 39 in the 5' region, are complementary to and hybridizable with sequences in the gag region of the target HP/-1 RNA, immediately adjacent to the portion of the HP/-1 RNA genome hybridizable to nucleotides 27-47 of the Amp-probe-2 (HIV A) and that the oligomer has the following nucleotide sequence (also listed below as SEQ ID NO. 20):

5'-CAAGAGCAAC TACACGAATT CTCGATTAGG TTACTGCAGC

AACAGGCGGC CTTAACTGTA GTACT-3'

End to end ligation of the two amplification probes provides a 112 nucleotide ligated amplification sequence (HIV A) such that the sequence serves as a detectable sequence for HP/-1 RNA as well as a template for amplification reactions, and has the following sequence (also known as SEQ ID NO. 21)

5'-GGTGAAATTG CTGCCATTGT CTGTATGTTG TCTGTGTATC

TGCTAACCAA GAGCAACTAC ACGAATTCTC GATTAGGTTA

CTGCAGCAAC AGGCGGCCTT AACTGTAGTA CT-3'

Further, the capture, detection and optional amplification of the captured ligation product in order to assay for HIV RNA is carried out as described in Example 5. The PCR primers used for amplification are the same primers-3, 4 and 5 (SEQ ID NOS. 27, 28 and 29) of Example 5.

EXAMPLE 7

Use of Separate Capture/Amplification Probes and a Ligation Independent, Single Amplification Probe to Detect HCV RNA in a Sample The assay employs a single ligation independent amplification probe and two capture/amplification probes to detect HCV RNA in a sample.

The capture/amplification probes Capture/Amp-probe-1 (HCV A) and Capture/Amp-probe-1A (HCV A) used in this method are the same as described in Example 5.

The amplification probe, Amp-probe-2 (HCV B) (all oligomers described in this Example are designated "(HCV B)" to distinguish from the probes "(HCV)" of Example 4), SEQ ID NO. 30, is a 100 nucleotide DNA molecule such that the sequence represented by nucleotides 39 to 79 in the central region of the oligomer is complementary to and hybridizable to a region in the 5' UTR of the HCV RNA (FIG. 6), and that the sequences spanning nucleotides 1-38 in the 5' terminus and by nucleotides 80-100 in the 3' terminus are designed and synthesized such that they have random sequences and a GC content of, at least, 60%, and such that they exhibit minimal secondary structure e.g. hairpin or foldback structures. Amp-probe-2 (HCV B), also referred to as amplification sequence, has the following sequence (also listed below as SEQ ID NO. 30):

5'-CAAGAGCAAC TACACGAATT CTCGATTAGG TTACTGCAGC

GTCCTGGCAA TTCCGGTGTA CTCACCGGTT CCGCAGACCG

TTGTCTGTGT ATCTGCTAAC-3'

The capture, detection and the optional amplification of the probe sequences was carried out as described in Example 5, except that primers-3 and -4, only, were utilized in a single PCR amplification step, the second PCR step was omitted, and that the ligation step was omitted.

EXAMPLE 8

Use of Separate Capture/Amplification Probes and a Simgle, Amplifiable, Ligation Dependent Probe to Detect HCV RNA in a Sample The method in this Example employs the two capture/amplification probes Capture/Amp-probe-1 (HCV A) and Capture/Amp-probe-1A (HCV A) described in Example 5 and a single amplification probe, Amp-probe-2 (HCV C) (all oligomers described in this Example are designated "(HCV C)" to distinguish from the probes "(HCV)" of Example 4) that hybridizes to the target nucleic acid and circularizes upon ligation of its free termini as shown in FIG. 7.

Amp-probe-2 (HCV C) is a 108 nucleotide amplification probe, also referred to as an amplification sequence, such that nucleotides 1-26 in the 5' terminus of the oligomer are complementary to and hybridizable to a sequence in the 5'UTR of the target HCV RNA (indicated by (a) in FIG. 7) and such that nucleotides 83-108 at the 3' terminus of the oligomer are complementary to and hybridizable to a sequence in the 5'UTR of the target HCV RNA (indicated by (b) in FIG. 7). Moreover, when the probe hybridizes with the target HCV RNA, the 3' and 5' termini of the probe are placed immediately adjacent to each other (FIG. 7), resulting in the formation of a closed circular molecule upon ligation with a linking agent, such as DNA ligase. The sequence of Ampprobe-2 (HCV C) is given as follows (also listed as SEQ ID NO. 31):

5'-CCTTTCGCGA CCCAACACTA CTCGGCTGTC TGTGTATCTG

CTAACCAAGA GCAACTACAC GAATTCTCGA TTAGGTTACT

GCGCACCCTA TCAGGCAGTA CCACAAGG-3'

Primer-3 (SEQ ID NO. 27), used for the first series of PCR amplification of the ligated and circularized Amp-probe-2 (HCV C), is an 18 nucleotide long oligomer that is complementary to the sequence comprising nucleotides 27 to 45 of Amp-probe-2 (HCV C).

Primer-4 (SEQ ID NO. 28), also used for the first series of PCR amplification of the ligated and circularized Amp-probe-2, is a 18 nucleotide long oligomer that is complementary to the sequence comprising nucleotides 46 to 63 of Ampprobe-2 (HCV C).

The hybridization of the two capture/amplification probes and the amplification probe to target HCV RNA, circularization of the amplification probe upon ligation of its termini and amplification of the probe sequences was carried out as described in Example 5, except that primers-3 and 4, only, were utilized in a single PCR amplification step, the second PCR step was omitted, and that Amp-probe-2 (HCV C) (SEQ ID NO. 31) was substituted for the pair of amplification probes, Amp-probe-2 (HCV A) (SEQ ID NO. 24) and Amp-probe-2A (HCV A) (SEQ ID NO. 25) utilized in Example 5.

To establish the sensitivity and the specificity of the method, 10-fold serial dilutions of synthetic HCV RNA in HCV-negative serum were assayed according to the method to provide standard concentrations of HCV RNA ranging from $10^3$ to $10^7$ molecules/sample. After ligation and amplification, the PCR products were separated by polyacrylamide gel electrophoresis, stained with ethidium bromide and visualized under ultra-violet light.

The results, (FIG. 9, (−): control, no sample), indicate the specificity of the method. The assay is highly specific; in the absence of target HCV RNA there is no visible signal, indicating that probes must capture the target RNA in order to generate a PCR product. As seen in FIG. 9, as few as $10^4$ molecules of HCV RNA/sample were clearly detectable.

Further, relative amounts of the PCR product, represented by the intensity of the bands (FIG. 9), were proportional to the quantity of the target RNA (HCV RNA transcripts). Therefore, the assay is significantly quantitative at least over a range of $10^4$ to $10^7$ target molecules.

EXAMPLE 9

Detection of HCV Target Sequences in Tissue Sample Using LD-PCR Assay

This example provides a comparison of the ligation-dependent PCR (LD-PCR) of the present invention with reverse transcriptase PCR (RT-PCR) for the detection of HCV sequences in formalin fixed, paraffin embedded (FFPE) liver samples. Twenty-one archival liver specimens of hepatocellular carcinoma (HCCs) from patients who underwent liver resection or orthotopic liver transplantation between January, 1992 to March, 1995 at the Mount Sinai Medical Center, New York, N.Y. were selected for this study. Thirteen of these patients were anti-HCV positive and eight were negative as determined by a second generation enzyme-linked immunoassay (EIA II) (Abbott Diagnostic, Chicago, Ill). An explanted liver tissue from an anti-HCV negative patient with cirrhosis secondary to biliary atresia was used as control. After surgery, the liver specimens were stored at 4° C. and sectioned within twelve hours. The specimens were fixed in 10% buffered formalin for eight to twelve hours and routinely embedded in paraffin. The FFPE specimens were stored at room temperature for a period of three months up to three years. In addition, snap frozen liver tissues from thirteen of the twenty-two patients, stored at −70° C., were used to resolve discordance between LD-PCR and RT-PCR results.

FFPE specimens (approximately 2-4 cm$^2$) were sectioned on a microtome with a disposable blade to 10 µm in thickness, and each section was placed in a 1.5-ml microcentrifuge tube. To avoid cross contamination, the blades were changed and the holder was cleaned with 10% Chlorox solution between each sample. The sections were deparaffinized by incubating at 60° C. for 10 minutes in the presence of 1 ml of xylene (Sigma). The xylene was removed by two washes with absolute ethanol. The specimens were then dried by vacuum centrifugation or by placing on a hot block at 65° C. for 30 min.

For LD-PCR, the deparaffinized tissues were lysed by incubating at 100° C. for 30 min in 250 µl of lysis buffer containing 5 M guanidinium thiocyanate (GnSCN) (Fluka), 0.5% bovine serum albumin (Sigma), 80 mM EDTA, 400 mM Tris HCl (pH 7.5), and 0.5% sodium-N-lauroylsarcosine (Sigma) followed by incubating at 65° C. for 30 min. The lysed specimens were stored at −20° C. until use. The HCV serologic status of all specimens was blinded to laboratory personnel to avoid bias.

For RT-PCR, the deparaffinized tissues were lysed by incubating at 60° C. for 5 hr in 200 µl of lysis buffer containing 10 mM Tris-HCl (pH 8.0), 0.1 mM EDTA (ph 8.0), 2% sodium dodecyl sulfate and 500 µg/ml proteinase K. RNA was purified by phenol and chloroform extractions followed by precipitation with an equal volume of isopropanol in the presence of 0.1 volume of 3 M sodium acetate. The RNA pellet was washed once in 70% ethanol, dried and resuspended in 30 µl of sterile diethylpyrocarbonate-treated water. RNA was also extracted from sections (10 nm thickness) of frozen liver tissue obtained from the corresponding patients using the single step RNA extraction method described by Chomczynski et al. (1987) *Anal. Biochem.* 162: 156.

LD-PCR was performed as follows. Briefly, 80 µl of lysis mixture were added to 120 µl of hybridization buffer [0.5% bovine serum albumin, 80 mM EDTA, 400 Mm Tris-HCl (pH 7.5), and 0.5% sodium-N-lauroylsarcosine], which contained $10^{10}$ molecules of phosphorylated Amp-probe-2, $10^{10}$ molecules of Amp-probe 2A and $10^{11}$ molecules of capture Amp-probe 1 and capture Amp probe 1A. (Probes are as described in Example 5). Addition of the hybridization buffer reduced the GnSCN concentration from 5 M to 2 M to allow hybridization to occur. This mixture was incubated for one hour to allow the formation of hybrids, consisting of two DNA capture probes and two DNA hemiprobes bound to their HCV RNA target. Thirty µl of streptavidin-coated paramagnetic beads (Promega) were added to the mixture and incubated at 37° C. for 20 min to allow the hybrids to bind to the bead surface. The beads were then washed twice with 150 µl of washing buffer [10 mM Tris-HCl (pH 7.5), 0.5% Nonidet P-40, and 1.5 mM MgCl$_2$, and 50 mM KCl] to remove nonhybridized probes, as well as GnSCN, proteins, nucleic acids, and any potential PCR inhibitors. During each wash, the beads were drawn to the wall of the assay tube by placing the tube on a Magnetic Separation Stand (Promega), enabling the supernatant to be removed by aspiration. The hybrids were then resuspended in 20 µl ligase solution [66 mM Tris HCl (pH 7.5), 1 mM dithiothreitol, 1 mM ATP, 1 mM MnCl$_2$, 5 mM MgCl$_2$, and 5 units of T4 DNA ligase (Boehringer Mannheim)] and incubated at 37° C. for one hour to covalently link the probes that are hybridized to adjacent positions on the RNA target, thus producing the ligated amplification probe described in Example 5. Ten µl of the ligation reaction mixture (including beads) were then transferred to 20 µl of a PCR mixture containing 0.66 µM of PCR primer 3 and 0.66 µM of PCR primer 4 as described in Examples, 1.5 units of Taq DNA polymerase, 0.2 mM dATP, 0.2 mM dCTP, 0.2 mM dGTP, 0.2 mM dTTP, 1.5 mM MgCl$_2$, 10 mM Tris-HCl (pH 8.3), and 50 mM KCl. The first PCR reaction was incubated at 90° C. for 30 sec, 55° C. for 30 sec and 72° C. for 1 min for 35 cycles in a GeneAmp PCR System 9600 Thermocycler (Perkin-Elmer, Norwalk, Conn.). After the first PCR, 5 µl of each reaction mixture were transferred into a 30-µl second PCR mixture containing the same components except that 0.66 µM of PCR primer 3 and 0.66 µM of PCR primer 5 were used for semi-nested PCR. The second PCR reaction was performed by the same protocol as the first PCR reaction. Ten µl of the second PCR reaction were analyzed by electrophoresis through a 6% polyacrylamide gel and visualized by ultraviolet fluorescence after staining with ethidium bromide. The presence of a 102 basepair band for the second PCR product was considered as a positive result. All tests were duplicated and done blindly to the serological status (anti-HCV positive or negative) of the sample.

RT-PCR was performed according to the method of Abe et al. (1994) *International Hepatology Communication* 2: 352. Briefly, 15 μl of RNA suspension of each specimen was used as template to detect HCV RNA and beta actin RNA. The beta actin RNA was used internal positive control for cellular RNA. The sequence of outer primers used for RT-PCR are, for HCV RNA, 5'-GCGACACTCCACCATA-GAT-3' (sense) (SEQ ID NO: 32) and 5'-GCTCATGGTG-CACGGTCTA-3' (antisense) (SEQ ID NO: 33) and for beta-actin RNA, 5'-CTTCTACAATGAGCTGCGTGTG-GCT-3' (sense) (SEQ ID NO: 34) and 5'-CGCTCATTGC-CAATGGTGATGACCT-3' (antisense) (SEQ ID NO: 35). The sequence of inner primers are, for HCV RNA, 5'-CT-GTGAGGAACTACTGTCT-3' (sense) (SEQ ID NO: 36) and 5'-ACTCGCAAGCACCCTATCA-3' (antisense) (SEQ ID NO: 37), and for beta-actin RNA, 5'-AAGGCCAAC-CGCGAGAAGAT-3' (sense) (SEQ ID NO: 38) and 5'-TCACGCACGATTTCCCGC-3' (antisense) (SEQ ID NO: 39). The first PCR reaction was combined with the reverse transcription step in the same tube containing 50 μl of reaction buffer prepared as follows: 20 units of Rnase inhibitor (Promega), 100 units of Moloney murine leukemia virus reverse transcriptase (Gibco BRL), 100 ng of each outer primer, 200 μM of each of the four deoxynucleotides, 1 unit of Taq DNA polymerae (Boehringer Maimheim) and 1×Taq buffer containing 1.5 mM $MgCl_2$. The thermocycler was programmed to first incubate the samples for 50 min at 37° C. for the initial reverse transcription step and then to carry out 35 cycles consisting of 94° C. for 1 min, 55° C. for 1 min, and 72° C. for 2 min. For the second PCR, 5 μl of the first PCR product was added to a tube containing the second set of each inner primer, deoxynucleotides, Taq DNA polymerase and Taq buffer as in the first PCR reaction, but without reverse transcriptase and Rnase inhibitor. The second PCR reaction was performed with the same protocol as the first PCR reaction but without the initial 50 min incubation at 37° C. Twenty μl of the PCR products were examined by electrophoresis through a 2% agarose gel. Positive results of HCV RNA and beta-actin RNA were indicated by the presence of second PCR products as a 268-basepair and a 307-basepair band, respectively.

The results of LD-PCR and RT-PCR are set forth below in Table 2.

TABLE 2

Comparison of LD-PCR with RT-PCR

| | FFPE[a] | | | | | Unfixed[b] |
|---|---|---|---|---|---|---|
| | LD-PCR[c] | | RT-PCR[d] | | | |
| HCV Serology (No) | + | − | + | − | + | − |
| | | | | | | RT-PCR[e] |
| Anti-HCV + (13) | 13 | 0 | 5 | 8 | 7[f] | 0 |
| Anti-HCV − (9) | 5 | 4 | 0 | 9 | 6[g] | 1 |

[a]FFPE - formalin fixed paraffin embedded liver tissues.
[b]Unfixed - snap frozen liver tissues of corresponding FFPE specimens.
[c]Number of FFPE specimens tested positive (+) or negative (−) by ligation-dependent PCR.
[d]Number of FFPE specimens tested positive (+) or negative (−) by reverse transcription PCR.
[e]Number of specimens confirmed by RT-PCR using unfixed frozen tissues.
[f]Only 7 unfixed specimens were available for confirmatory RT-PCR test.
[g]Only 7 unfixed specimens were available for confirmatory RT-PCR test.

Of the twenty-two FFPE specimens, thirteen were obtained from patients who were HCV positive by EIA assay and nine were HCV negative (Table 2). HCV RNA was detected in all thirteen seropositive FFPE specimens by LD-PCR, whereas only five were positive by RT-PCR. For confirmation, unfixed frozen liver specimens available from seven cases were tested by RT-PCR. Of these seven cases, HCV-RNA was detectable in all seven by LD-PCR when FFPE tissue of the same specimens were utilized, but in only one by RT-PCR. However, RT-PCR on the frozen tissue confirmed the presence of HCV-RNA in all cases. Beta actin mRNA was detected in all corresponding specimens, indicating minimal RNA degradation. These results confirmed the preservation of the HCV RNA during formalin-fixation, the heated paraffin embedding process, and up to three years of storage. The overall sensitivity of RT-PCR on FFPE specimens was 23.8% (5/21) in this study while it was determined 58.6% and 84% in prior studies by El-Batonony et al. (1994) *J. Med. Virol*. 43: 380 and Abe et al. The gross difference in these values was due to the difference in the selection of specimens in these studies (eight RT-PCR negatives and five positives on FFPE tissues were selected for this study). Among the eight HCV sero-negative liver specimens, seven with HCC were removed from two patients with primary biliary cirrhosis (PBC), two with alcoholic cirrhosis, two with hepatitis B virus (HBV) liver cirrhosis, one with cryptogenic liver cirrhosis and one without HCC from a child with biliary atresia (Table 3). Among the seven HCC liver specimens, five tested positive for HCV by LD-PCR, but none by RT-PCR. The specimen with biliary atresia remained negative by both PCR tests. To resolve this discrepancy, RT-PCR was performed on the seven unfixed frozen tissue specimens. The results are set forth below in Table 3.

TABLE 3

HCV RNA detected in HCV-seronegative cases

| Clinical Diagnosis (No)[a] | FFPE[b] | | Unfixed[c] | Total Confirmed |
|---|---|---|---|---|
| | LD-PCR[d] | RT-PCR[d] | RT-PCR[e] | Positive |
| PBC(2) | 1 | 0 | 2 | 2 |
| Alcoholic (2) | 2 | 0 | 2 | 2 |
| Biliary atresia (1) | 0 | 0 | N/D | 0 |
| HBV (3) | 2 | 0 | 2[g] | 2 |
| Cryptogenic (1) | 0 | 0 | 0 | 0 |

[a]Liver specimens from patients with various clinical diagnosis: PBC - primary biliary cirrhosis, Alcoholic - alcoholic liver cirrhosis, HBV - positive for HBsAg, Cryptogenic - cryptogenic liver cirrhosis.
[b]FFPE - formalin fixed paraffin embedded liver tissues.
[c]Unfixed - snap frozen, unfixed liver tissues of corresponding FFPE specimens.
[d]Number of FFPE specimens tested positive for HCV RNA by LD-PCR or RT-PCR.
[e]Number of specimens confirmed by RT-PCR using unfixed frozen tissues.
[g]Only 2 unfixed specimens were available for confirmatory RT-PCR test.
N/D: not done - no fresh frozen specimen available.

The RT-PCR results on unfixed tissue confirmed the LD-PCR results, indicating false negative results by serologic testing. In addition, one of the PBC specimens that tested negative by both LD-PCR and RT-PCR on FFPE specimens was positive by RT-PCR on an unfixed frozen specimen, indicating false negative results by both PCRs on the FFPE specimen. These results show that there is a high detection rate of HCV RNA in HCV seronegative HCC (6/8, 75%) (Table 3) and that the overall positive rate in both HCV seropositive and seronegative HCC specimens is 86% (18/21) (Table 2). Contamination was unlikely since the cutting of FFPE and unfixed specimens, and the PCR assays were performed in two separate laboratories. In addition, great precaution was taken in the specimen preparation and PCR testing with proper negative controls. The overall agreement between LD-PCR of FFPE specimens and RT-PCR on fresh frozen specimens is very high, and the sensitivity of LD-PCR is 95% (18/19).

The foregoing results suggest that crosslinks caused by formalin fixation disrupt chain elongation of the nascent DNA strand by reverse transcriptase, resulting in lower sensitivity of RT-PCR in FFPE tissue. In contrast, LD-PCR amplifies probe sequences, bypassing the step of primer extension along the cross-linked template. In addition, the amplification probes may only have a 30-nucleotide long complementary region, and therefore are more accessible to the non-crosslinked regions. LD-PCR can thus achieve a higher sensitivity in the detection of HCV RNA in FFPE specimens. The value of this sensitive assay is confirmed by the foregoing results, which evidence a high detection rate of HCV RNA even in seronegative specimens.

EXAMPLE 10

Primer Extension-Displacement on Circular Amplification Sequence

This example demonstrates the ability of Klenow fragment of DNA polymerase to displace downstream strands and produce a polymer.

Figure 18:
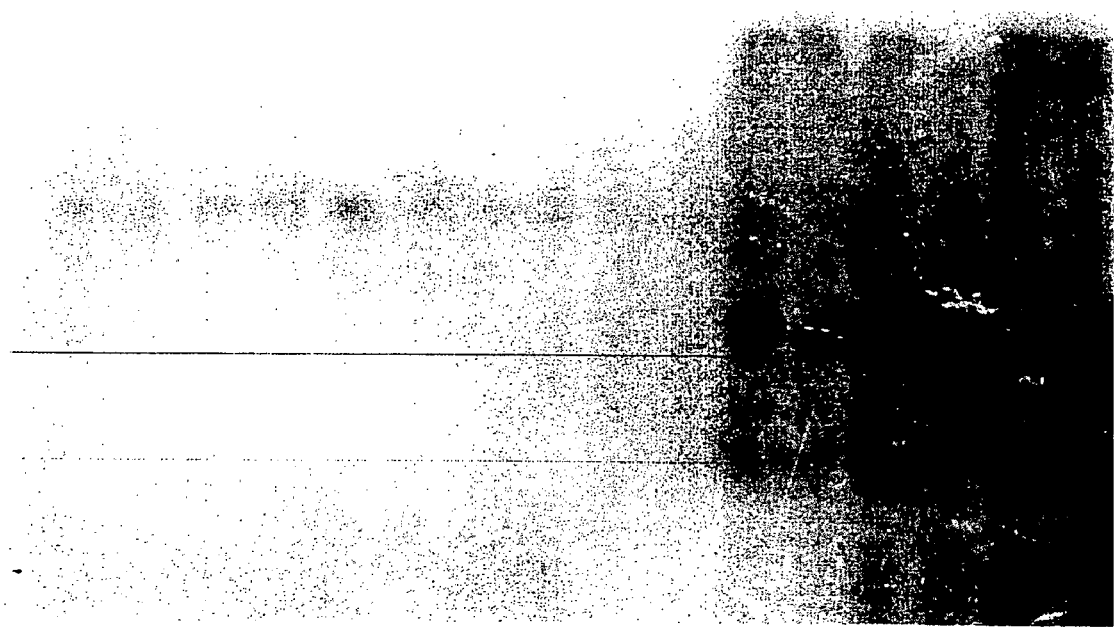
FIG. 18 provides a polyacrylamide gel depicting the amplification of a circular probe by extension of Ext-primer 1.

A synthetic DNA target was detected by mixing $10^{12}$ molecules of phosphorylated circularizable probe having SEQ ID NO:31 with $10^{13}$ molecules of synthetic HCV DNA target in 10 μl of 1× ligation buffer, heating at 65° C. for two minutes, and cooling to room temperature for ten minutes. One μl of ligase was added to the mix and incubated at 37° C. for one hour, followed by addition of $10^{13}$ molecules of $^{32}$P-labeled Ext-primer having SEQ ID NO:27. The mixture was heated to 100° C. for five minutes and then cooled to room temperature for twenty minutes. Forty μl of Klenow mix and dNTPs were added to the reaction and incubated at 37° C. Ten μl aliquots were removed at 0, 1, 2 and 3 hours and examined on an 8% polyacrylamide gel. The results are shown in FIG. 18. The left lanes depict results in the absence of ligase. The right lanes depict extension after ligation. Bands ranging from 105 to 600 bases can be visualized in the right lanes. The results demonstrate that Klenow is able to extend from the Ext-primer, displace the downstream strand, and generate polymers.

EXAMPLE 11

Detection of EBV Early RNA (Eber-1) in Parotid Pleomorphic Adenomas by Ligation Dependent PCR LD-PCR utilizing a circularized probe was performed to detect Epstein Barr virus early RNA (EBER-1) in salivary benign mixed tumors (BMT). Six specimens of BMT and adjacent parotid tissue, and three specimens of normal parotid tissue (two removed from cysts and one from a hyperplastic lymph node) were snap frozen in embedding medium for frozen tissue specimens (OCT, Miles, Inc., Elkhart, Ind.) and liquid nitrogen, and stored at −70° C. The corresponding formalin fixed paraffin embedded (FFPE) blocks of tissue were obtained and studied in parallel to the fresh tissue. All tissue was sectioned on a microtome, the blade of which was cleaned with 10% Chlorox between cases to avoid cross contamination. Two to three sections of each specimen were placed in a 1.5 ml microcentrifuge tube. FFPE tissues were deparafinized by incubating at 60° C. for 10 minutes with 1 ml xylene (Sigma), which was subsequently removed by two washes with absolute ethanol. These specimens were dried by placing on a hot block at 65° C. for 30 minutes. Deparaffinized tissue was lysed by incubation at 100° C. for 30 minutes, then 65° C. for 30 minutes in 250 μl of lysis buffer: 5M guanidium thiocyanate (GTC)(Fluka), 0.5% bovine serum albumin (Sigma), 80 mM EDTA, 400 mM Tris HCl (pH 7.5), and 0.5% sodium-N-lauroylsarcosine (Sigma). Fresh frozen tissue was lysed by incubation at 37° C. for 60 minutes in the same lysis buffer. The lysed specimens were stored at −20° C. until use.

Two capture/amplification probes designed to flank the region of EBER-1 were used to capture target RNA. The sequences for capture probe 1 (SED ID NO:40) and capture/amplification probe 2 (SEQ ID NO:41) are shown in Table 4. The circular amplification probe (SEQ ID NO:42) was designed with 3' and 5' regions complementary to the chosen target sequence (Table 4). Interposed between these two regions is a noncomplementary linker sequence. This circular amplification probe circularized upon target hybridization in such a manner as to juxtapose the 5' and 3' ends. Seminested PCR was performed using primer pairs directed at this linker sequence, also shown in Table 4.

TABLE 4

Sequences of Capture Probes, Amplifiable Circular Target Probe, and PCR Primers

| | | |
|---|---|---|
| EBER-Cap/Amp-1 | 5'Biotin-AAGAgtctcctccctagcaaaacctctagggcagcgtaggtcctg-3' | (SEQ ID NO. 40) |
| EBER-Cap/Amp-2 | 5'Biotin AAGAggatcaaaacatgcggaccaccagctggtacttgaccgaag-3' | (SEQ ID No. 41) |
| Circular Amp PROBE | 5'tcaccacccgggacttgtacccgggacTGTCTGTGTATCTGCTAACCAAGAGCAA CTACACGAATTCTCGATTAGGTTACTGCgggaagacaaccacagacaccgttcc-3' | (SEQ ID No. 42) |
| 1$^{st}$ PCR primer pairs | GTTAGCAGATACACAGAC<br>CAAGAGCAACTACACGAA | (sense SEQ ID NO. 27)<br>(antisense SEQ ID NO. 28) |
| 2$^{ND}$ PCR primer pairs | GTTAGCAGATACACAGAC<br>TTCTCGATTAGGTTACTG | (sense SEQ ID NO. 27)<br>(antisense SEQ ID NO. 29) |

(lower case - complementary to EBER-1, upper case - generically designed)

LD-PCR was performed as follows. Briefly, 80 µl of lysis mixture were added to 120 µl of hybridization buffer (0.5% bovine serum albumin, 80 mM EDTA, 400 MM Tris-HCl (pH 7.5), and 0.5% sodium-N-lauroylsarcosine (Sigma) which contained $10^{10}$ molecules of phosphorylated target probe, and $10^{11}$ molecules of capture probe 1 and capture probe 2. Addition of the hybridization buffer reduced the GnSCN concentration from 5 M to 2 M to allow hybridization to occur. This mixture was incubated for one hour to allow the formation of hybrids, consisting of two DNA capture/amplification probes and one DNA circular amplification probe hybridized on the target RNA. Thirty µl of streptavidin-coated paramagnetic beads (Promega) were added to the mixture and incubated at 37° C. for 20 minutes to allow the hybrids to bond to the bead surface. The beads were washed twice with 150 µl of washing buffer (10 mM Tris HCl (pH 7.5), 0.5% Nonidet P-40, and 1.5 mM MgCl2 and 50 mM KCl) to remove nonhybridized probes as well as potential inhibitors of PCR (GTC, proteins) and potential sources of nonspecific PCR products (cellular nucleic acids). During each wash, the beads were drawn to the wall of the assay tube by placing the tube on a Magnetic Separation Stand (Promega), enabling the supernatant to be removed by aspiration. The 3' and 5' ends of the circular amplification probes hybridized directly adjacent to each other on the target RNA, were covalently linked, and hence circularized by incubation at 37° C. for 1 hour with 20 µl ligase solution (66 mM Tris HCl (pH 7.5), 1 mM dithiothreitol, 1 mM ATP, 1 mM $MnCl_2$ and 5 units of T4 DNA ligase (Boerhinger)). Ten ul of the ligation reaction mixture, including paramagnetic beads, were transferred to 20 µl of a PCR mixture containing 0.66 µM of PCR primer, 0.5 units Taq DNA polymerase, 0.2 mM dATP, 0.2 mM dCTP, 0.2 mM dGTP, 0.2 mM dTTP, 1.5 mM $Mg_2$, and 10 mM Tris-HCl (pH 8.3) and 50 mM KCl. The first PCR reaction was incubated at 94° C. for 30 seconds, 55° C. for 30 seconds, and 72° C. for 1 minute for 35 cycles in a GeneAmp PCR system 9600 thermocycler (Perkin Elmer, CT). After the first PCR, 5 ul of each reaction mixture were transferred into a 25 ul second PCR mixture containing the same components except that 0.66 µM of PCR primer 1 and 0.66 µM of PCR primer 3 were used for seminested PCR, which increases signal detection sensitivity without compromising amplification specificity. Extension of PCR primer along the covalently circularized probe results in the generation of a large multi-unit polymer (rolling circle polymerization). In fact, without digestion into monomeric units, the PCR polymer product cannot migrate into the polyacrylamide gel. Ten ul of the second PCR reaction were digested with restriction endonuclease EcoRI in the presence of 50 mM NaCl, 100 mM Tris-HCl (pH 7.5), 10 mM $MgCl_2$, 0.025% Triton X-100, and analyzed by gel electrophoresis through a 6% polyacrylamide gel and visualized by ultraviolet fluorescence after staining with ethidium bromide. The presence of a 90 base-pair band (second PCR product) and a 108 base-pair product (1st PCR) are considered as a positive result. The results are summarized in Table 5.

TABLE 5

EBV early RNA (EBER-1) detected by LD-PCR

| Case | Parotid tissue (frozen) | Pleomorphic Adenoma (frozen) | FFPE |
|---|---|---|---|
| 1 | positive | None | positive |
| 2 | negative | None | negative |
| 3 | negative | None | |
| 4 | ND | positive | negative |
| 5 | positive | positive | negative |
| 6 | positive | positive | positive |
| 7 | positive | negative | negative |
| 8 | positive | positive | negative |
| 9 | positive | negative | negative |

Note
Case 1 and 2 were from parotid tissues removed for reasons other than pleomorphic adenoma.
Cases 3-8 contained pleomorphic adenoma.
FFPE - formalin fixed paraffin embedded tissue.
Frozen-tissue snap frozen in liquid nitrogen.
ND - not done as tissue not available.

In sum, EBER-1 sequences were detected in six of eight parotid samples. Of the six pleomorphic adenomas studied, four were positive for EBER-1. Of the two cases in which EBER was not detected in the tumor, sequences were present within surrounding parotid tissue. The detection of EBER-1 sequences within corresponding formalin-fixed paraffin embedded tissue was considerably less sensitive—only two of eight specimens were positive.

In summary, the present results with ligation dependent PCR utilizing a circular probe demonstrate the presence of EBV-related sequences within the majority of pleomorphic adenomas studied. The present method exhibits a markedly increased detection rate relative to standard PCR for the detection of EBV DNA as performed by Taira et al. (1992) J. of Otorhinolarynaol Soc. Jap. 95: 860. In the present method, the 3' and 5' ends of a circularizable probe hybridized to the target sequence, resulting in juxtaposition. The juxtaposed sequences were then ligated, resulting in a circularized covalently linked probe that was locked onto the target sequence and thus resistant to stringent washes. PCR on the circular probe produced a rolling circle polymer, which was digested into monomeric units and visualized on a gel. The use of ligation dependent PCR with a circular probe, followed by detection by amplification of the probe by the rolling circle model, resulted in tremendous sensitivity of target detection in fresh frozen tissue.

EXAMPLE 12

Differential Display RAM

5' Capture/Amp-probes and 3' Arbitrary/Amp-probes are designed as follows. 12 possible 5' Capture/Amp-probe oligo (dT) probes, used in combination with 24 different 10-mer 3' Arbitrary/Amp-probes, are sufficient enough to display 10,000 of the mRNA species that are present in a mammalian cell (Liang et al., 1992, Science 257:967-971). Since the terminal 3' base of the 5' capture oligo (dT) probe provides most of the selectivity, the number of capture oligo (dT) probes may be reduced from 12 to 3 (Liang et al., Science 1992, 257:967-971; Liang et al., 1994, Nuci. Acid Res. 22:5763-5764).

Initially, three separate 5' Capture/Amp-probes are synthesized, each containing a nucleotide G, A, or C at the 3' termini. Adjacent to the terminal nucleotide is a oligo $(dT)_{11}$ which will serve as both a capture and anchoring sequence. The 5' region of the Capture/AMP-probes comprise multiple, i.e., 5-20, generic primer binding sequences with a biotin moiety at the 5' end. These multiple primer binding sites are designed for RAM amplification to ensure sensitivity. If initial tests with three Capture/Anchor probes do not achieve a good differential display, 4-12 separate Capture/Anchor probes can be synthesized based on the combination of the last two nucleotides (T12MN, M=degenerative A, G, or C; N=A, C, G, and T).

3' Arbitrary/Amp-probes, 10 nucleotides in length hybridize to mRNA, and produce enough display bands to be analyzed by a sequencing gel. However, not every probe 10 nucleotides in length is suitable. Probes should, therefore, be tested experimentally (Bauer, 1993, *Nucl. Acid Res.* 21:4272-4280). The actual number of 3' Arbitrary/Amp-probes required to display most mRNA species is 24 to 26 different probes. Therefore, initially, 24 3' Arbitrary/Amp-probes are synthesized separately. Each 3' Arbitrary/Amp-probe contains a 5' arbitrary sequence, for example 10 nucleotides in length, and a 3' RAM primer binding sequence which may be 70-130 nucleotides in length. The 5' end of each 3' Arbitrary/Amp-probe is phosphorylated by incubating with T4 DNA kinase in order for ligation to occur. The 3' Arbitrary/Amp-probes are mixed in an equal molar ratio to a final concentration of $10^{11}$ molecules/ul. The concentration of each 3' Arbitrary/Amp-probe may be changed to achieve best differential display.

The DD-RAM assay is carried out as previously described with minor modification (Zhang et al., 1998 Gene 211:277-285; Park, 1996, Amer. J. Path. 149:1485-1491). Tissue sections (5-10 um thickness) or cell suspensions ($1\times10^6$ cell/ml) are lysed by incubation at 37° C. for 60 minutes in 250 ul of lysis buffer containing 5M guanidium thiocyanate (GTC) (Fluka), 0.5% bovine serum albumin (Sigma Chemical Co., St. Louis, Mo.), 80 mM EDTA, 400 mM Tris HCl (pH 7.5), and 0.5% sodium-N-lauroylsarcosine (Sigma). 80 ul of lysis mixture is added to 120 ul of hybridization buffer [0.5% bovine serum albumin, 80 nM EDTA, 400 mM Tris-HCl (pH 7.5), and 0.5% sodium-N-lauroylsarcosine], which contains $10^{12}$ molecules of each capture/anchored probe and a mixture of $10^{11}$ molecules of phosphoryiated arbitrary sequence probes. Addition of hybridization buffer reduces the GTC concentration from 5 M to 2 M thereby allowing hybridization to occur. The hybridization mixture is incubated at 37° C. for one hour to allow the formation of hybrids, consisting of 5' Capture/Amp-probes and 3' Arbitrary/Amp-probes bound to their mRNA targets. 30 ul of streptavidin-coated paramagnetic beads (1 mg/ml, Promega, Madison, Wis.) are added to the mixture and incubated at 37° C. for 20 min to allow the hybrids to bind to the bead surface. The beads are then washed twice with 180 ul of washing buffer [10 mM TrisHCl (pH 7.5), 50 mM KCl, and 1.5 mM MgCl2, and 0.5% Nonidet P-40 (Sigma)] to remove nonhybridized probes, as well as GTC, proteins, nucleic acids, and any potential ligation and RAM inhibitors.

The hybrids are then resuspended in 20 ul RT/ligase solution [66 mM Tris HCl (pH 7.5), 1 mM dithiotbreitol, 1 nM ATP, 0.2 mM dTAP, 0.2 mM dCTP, 0.2 mM dGTP, 0.2 mM dTTP, 1 mM MnCl2, 5 mM MgCl2, and 200 units of Moloney murine leukemia virus reverse transcriptase (Boehringer Mannheim), and 5 units of T4 DNA ligase (Boehringer Mannheim)] (Hsuih, 1996) and incubated at 37° C. for one hour to extend from the 5' Capture/Amp-probe to the 3' downstream arbitrary sequence probes. The gap between the arbitrary probe and extended sequence is ligated to form covalently linked circular probes that can be amplified by a RAM assay as described above. Ten ul of the RT/ligation reaction mixture (including beads) is then transferred to 40 ul of a RAM mixture containing 0.66 uM of RAM forward primers and 0.66 uM of RAM reverse primers, 90 ng of φ29 DNA polymerase (Boehringer Mannheim), 80 μM $^{32}$P-dATP, 80 μM dCTP, 80 μM dGTP, 80 μM dTTP, 5 mM MgCl$_2$, and 66 mM Tris-HCl (pH 7.5). The RAM reaction is incubated at 35° C. for two hours. If the sensitivity is not enough to display the rare mRNA, 5 ul of the first RAM reaction mixture is transferred into a 25-ul second RAM mixture containing the same components for the second RAM reaction. Fifteen ul of the RAM reaction is analyzed by electrophoresis through a 6% polyacrylamide gel and visualized by autoradiograph.

EXAMPLE 13

RAM Assay with Multiple Primers

To test whether the addition of multiple RAM primers was able to increased the efficiency of the RAM reaction, a reaction was performed with an EBER Amp-probe-2 and three RAM primers. $10^{11}$ molecules of synthetic EBER DNA target was hybridized with $10^{11}$ molecules of EBER Amp-probe-2. Following ligation, one RAM forward primer and two reverse RAM primers (one forward and one reverse), or three RAM primers (one forward and two reverse) were added to each reaction together with φ29 DNA polymerase.

Figure 25:
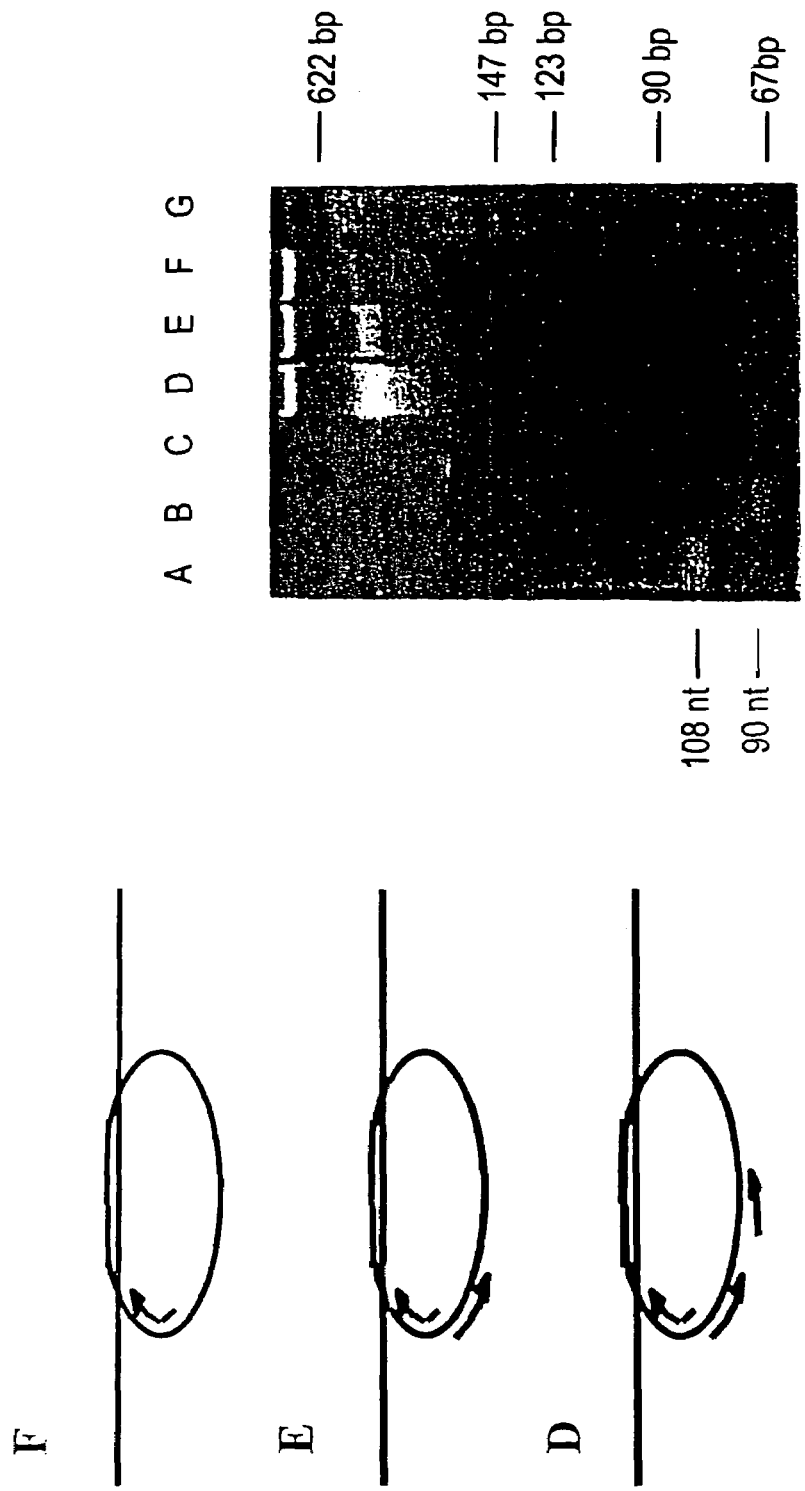
FIG. 25 depicts a RAM assay in the presence of 1, 2 and 3 primers.

The products of the reactions were examined on an 8% polyacrylamide gel. Results indicated that with one primer, multimeric ssDNA was produced and that a subset of the products were so large that they did not enter the gel. Although the amount of product increased with the increasing numbers of primers used (see, FIG. 25) two primers, lane B; three primers, lane C), exponential amplification was not observed. In the absence of target, no product was observed (lane D), indicating that the reaction is specific.

To increase the efficiency of the reaction, the number of primers was increased from 3 to 6 and the length of the primers was shortened from 18 nucleotides to 12 nucleotides. Shortening the primer length increases the accessibility of the primer to template, while increasing the primer number drives the equilibrium of the reaction towards hybridization.

Figure 26:
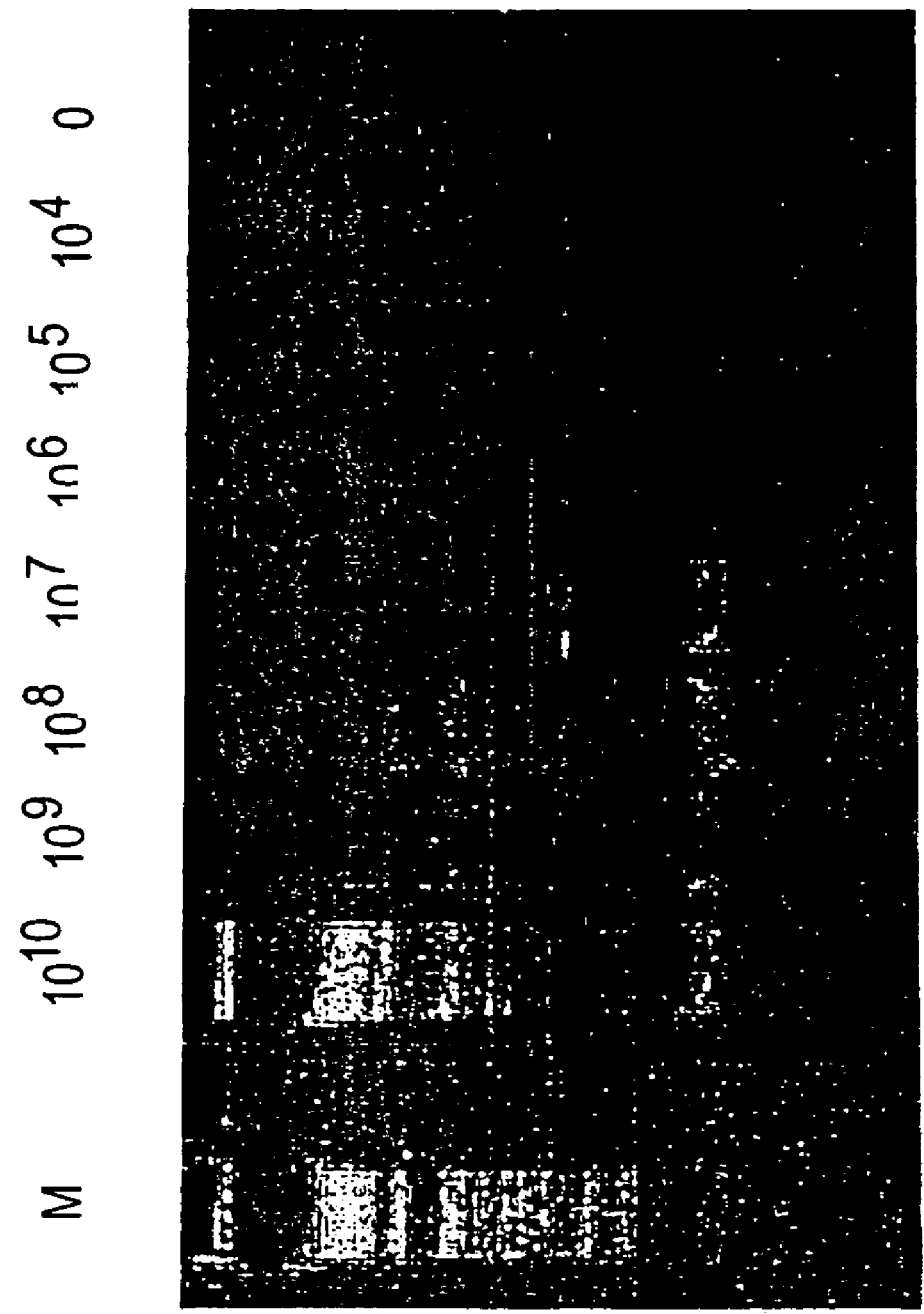
FIG. 26 depicts a RAM assay with serial dilutions of target DNA.

Conditions may be further optimized by addition of 6 mM [NH$_4$]$_2$SO4, 10% DMSO and 0.5 μg Gene 32 protein to RAM reaction. Under such conditions, $10^4$ molecules of EBER targets can be detected (FIG. 26).

As judged by the amount of DNA produced ($10^{13}$ molecules of DNA produced from $10^4$ molecules of initial Amp-probe-2), a billion-fold amplification was achieved. It is noteworthy that reducing primer length did not increase non-specific background.

Two additional Amp-probe-2 probes were designed to test the efficiency of the reaction in the presence of six primers. One Amp-probe-2 was synthesized to contain 3 forward-primer binding sites and 3 reverse primer binding sites with each primer spaced out by an opposite primer. The second Amp-probe-2 was designed to contain 6 primer binding sites, however, only 2 primer sequences (one forward and one reverse) were included. This particular primer design has the advantage of both increasing the hybridization rate while minimizing the interference between primers bound to Amp-probe-2.

EXAMPLE 14

Figure 23:
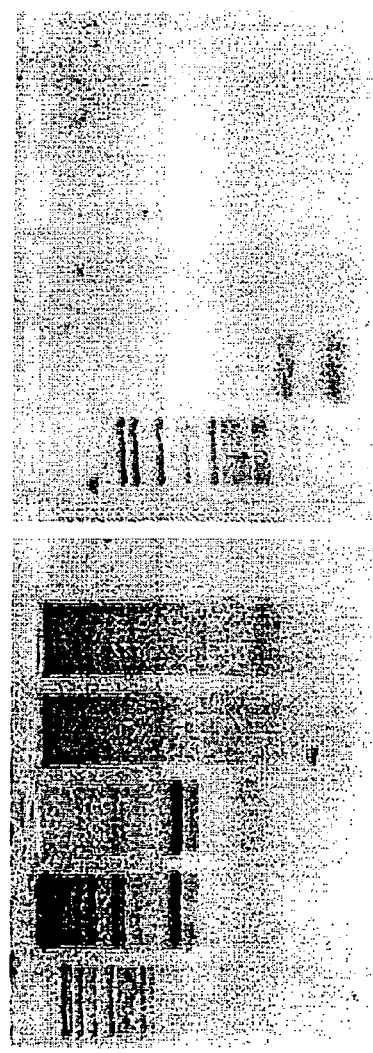
FIG. 23 is a graph depicting an anchor RAM reaction. C-probe (C-P) and biotinylated C-probe (biotinylated C-P) are incubated with targets and ligated. RAM reactions were performed in the presence of avidin or avidin plus signal nucleotides. The complex (avidin-signal nucleotide) does not inhibit Bst DNA polymerase but inhibits phi 29 DNA polymerase.

Anchoring RAM $10^{13}$ molecules of C-probe containing four biotin molecules in the linker region were incubated with $10^{14}$ molecules of synthetic DNA target for 5 minutes at 75° C. in 1× ligation buffer followed by incubation at room temperature for 10 minutes to allow the C-probe to hybridize to the target. Ligase was added to the mixture and incubated at 37° C. for one hour to link the two ends of the C-probe to form a closed circular probe. 0.1 μl of avidin (Boehringer Mannheim) was added to the reaction forming avidin/C-probe complexes. Biotinylated signal probe comprising 40 nucleotides with 3 biotin molecules was added to the reaction. The rolling circle reaction was initiated by addition of amplification primer and DNA polymerases. The reaction is not inhibited when Bst DNA polymerase is used. In contrast, the reaction is inhibited when phi 29 DNA is used. The results indicate that RAM primers are able to bind C-probe, even in the presence of large avidin molecules, and that Bst DNA polymerase is capable of bypassing the biotin-avidin complex and extend along the length of the C-probe FIG. 23.

EXAMPLE 15

Real-Time Ramification Amplification with Molecular Zipper

The zipper is composed of two probes with different lengths. The longer one hybridizes with the shorter one, leaving a single-stranded tail at the 3'-end of the longer probe. With this single stranded sequence, the zipper binds to the complementary region in the loop region of the Circular Probe. The 3'-end of the tail also serves as one of the two primers in the RAM reaction. The 5'-end of the long probe is labeled with a fluorescein molecule. At the 3'-end of the shorter probe, DABCYL, a quencher molecule is incorporated. When the two probes are hybridized together and therefore are in close proximity to one another, the fluorescent signal is absorbed by the quencher and no light is emitted. Once the amplification reaction has taken place and the long probe, which is used as the primer, is incorporated into the RAM product, the two probes are no longer in close proximity to one another. Therefore the quenching action of the DABCYL is inhibited and light is emitted from the fluorescein molecule.

The Molecular Zipper probes were prepared as follows: The two probes were synthesized by Integrated DNA Technologist, Inc, Coralville, Iowa, were purified by gel electrophoresis and were mixed at 1:1 molar ratio. Zipper probe 1 is a 38 nucleotide oligomer (also listed below as SEQ ID NO. 43), is the shorter one of the pair and is labeled with the DABCYL molecule on its 3' end. Zipper probe 2 is a 61 nucleotide oligomer (also listed below as SEQ ID NO. 44), is the longer one of the pair and is labeled with the fluorescein molecule on its 5' end.

```
Zipper Probe 1:                                          (SEQ ID NO. 43)
5'-TCGGCATCCG CATCCGCATT CGCATCCGGG TCCTC

AGC-DABCYL-3'

Zipper Probe 2:                                          (SEQ ID NO. 44)
5'-FLUORESCEIN-GCTGAGGACC CGGATGCGAA TGCGGATGCG

GATGCCGAAC CAAGAGCAAC TACACGAATT C-3'
```

The mixture was heated up to 95° C. for 5-10 min, and cooled down slowly to room temperature. The concentration of the zipper probes was adjusted to 50 μM with water or 1×TE buffer.

The RAM assay consisted of several steps including hybridization of the oligonucleotide probe (also listed below as SEQ ID NO. 45), and the capture probe (also listed below as SEQ ID NO. 46), to a target nucleic acid (also listed below as SEQ ID NO. 47). The oligonucleotide probe is 124 nucleotides long and contains sequences complementary to *Chlamydia trachomatis* elementary body, the target nucleic acid. The capture probe is a 43 nucleotide oligomer with a biotin molecule at its 5' end. The target nucleic acid molecule is from *Chlamydia trachomatis* elementary body and is 96 nucleotides long.

```
Oligonucleotide Probe:                                   (SEQ ID NO. 45)
5'-GGTTTTGTCT TCGTAACTCG CTCCGGATGT CTGTGTATCT

GCTAACCAAG AGCAACTACA CGAATTCTCG ATTAGGTTAC TGCGATTAGC

ACAAGCTCTA CAAGAGTACA TCGGTCAACG AAGA-3'

Capture Probe:                                           (SEQ ID NO. 46)
5'-Biotin-AAGAGCTTAA GAACCGTCAG ACAGAAAAGA GGATTATTAT

ACC-3'

Target Nucleic Acid Molecule:                            (SEQ ID NO. 47)

5'-TCCGGAGCGA GTTACGAAGA CAAAACCTCT TCGTTGACCG

ATGTACTCTT GTAGAAAGTT ATAATAATCC TCTTTTCTGT CTGACGGTTC TTAAGC-3'
```

The oligonucleotide probe/capture probe/target nucleic acid hybrid was then captured onto magnetic beads and washed to remove unbound probes and cellular components. The 3' and 5' ends of the oligonucleotides probe were ligated to form a closed circular probe. Then amplification by primer extension, strand displacement, and ramification was performed.

Hybridization of the oligonucleotides probe, capture probe and target was carried out in 80 μl reaction containing 2 M GTC, 0.5% bovine serum albumin (Sigma), 80 mM EDTA, 400 mM Tris-HCl (pH 7.5), 0.5% sodium-N-lauroylsarcosine (Sigma), 50 nM phosphorylated oligonucleotides probe, 2 μM capture probe, and various amount of targets (10 to $10^5$ molecules). The reaction was incubated at 55° C. for 2 hours to allow hybrid formation. Three μl of streptavidin-coated magnetic beads (10 mg/ml, Dynal, Lake Success, N.Y.), 80 μl of 10 mM Tris-HCl (pH 7.5) with 1 mM EDTA, and 2 M NaCl were added to the hybridization mixture and incubated at room temperature for 20 minutes to allow the hybrids to be captured on the beads through the binding of biotin on the capture probe with streptavidin coated on the surface of the beads.

The beads with the bound complex were then washed twice with 400 μl of TE buffer (10 mM Tris-HCl (pH 8.0) and 1 mM EDTA) at room temperature to remove unhybridized oligonucleotides probes. Twenty μl of ligase mixture containing 20 mM Tris-HCl (pH 7.6), 25 mM potassium acetate, 10 mM magnesium acetate, 10 mM DDT, 1 mM NAD, 0.1% Triton X-100, and 12 units of Taq DNA ligase (New England Biolabs, Mass.) were added to the bead pellet and incubated at 60° C. for 20 min. Ligation of the 3' and 5' ends of the oligonucleotides probe hybridized to the target nucleic acid allowed the formation of the closed circular probe that was locked on the target nucleic acid.

After ligation, the RAM reaction solution was aspirated and the beads were suspended in 50 μl of RAM reaction mixture containing 300 μM dNTP (USB Biochemicals), 20 mM Tris-HCl (pH 8.8), 10 mM KCl, 10 mM $(NH_4)_2SO_4$, 2 mM Mg $SO_4$, 0.1% Triton X-100, 1.2 μM of forward primers (also listed as SEQ ID NO. 48), 1.25 μM of double stranded zipper probes, 6.4 units of Bst DNA polymerase large fragment (New England Biolab), 1 μg T4 gene 32 protein (USB Biochemicals), and 6% Dimethyl sulfoxide (DMSO). This mixture was incubated at 63° C. for 1 hour in a Smart Cycler (Cepheid), a real-time thermocycler.

```
Forward Primer:                    (SEQ ID NO. 48)
5'-CTTGTGCTAA TCGCAGTAAC CTAAT-3'
```

Figure 22:
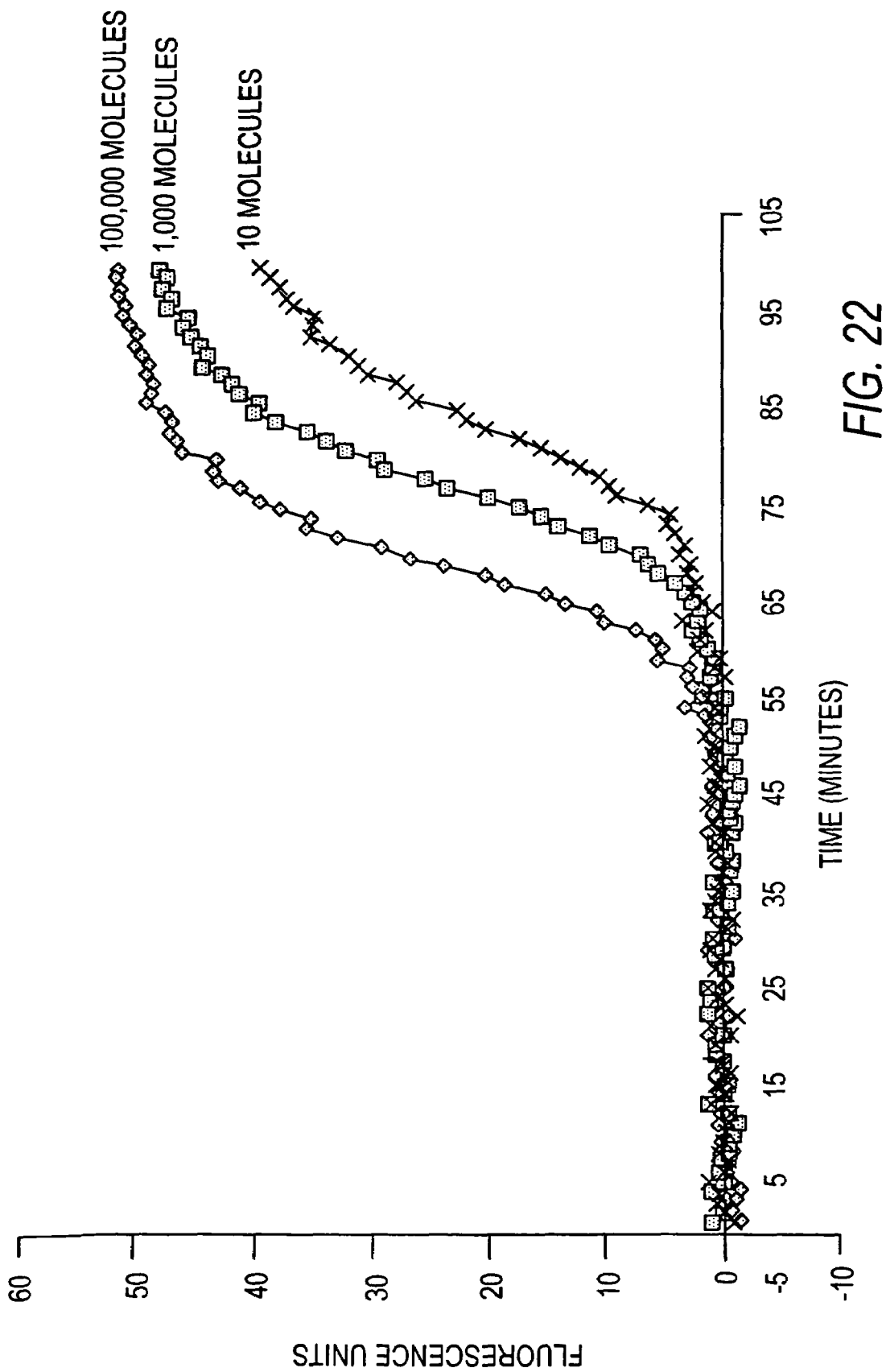
FIG. 22 is a graph of real-time detection of EBV-targets (100,000, 1,000 and 10 copies per reaction) using a molecular zipper in conjunction with a RAM reaction. The results indicate that the higher the number of target molecules present in the reaction, the faster the signal is detected.

The fluorescence produced by displacing the shorter probe of the zipper during the ramification was monitored on Smart Cycler Channel 1 (excitation wavelength: 450-495 nm, and emission wavelength: 505-537 nm). The results are shown in FIG. 22. The results demonstrate a target number dependent increase in fluorescent units. As low as 10 molecular targets can be detected. These results also indicate that the molecular zipper primer pair does not "open" under the reaction conditions and only become separated when they are incorporated into the RAM products.

EXAMPLE 16

Temperature Effects on Molecular Zipper Integrity

Figure 33:
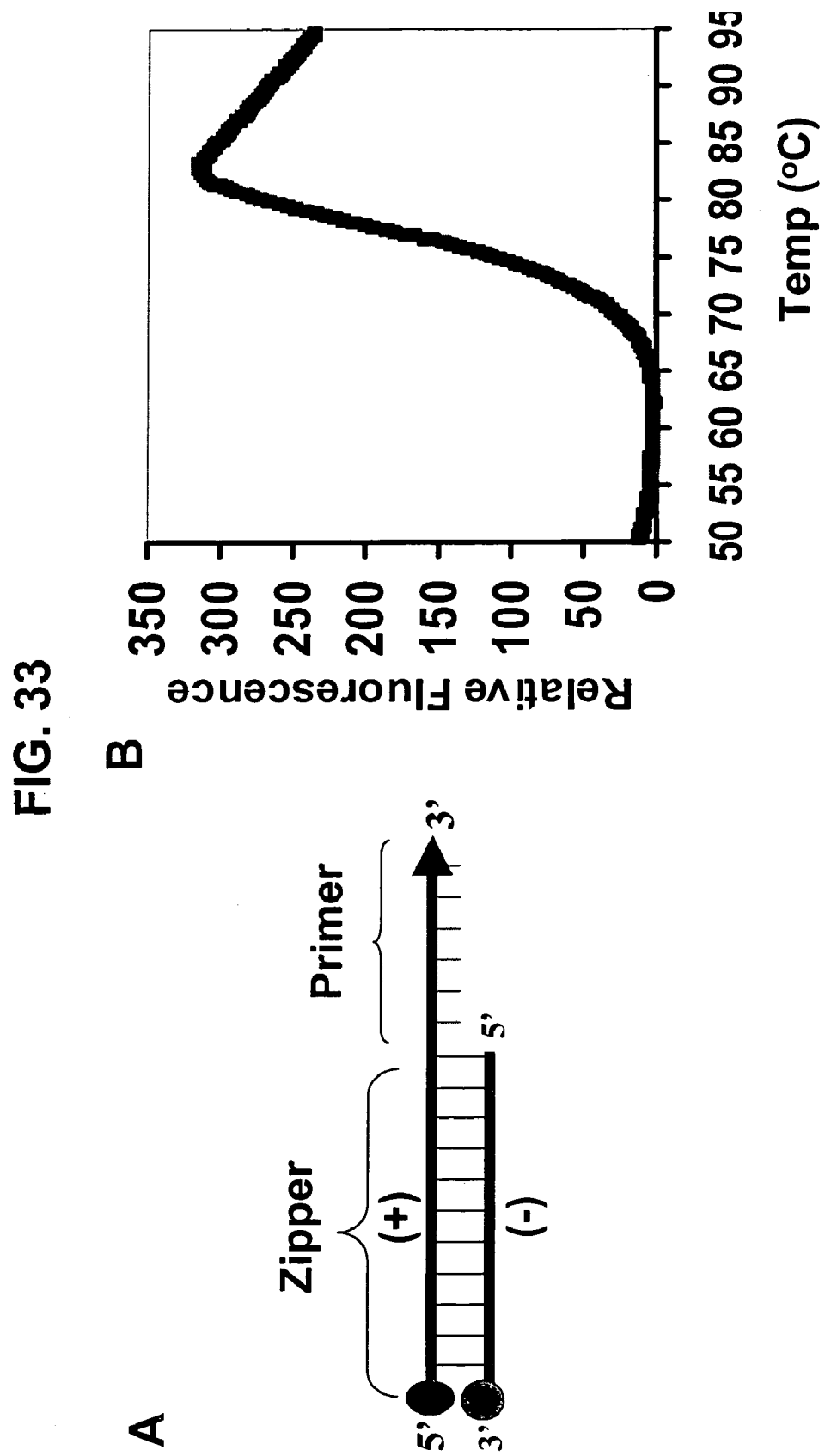
FIG. 33A is a schematic depiction of a molecular zipper probe.
FIG. 33B is a graph illustrating the denaturation curve of a molecular zipper probe.

FIG. 33A is a schematic representation of a molecular zipper probe comprising a double-stranded DNA molecule with a fluorescent moiety at the 5' end of one strand (positive) (SEQ ID NO: 43) and a quencher moiety at the 3' end of the opposite strand (negative) (SEQ ID NO: 44). The positive strand of the molecular zipper also contained an additional sequence (24 nucleotides) at its 3' end, which was identical to a portion of the C-probe (SEQ ID NO: 45) and was used as a reverse primer for the RAM reaction. In its double-stranded form, the fluorophore of the negative strand was held in close proximity to the quencher of the positive strand, therefore, no light was emitted. However, when the two strands were separated from each other, for example by an increase in temperature, quenching was relieved and light was emitted.

FIG. 33B shows a typical denaturation curve (or unzipping) of a molecular zipper probe. At temperatures below 70° C. there was low background fluorescence, indicating that both strands were bound together thereby efficiently quenching the fluorophore. However, there was a sharp increase in fluorescence above 72° C. (Tm~77° C.) that reached a plateau at 81° C., indicating a rapid unzipping of the molecular zipper. There was a decrease of fluorescence above 82° C., probably due to random interactions of the fluorophores with the quenchers in solution.

EXAMPLE 17

Quantification Using Molecular Zipper Probes

To determine the actual performance of the molecular zipper probe in RAM reactions, two reactions were carried out, both containing target DNA, a C-probe, and the molecular zipper probe. The first reaction included Taq DNA ligase and the other contained no ligase (see Experimental Details below).

Experimental Details:

Synthetic DNA Molecules: A molecular zipper is a dsDNA molecule composed of a positive strand (5'-Fluorescein-GCTGAGGACC CGGATGCGAA TGCGGATGCG GATGCCGA ACCAAGAGCAACTACACGAATTC-3' (61 nt)(SEQ ID NO: 43)) and a negative strand (5'-TCGGCATCCG CATCCGCATT CGCATCCGGG TCCTCAGC-DABCYL-3' (38 nt)(SEQ ID NO: 44)), where the underlined nucleotides indicate the primer sequence. Both oligos were obtained from Integrated DNA Technology, Inc, Coralville, Iowa. The sequence of the molecular zipper was designed with minimal secondary structure and a $T_m$ for the dsDNA portion of was ~77.5° C., which is above the RAM reaction temperature (63° C.). The dsDNA molecular zipper was formed by mixing equal amounts (20 μM) of positive and negative strands in a buffer containing 100 mM Tris and 10 mM EDTA (pH 8.3), heating at 95° C. for 5 min, and cooling slowly to room temperature. The C-probe with sequence (5'-GGTTTTGTCTTCGTAACTCGCTCCGGATGT CTGTGTATCT GCTAACCAAG AGCAACTACA CGAATTCTCG ATTAGGTTACTGCGATTAGCACAAGC TCTACAAGAGTACATCGGTCAACGAAGA-3' (124 nt) (SEQ ID NO: 45)) was obtained from Genelink, Hawthorne, N.Y., where the single underlines indicate the target complementary regions at the 5' and 3' ends, the double underline indicates the forward primer binding site and the dotted underline indicates the reverse primer binding site. The synthetic target DNA (5'-TCCGGAGCGAGTTACGAAGA CAAAACCTCTTCGTTGACCGATGTACTCTTGTAGA AAGTT ATAATAATCC TCTTTTCTGT CTGACGGTTC TTAAGC-3' (96 nt)(SEQ ID NO: 47)) also was obtained from Genelink, where the underlined nucleotides indicate the C-probe binding region. The forward primer (5'-CTTGT-GCTAA TCGCAGTAAC CTAAT-3' (25 nt) (SEQ ID NO: 48)) was synthesized at the DNA Core Facility of Mount Sinai School of Medicine, New York, N.Y. The reverse primer (5'-ACCAAGAGCA ACTACACGAA TTC-3' (23 nt)(SEQ ID NO: 49)) was synthesized at the DNA Core Facility of Mount Sinai School of Medicine, New York, N.Y.

Ligation reaction. Ligation of the C-probe was carried out by incubating the C-probe with a target DNA in 20 µl containing 20 mM Tris-HCl (pH 7.6), 25 mM potassium acetate, 10 mM magnesium acetate, 10 mM DTT, 1 mM NAD, 0.1% Triton X-100, and 12 units of Taq DNA ligase (New England BioLabs, Beverly, Mass.) at 65° C. for 15 min. The reaction was further incubated at 95° C. for 30 min to inactivate the ligase.

RAM assay. The isothermal RAM reaction was performed in 50 µl containing 20 mM Tris-HCl (pH 8.8), 300 µM each of dATP, dCTP, dGTP and dTTP, 10 mM KCl, 10 mM $(NH_4)_2SO_4$, 2 mM $MgSO_4$, 0.1% Triton X-100, 1.2 µM forward primer, 0.8 µM reverse primer, 0.4 µM molecular zipper, 6% Dimethylsulfoxide, and 6.4 units of exo⁻ Bst DNA polymerase (large fragment) (New England Biolabs). The reaction was incubated at 63° C. for 2-3 hours in a fluorometric thermal cycler (iCycler, Bio-Rad Laboratories, Hercules, Calif., or Smart Cycler, Cepheid, Sunnyvale, Calif.).

Figure 34:
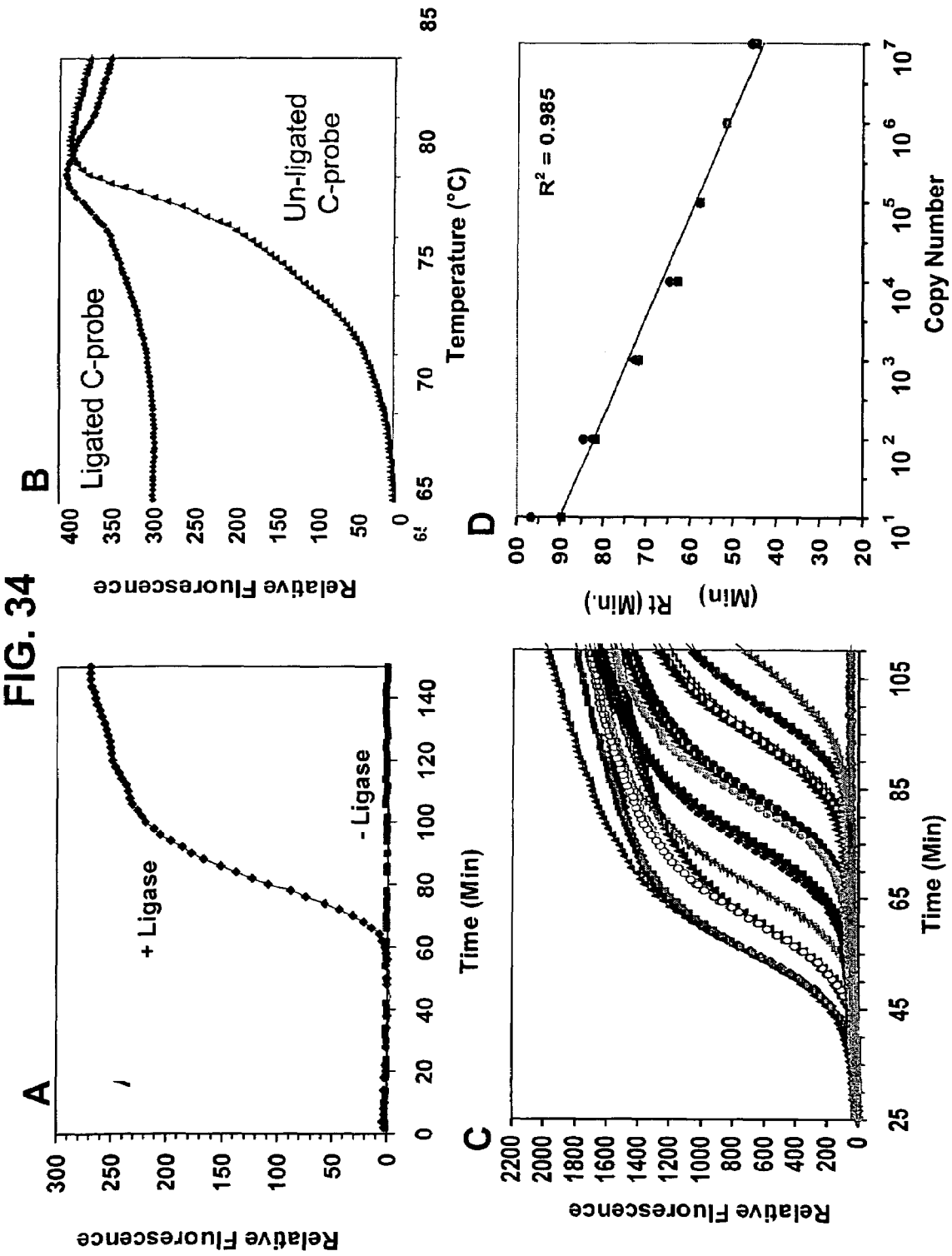
FIG. 34A is a graph illustrating the requirement of circular probe formation.
FIG. 34B is a graph illustrating the denaturation curves of the molecular zipper probes following RAM amplification, in the presence and absence of ligase.
FIG. 34C is graph of real-time detection of targets using a molecular zipper in conjunction with a RAM reaction. The results indicate that the higher the number of target molecules present in the reaction, the faster the signal is detected.
FIG. 34D is a graph illustrating the linear relationship between threshold times (Rt values) and initial copy number of the C-probe.

Results:

As expected, in the presence of DNA ligase the C-probes were formed and fluorescence was detected (FIG. 34A). The change in fluorescence in the RAM reaction was similar to that observed with conventional real-time exponential amplification (i.e. PCR), confirming the exponential nature of the RAM reaction. In the second reaction, no circular probe was formed in the absence of ligase, thus, no fluorescence was detected even after a long period of incubation, indicating circularization dependent amplification.

After completion of the RAM reaction, we further measured the fluorescence change of the RAM products during denaturation (FIG. 34B). Our results showed that the denaturation curve of the RAM products initiated with unligated C-probe was the same as that of the molecular zipper alone (compare FIGS. 34B and 33B), indicating that the molecular zipper was intact during the incubation. In contrast, the fluorescence intensity of the RAM products derived from the ligated C-probe only mildly increased (~25%) as compared to that derived from unligated C-probe, indicating that the majority of zippers were in an unzipped state. These results indicated that the positive strand of the molecular zipper was incorporated into the RAM products and the negative strand was displaced from the positive strand (i.e. unzipped).

To test the ability of the molecular zipper to quantify the numbers of C-probes present in a RAM reaction, we initiated the RAM reaction with known concentrations of ligated C-probes. FIG. 34C demonstrates that the time at which fluorescence rises above the baseline (response time, or $R_t$) was dependant on the number of C-probes initially present. The greater the number of C-probes, the earlier the response time. A linear relationship ($R^2$=0.985) existed between the threshold times (Rt values) and initial copy number of the C-probe (FIG. 34D), demonstrating the usefulness of the molecular zipper for real time quantitative DNA analysis in RAM reactions. Our results also demonstrated that RAM, in combination with the molecular zipper, detected a large dynamic range of C-probes ($10^1$ to $10^8$ molecules).

Various publications are cited herein, the contents of which are hereby incorporated by reference in their entireties.

We claim:

1. A method for detecting a target nucleic acid in a nucleic acid containing sample comprising:
   (a) contacting the nucleic acid containing sample with a circular oligonucleotide probe under conditions that allow hybridization between complementary sequences in the target nucleic acid and the circular oligonucleotide probe;
   (b) adding at least one forward primer comprising a sequence complementary to a portion of the circular oligonucleotide probe, under conditions where the forward primer is extended around the circular oligonucleotide probe for multiple revolutions to form a single-stranded DNA molecule comprising repeating units complementary to the sequence of the circular probe;
   (c) adding at least one oligonucleotide primer pair comprising a first primer and a second primer, wherein
      (i) the first primer of the pair comprises (A) a first sequence on its 3' end that is substantially identical to a portion of the circular oligonucleotide probe, (B) a second sequence that is complementary to the second primer of the pair, and (C) a signal generating moiety selected from the group consisting of a fluorescent agent and a chemiluminescent agent;
      (ii) the second primer of the pair comprises (A) a sequence that is complementary to the first primer and (B) a moiety capable of quenching, masking or inhibiting the activity of the signal generating moiety when located adjacent to, or in close proximity to the signal generating moiety; and
      (iii) when the first primer and the second primer are bound to one another, a signal generated by the signal generating moiety is inhibited;
   (d) adding at least one reverse primer comprising a sequence that is substantially identical to a portion of the circular oligonucleotide probe and wherein the forward primer, reverse primer, and the first primer and the second primer of the oligonucleotide primer pair are not identical;
   (e) adding a DNA polymerase having strand displacement activity and lacking 3' to 5' exonuclease activity; and
   (f) amplifying the circular oligonucleotide probe using ramification-extension amplification method (RAM) thus producing an amplification product comprising a sequence that is substantially identical to a sequence in the circular probe, and separating the signal generating moiety selected from the group consisting of a fluorescent agent and a chemiluminescent agent from the quenching, masking or inhibitory moiety by the action of the DNA polymerase having strand displacement activity and lacking 3' to 5' exonuclease activity during the amplification method, wherein detection of the signal indicates the presence of the target nucleic acid in the nucleic acid containing sample.

2. A method for detecting a target nucleic acid in a nucleic acid containing sample comprising:
   (a) contacting the nucleic acid containing sample with a linear oligonucleotide probe comprising 3' and 5' regions complementary to adjacent sequences in the target nucleic acid under conditions that allow hybridization between complementary sequences in the target nucleic acid and the linear oligonucleotide probe, whereupon binding to the target nucleic acid, the 3' and 5' ends of the linear oligonucleotide probe are adjacent to each other such that ligation of the 3' and 5' ends of the linear oligonucleotide probe forms the circular oligonucleotide probe, ligating the 3' and 5' ends of the linear oligonucleotide probe, and forming a circular oligonucleotide probe when the target nucleic acid is in the nucleic acid containing sample;
   (b) adding at least one forward primer comprising a sequence complementary to a portion of the circular oligonucleotide probe, under conditions where the forward primer is extended around the circular oligonucleotide probe for multiple revolutions to form a single-stranded DNA molecule comprising repeating units complementary to the sequence of the circular probe;
   (c) adding at least one oligonucleotide primer pair comprising a first primer and a second primer, wherein
      (i) the first primer of the pair comprises (A) a first sequence on its 3' end that is substantially identical to a portion of the circular oligonucleotide probe, (B) a second sequence that is complementary to the second primer of the pair, and (C) a signal generating moiety selected from the group consisting of a fluorescent agent and a chemiluminescent agent;
      (ii) the second primer of the pair comprises (A) a sequence that is complementary to the first primer and (B) a moiety capable of quenching, masking or inhibiting the activity of the signal generating moiety when located adjacent to, or in close proximity to the signal generating moiety; and
      (iii) when the first primer and the second primer are bound to one another, a signal generated by the signal generating moiety is inhibited;
   (d) adding at least one reverse primer comprising a sequence that is substantially identical to a portion of the circular oligonucleotide probe and wherein the forward primer, reverse primer, and the first primer and the second primer of the oligonucleotide primer pair are not identical;
   (e) adding a DNA polymerase having strand displacement activity and lacking 3' to 5'exonuclease activity; and
   (f) amplifying the circular oligonucleotide probe using ramification-extension amplification method (RAM) thus producing an amplification product comprising a sequence that is substantially identical to a sequence in the circular probe, and separating the signal generating moiety selected from the group consisting of a fluorescent agent and a chemiluminescent agent from the quenching, masking or inhibitory moiety by the action of the DNA polymerase having strand displacement activity and lacking 3' to 5' exonuclease activity during the amplification method, wherein detection of the signal indicates the presence of the target nucleic acid in the nucleic acid containing sample.

3. A method for detecting a target nucleic acid in a nucleic acid containing sample comprising:
   (a) contacting the nucleic acid containing sample with a circular oligonucleotide probe under conditions that allow hybridization between complementary sequences in the target nucleic acid and the circular oligonucleotide probe;
   (b) adding at least one multiple oligonucleotide primer complex comprising a first primer, a second primer and a third primer, under conditions where the multiple oligonucleotide primer complex is extended around the circular oligonucleotide probe for multiple revolutions to form a single-stranded DNA molecule comprising repeating units complementary to the sequence of the circular oligonucleotide probe, wherein
      (i) the first primer of the multiple oligonucleotide primer complex comprises (A) a first sequence on its 3' end that is complementary to a portion of the circular oligonucleotide probe, (B) a second sequence that is complementary to the second primer of the multiple oligonucleotide primer complex, and (C) a third sequence that is complementary to the third primer of the multiple oligonucleotide primer complex;

(ii) the second primer of the multiple oligonucleotide primer complex comprises (A) a sequence that is complementary to the second sequence of the first primer of the multiple oligonucleotide primer complex and (B) a signal generating moiety selected from the group consisting of a fluorescent agent and a chemiluminescent agent;

(iii) the third primer of the multiple oligonucleotide primer complex comprises (A) a sequence that is complementary to the third sequence of the first primer of the multiple oligonucleotide primer complex and (B) a moiety capable of quenching, masking or inhibiting the activity of the signal generating moiety when located adjacent to, or in close proximity to the signal generating moiety; and (iv) when the first, second and third primers of the multiple oligonucleotide primer complex are bound to one another, a signal generated by the signal generating moiety is inhibited;

(c) adding at least one reverse primer comprising a sequence that is substantially identical to a portion of the circular oligonucleotide probe;

(d) adding a DNA polymerase having strand displacement activity and lacking 3' to 5' exonuclease activity; and (e) amplifying the circular oligonucleotide probe using ramification-extension amplification method (RAM) thus producing an amplification product comprising a sequence that is substantially identical to a sequence in the circular oligonucleotide probe, and separating the signal generating moiety from the quenching, masking or inhibitory moiety to generate a signal by the action of the DNA polymerase having strand displacement activity and lacking 3' to 5' exonuclease activity during the amplification method, wherein detection of the signal indicates the presence of the target nucleic acid in the nucleic acid containing sample.

4. A method for detecting a target nucleic acid in a nucleic acid containing sample comprising:

(a) contacting the nucleic acid containing sample with a linear oligonucleotide probe comprising 3' and 5' regions complementary to adjacent sequences in the target nucleic acid under conditions that allow hybridization between complementary sequences in the target nucleic acid and the linear oligonucleotide probe, whereupon binding to the target nucleic acid, the 3' and 5' ends of the linear oligonucleotide probe are adjacent to each other such that ligation of the 3' and 5' ends of the linear oligonucleotide probe forms the circular oligonucleotide probe, ligating the 3' and 5' ends of the linear oligonucleotide probe, and forming a circular oligonucleotide probe when the target nucleic acid is in the nucleic acid containing sample;

(b) adding at least one multiple oligonucleotide primer complex comprising a first primer, a second primer and a third primer, under conditions where the multiple oligonucleotide primer complex is extended around the circular oligonucleotide probe for multiple revolutions to form a single-stranded DNA molecule comprising repeating units complementary to the sequence of the circular oligonucleotide probe, wherein (i) the first primer of the multiple oligonucleotide primer complex comprises (A) a first sequence on its 3' end that is complementary to a portion of the circular oligonucleotide probe, (B) a second sequence that is complementary to the second primer of the multiple oligonucleotide primer complex, and (C) a third sequence that is complementary to the third primer of the multiple oligonucleotide primer complex;

(ii) the second primer of the multiple oligonucleotide primer complex comprises (A) a sequence that is complementary to the second sequence of the first primer of the multiple oligonucleotide primer complex and (B) a signal generating moiety selected from the group consisting of a fluorescent agent and a chemiluminescent agent;

(iii) the third primer of the multiple oligonucleotide primer complex comprises (A) a sequence that is complementary to the third sequence of the first primer of the multiple oligonucleotide primer complex and (B) a moiety capable of quenching, masking or inhibiting the activity of the signal generating moiety when located adjacent to, or in close proximity to the signal generating moiety; and (iv) when the first, second and third primers of the multiple oligonucleotide primer complex are bound to one another, a signal generated by the signal generating moiety is inhibited;

(c) adding at least one reverse primer comprising a sequence that is substantially identical to a portion of the circular oligonucleotide probe;

(d) adding a DNA polymerase having strand displacement activity and lacking 3' to 5' exonuclease activity; and (e) amplifying the circular oligonucleotide probe using ramification-extension amplification method (RAM) thus producing an amplification product comprising a sequence that is substantially identical to a sequence in the circular oligonucleotide probe, and separating the signal generating moiety from the quenching, masking or inhibitory moiety to generate a signal by the action of the DNA polymerase having strand displacement activity and lacking 3' to 5' exonuclease activity during the amplification method, wherein detection of the signal indicates the presence of the target nucleic acid in the nucleic acid containing sample.

5. A method for detecting a target nucleic acid in a nucleic acid containing sample comprising:

(a) contacting the nucleic acid containing sample with a circular oligonucleotide probe under conditions that allow hybridization between complementary sequences in the target nucleic acid and the circular oligonucleotide probe;

(b) adding at least one forward primer comprising a sequence that is complementary to a portion of the circular oligonucleotide probe, under conditions where the forward primer is extended around the circular oligonucleotide probe for multiple revolutions to form a single-stranded DNA molecule comprising repeating units complementary to the sequence of the circular oligonucleotide probe;

(c) adding at least one multiple oligonucleotide primer complex comprising a first primer, a second primer and a third primer, wherein (i) the first primer of the multiple oligonucleotide primer complex comprises (A) a first sequence on its 3' end that is substantially identical to a portion of the circular oligonucleotide probe, (B) a second sequence that is complementary to the second primer of the pair, and (C) a third sequence that is complementary to the third primer of the multiple oligonucleotide primer complex;
 (ii) the second primer of the multiple oligonucleotide primer complex comprises (A) a sequence that is complementary to the second sequence of the first primer of the multiple oligonucleotide primer complex and (B) a signal generating moiety selected from the group consisting of a fluorescent agent and a chemiluminescent agent;
 (iii) the third primer of the multiple oligonucleotide primer complex comprises (A) a sequence that is complementary to the third sequence of the first primer of the multiple oligonucleotide primer complex and (B) a moiety capable of quenching, masking or inhibiting the activity of the signal generating moiety when located adjacent to, or in close proximity to the signal generating moiety; and
 (iv) when the first, second and third primers of the multiple oligonucleotide primer complex are bound to one another, a signal generated by the signal generating moiety is inhibited; and
(d) adding a DNA polymerase having strand displacement activity and lacking 3' to 5' exonuclease activity; and
(e) amplifying the circular oligonucleotide probe using ramification-extension amplification method (RAM) thus producing an amplification product comprising a sequence that is substantially identical to a sequence in the circular oligonucleotide probe, and separating the signal generating moiety from the quenching, masking or inhibitory moiety to generate a signal by the action of the DNA polymerase having strand displacement activity and lacking 3' to 5' exonuclease activity during the amplification method, wherein detection of the signal indicates the presence of the target nucleic acid in the nucleic acid containing sample.

6. A method for detecting a target nucleic acid in a nucleic acid containing sample comprising:
(a) contacting the nucleic acid containing sample with a linear oligonucleotide probe comprising 3' and 5' regions complementary to adjacent sequences in the target nucleic acid under conditions that allow hybridization between complementary sequences in the target nucleic acid and the linear oligonucleotide probe, whereupon binding to the target nucleic acid, the 3' and 5' ends of the linear oligonucleotide probe are adjacent to each other such that ligation of the 3' and 5' ends of the linear oligonucleotide probe forms the circular oligonucleotide probe, ligating the 3' and 5' ends of the linear oligonucleotide probe, and forming a circular oligonucleotide probe when the target nucleic acid is in the nucleic acid containing sample;
(b) adding at least one forward primer comprising a sequence that is complementary to a portion of the circular oligonucleotide probe, under conditions where the forward primer is extended around the circular oligonucleotide probe for multiple revolutions to form a single-stranded DNA molecule comprising repeating units complementary to the sequence of the circular oligonucleotide probe;
(c) adding at least one multiple oligonucleotide primer complex comprising a first primer, a second primer and a third primer, wherein
 (i) the first primer of the multiple oligonucleotide primer complex comprises (A) a first sequence on its 3' end that is substantially identical to a portion of the circular oligonucleotide probe, (B) a second sequence that is complementary to the second primer of the pair, and (C) a third sequence that is complementary to the third primer of the multiple oligonucleotide primer complex;
 (ii) the second primer of the multiple oligonucleotide primer complex comprises (A) a sequence that is complementary to the second sequence of the first primer of the multiple oligonucleotide primer complex and (B) a signal generating moiety selected from the group consisting of a fluorescent agent and a chemiluminescent agent;
 (iii) the third primer of the multiple oligonucleotide primer complex comprises (A) a sequence that is complementary to the third sequence of the first primer of the multiple oligonucleotide primer complex and (B) a moiety capable of quenching, masking or inhibiting the activity of the signal generating moiety when located adjacent to, or in close proximity to the signal generating moiety; and
 (iv) when the first, second and third primers of the multiple oligonucleotide primer complex are bound to one another, a signal generated by the signal generating moiety is inhibited; and
(d) adding a DNA polymerase having strand displacement activity and lacking 3' to 5' exonuclease activity; and
(e) amplifying the circular oligonucleotide probe using ramification-extension amplification method (RAM) thus producing an amplification product comprising a sequence that is substantially identical to a sequence in the circular oligonucleotide probe, and separating the signal generating moiety from the quenching, masking or inhibitory moiety to generate a signal by the action of the DNA polymerase having strand displacement activity and lacking 3' to 5' exonuclease activity during the amplification method, wherein detection of the signal indicates the presence of the target nucleic acid in the nucleic acid containing sample.

* * * * *

SEQUENCE LISTING

<160> NUMBER OF SEQ ID NOS: 49

<210> SEQ ID NO 1
<211> LENGTH: 59
<212> TYPE: DNA
<213> ORGANISM: Artificial sequence
<220> FEATURE:
<223> OTHER INFORMATION: Oligonucleotide probe

<400> SEQUENCE: 1
ccatcttcct gctaatttta agacctggta acaggatttc cccgggaatt caagcttgg        59

<210> SEQ ID NO 2
<211> LENGTH: 92
<212> TYPE: DNA
<213> ORGANISM: Artificial sequence
<220> FEATURE:
<223> OTHER INFORMATION: Oligonucleotide probe

<400> SEQUENCE: 2
gggttgaccc ggctagatcc gggtgtgtcc tctctaactt tcgagtagag aggtgagaaa        60
accccgttat ctgtatgtac tgttttact gg        92

<210> SEQ ID NO 3
<211> LENGTH: 151
<212> TYPE: DNA
<213> ORGANISM: Artificial sequence

```
<220> FEATURE:
<223> OTHER INFORMATION: Oligonucleotide probe

<400> SEQUENCE: 3 ggguttgaccc ggctagatcc gggtgtgtcc tctctaactt tcgagtagag aggtgagaaa      60
accccgttat ctgtatgtac tgtttttact ggccatcttc ctgctaattt taagacctgg     120
taacaggatt tccccgggaa ttcaagcttg g                                    151

<210> SEQ ID NO 4
<211> LENGTH: 90
<212> TYPE: DNA
<213> ORGANISM: Artificial sequence
<220> FEATURE:
<223> OTHER INFORMATION: Oligonucleotide probe

<400> SEQUENCE: 4 ggguttgaccc ggctagatcc gggtgtgtcc tctctaactt tcgagtagag aggtgagaaa      60
accccgttat cctggtaaca ggatttcccc                                       90

<210> SEQ ID NO 5
<211> LENGTH: 21
<212> TYPE: DNA
<213> ORGANISM: Artificial sequence
<220> FEATURE:
<223> OTHER INFORMATION: Oligonucleotide probe

<400> SEQUENCE: 5
caagcttgaa ttcccgggga a                                                21

<210> SEQ ID NO 6
<211> LENGTH: 20
<212> TYPE: DNA
<213> ORGANISM: Artificial sequence
<220> FEATURE:
<223> OTHER INFORMATION: Oligonucleotide probe

<400> SEQUENCE: 6
gggttgaccc ggctagatcc                                                  20

<210> SEQ ID NO 7
<211> LENGTH: 54
<212> TYPE: DNA
<213> ORGANISM: Artificial sequence
<220> FEATURE:
<223> OTHER INFORMATION: Oligonucleotide probe

<400> SEQUENCE: 7
caggcttatc ccgaagtgcc tggtaacagg atttccccgg gaattcaagc ttgg             54

<210> SEQ ID NO 8
<211> LENGTH: 91
<212> TYPE: DNA
<213> ORGANISM: Artificial sequence
<220> FEATURE:
<223> OTHER INFORMATION: Oligonucleotide probe

<400> SEQUENCE: 8 ggguttgaccc ggctagatcc gggtgtgtcc tctctaactt tcgagtagag aggtgagaaa      60
accccgttat ccggtattag acccagtttc c                                     91

<210> SEQ ID NO 9
<211> LENGTH: 145
<212> TYPE: DNA
```

```
<213> ORGANISM: Artificial sequence
<220> FEATURE:
<223> OTHER INFORMATION: Oligonucleotide probe

<400> SEQUENCE: 9
gggttgaccc ggctagatcc gggtgtgtcc tctctaactt tcgagtagag aggtgagaaa      60
accccgttat ccggtattag acccagtttc ccaggcttat cccgaagtgc ctggtaacag     120
gatttccccg ggaattcaag cttgg                                           145

<210> SEQ ID NO 10
<211> LENGTH: 56
<212> TYPE: DNA
<213> ORGANISM: Artificial sequence
<220> FEATURE:
<223> OTHER INFORMATION: Oligonucleotide probe

<400> SEQUENCE: 10
gaagacatgc atcccgtggt cctggtaaca ggatttcccc gggaattcaa gcttgg          56

<210> SEQ ID NO 11
<211> LENGTH: 90
<212> TYPE: DNA
<213> ORGANISM: Artificial Sequence
<220> FEATURE:
<223> OTHER INFORMATION: Oligonucleotide probe

<400> SEQUENCE: 11
gggttgaccc ggctagatcc gggtgtgtcc tctctaactt tcgagtagag aggtgagaaa      60
accccgttat cgctaaagcg ctttccacca                                       90

<210> SEQ ID NO 12
<211> LENGTH: 146
<212> TYPE: DNA
<213> ORGANISM: Artificial Sequence
<220> FEATURE:
<223> OTHER INFORMATION: Oligonucleotide probe

<400> SEQUENCE: 12
gggttgaccc ggctagatcc gggtgtgtcc tctctaactt tcgagtagag aggtgagaaa      60
accccgttat cgctaaagcg ctttccacca gaagacatgc atcccgtggt cctggtaaca     120
ggatttcccc gggaattcaa gcttgg                                          146

<210> SEQ ID NO 13
<211> LENGTH: 56
<212> TYPE: DNA
<213> ORGANISM: Artificial Sequence
<220> FEATURE:
<223> OTHER INFORMATION: Oligonucleotide probe

<400> SEQUENCE: 13
aaagacatgc atcccgtggt cctggtaaca ggatttcccc gggaattcaa gcttgg          56

<210> SEQ ID NO 14
<211> LENGTH: 90
<212> TYPE: DNA
<213> ORGANISM: Artificial Sequence
<220> FEATURE:
<223> OTHER INFORMATION: Oligonucleotide probe

<400> SEQUENCE: 14
gggttgaccc ggctagatcc gggtgtgtcc tctctaactt tcgagtagag aggtgagaaa      60
accccgttat cgctaaagcg ctttccacct                                       90
```

<210> SEQ ID NO 15
<211> LENGTH: 146
<212> TYPE: DNA
<213> ORGANISM: Artificial Sequence
<220> FEATURE:
<223> OTHER INFORMATION: Oligonucleotide probe

<400> SEQUENCE: 15

```
gggttgaccc ggctagatcc gggtgtgtcc tctctaactt tcgagtagag aggtgagaaa    60
accccgttat cgctaaagcg ctttccacct aaagacatgc atcccgtggt cctggtaaca   120
ggatttcccc gggaattcaa gcttgg                                        146
```

<210> SEQ ID NO 16
<211> LENGTH: 55
<212> TYPE: DNA
<213> ORGANISM: Artificial Sequence
<220> FEATURE:
<223> OTHER INFORMATION: Oligonucleotide primer

<400> SEQUENCE: 16

```
gcagaccact atggctctcc ctggtaacag gatttccccg ggaattcaag cttgg         55
```

<210> SEQ ID NO 17
<211> LENGTH: 90
<212> TYPE: DNA
<213> ORGANISM: Artificial sequence
<220> FEATURE:
<223> OTHER INFORMATION: Oligonucleotide probe

<400> SEQUENCE: 17

```
gggttgaccc ggctagatcc gggtgtgtcc tctctaactt tcgagtagag aggtgagaaa    60
accccgttat ccggtgtact caccggttcc                                     90
```

<210> SEQ ID NO 18
<211> LENGTH: 145
<212> TYPE: DNA
<213> ORGANISM: Artificial Sequence
<220> FEATURE:
<223> OTHER INFORMATION: Oligonucleotide probe

<400> SEQUENCE: 18

```
gggttgaccc ggctagatcc gggtgtgtcc tctctaactt tcgagtagag aggtgagaaa    60
accccgttat ccggtgtact caccggttcc gcagaccact atggctctcc ctggtaacag   120
gatttccccg ggaattcaag cttgg                                         145
```

<210> SEQ ID NO 19
<211> LENGTH: 47
<212> TYPE: DNA
<213> ORGANISM: Artificial Sequence
<220> FEATURE:
<223> OTHER INFORMATION: Oligonucleotide probe

<400> SEQUENCE: 19

```
ggtgaaattg ctgccattgt ctgtatgttg tctgtgtatc tgctaac                  47
```

<210> SEQ ID NO 20
<211> LENGTH: 65
<212> TYPE: DNA
<213> ORGANISM: Artificial Sequence
<220> FEATURE:
<223> OTHER INFORMATION: Oligonucleotide probe

```
<400> SEQUENCE: 20
caagagcaac tacacgaatt ctcgattagg ttactgcagc aacaggcggc cttaactgta      60
gtact                                                                 65

<210> SEQ ID NO 21
<211> LENGTH: 112
<212> TYPE: DNA
<213> ORGANISM: Artificial Sequence
<220> FEATURE:
<223> OTHER INFORMATION: Oligonucleotide probe

<400> SEQUENCE: 21
ggtgaaattg ctgccattgt ctgtatgttg tctgtgtatc tgctaaccaa gagcaactac      60
acgaattctc gattaggtta ctgcagcaac aggcggcctt aactgtagta ct             112

<210> SEQ ID NO 22
<211> LENGTH: 45
<212> TYPE: DNA
<213> ORGANISM: Artificial Sequence
<220> FEATURE:
<223> OTHER INFORMATION: Oligonucleotide probe

<400> SEQUENCE: 22
aagagcgtga agacagtagt tcctcacagg ggagtgattc atggt                     45

<210> SEQ ID NO 23
<211> LENGTH: 45
<212> TYPE: DNA
<213> ORGANISM: Artificial Sequence
<220> FEATURE:
<223> OTHER INFORMATION: Oligonucleotide probe

<400> SEQUENCE: 23
aagacccaac actactcggc tagcagtctt gcggggcac gccca                      45

<210> SEQ ID NO 24
<211> LENGTH: 51
<212> TYPE: DNA
<213> ORGANISM: Artificial Sequence
<220> FEATURE:
<223> OTHER INFORMATION: Oligonucleotide probe

<400> SEQUENCE: 24
actcaccggt tccgcagacc actatggctc gttgtctgtg tatctgctaa c              51

<210> SEQ ID NO 25
<211> LENGTH: 69
<212> TYPE: DNA
<213> ORGANISM: Artificial Sequence
<220> FEATURE:
<223> OTHER INFORMATION: Oligonucleotide primer

<400> SEQUENCE: 25
caagagcaac tacacgaatt ctcgattagg ttactgcaga ggacccggtc gtcctggcaa     60
ttccggtgt                                                             69

<210> SEQ ID NO 26
<211> LENGTH: 120
<212> TYPE: DNA
<213> ORGANISM: Artificial Sequence
<220> FEATURE:
<223> OTHER INFORMATION: Oligonucleotide primer

<400> SEQUENCE: 26
```

```
caagagcaac tacacgaatt ctcgattagg ttactgcaga ggacccggtc gtcctggcaa    60
ttccggtgta ctcaccggtt ccgcagacca ctatggctcg ttgtctgtgt atctgctaac   120
```

<210> SEQ ID NO 27
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 27

```
gttagcagat acacagac                                                   18
```

<210> SEQ ID NO 28
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 28

```
caagagcaac tacacgaa                                                   18
```

<210> SEQ ID NO 29
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 29

```
ttctcgatta ggttactg                                                   18
```

<210> SEQ ID NO 30
<211> LENGTH: 100
<212> TYPE: DNA
<213> ORGANISM: Artificial Sequence
<220> FEATURE:
<223> OTHER INFORMATION: Oligonucleotide primer

<400> SEQUENCE: 30

```
caagagcaac tacacgaatt ctcgattagg ttactgcagc gtcctggcaa ttccggtgta    60
ctcaccggtt ccgcagaccg ttgtctgtgt atctgctaac                          100
```

<210> SEQ ID NO 31
<211> LENGTH: 108
<212> TYPE: DNA
<213> ORGANISM: Artificial Sequence
<220> FEATURE:
<223> OTHER INFORMATION: Oligonucleotide primer

<400> SEQUENCE: 31

```
cctttcgcga cccaacacta ctcggctgtc tgtgtatctg ctaaccaaga gcaactacac    60
gaattctcga ttaggttact gcgcacccta tcaggcagta ccacaagg                108
```

<210> SEQ ID NO 32
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 32
gcgacactcc accatagat					19

<210> SEQ ID NO 33
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 33
gctcatggtg cacggtcta					19

<210> SEQ ID NO 34
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 34
cttctacaat gagctgcgtg tggct					25

<210> SEQ ID NO 35
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 35
cgctcattgc caatggtgat gacct					25

<210> SEQ ID NO 36
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 36
ctgtgaggaa ctactgtct					19

<210> SEQ ID NO 37
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 37
actcgcaagc accctatca					19

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 38
aaggccaacc gcgagaagat					20

<210> SEQ ID NO 39
<211> LENGTH: 18
<212> TYPE: DNA
<213> ORGANISM: Artificial Sequence

```
<220> FEATURE:
<223> OTHER INFORMATION: Oligonucleotide primer

<400> SEQUENCE: 39
tcacgcacga tttcccgc                                                18

<210> SEQ ID NO 40
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 40
aagagtctcc tccctagcaa aacctctagg gcagcgtagg tcctg                  45

<210> SEQ ID NO 41
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 41
aagaggatca aaacatgcgg accaccagct ggtacttgac cgaag                  45

<210> SEQ ID NO 42
<211> LENGTH: 109
<212> TYPE: DNA
<213> ORGANISM: Artificial Sequence
<220> FEATURE:
<223> OTHER INFORMATION: Oligonucleotide primer

<400> SEQUENCE: 42
tcaccacccg ggacttgtac ccgggactgt ctgtgtatct gctaaccaag agcaactaca  60
cgaattctcg attaggttac tgcgggaaga caaccacaga caccgttcc             109

<210> SEQ ID NO 43
<211> LENGTH: 39
<212> TYPE: DNA
<213> ORGANISM: Artificial Sequence
<220> FEATURE:
<223> OTHER INFORMATION: Zipper Probe 1
<220> FEATURE:
<221> NAME/KEY: misc_feature
<222> LOCATION: (39)..(39)
<223> OTHER INFORMATION: n = DABCYL molecule

<400> SEQUENCE: 43
tcggcatccg catccgcatt cgcatccggg tcctcagcn                         39

<210> SEQ ID NO 44
<211> LENGTH: 62
<212> TYPE: DNA
<213> ORGANISM: Artificial Sequence
<220> FEATURE:
<223> OTHER INFORMATION: Zipper Probe 2
<220> FEATURE:
<221> NAME/KEY: misc_feature
<222> LOCATION: (1)..(1)
<223> OTHER INFORMATION: n = FLUORESCEIN molecule

<400> SEQUENCE: 44
ngctgaggac ccggatgcga atgcggatgc ggatgccgaa ccaagagcaa ctacacgaat  60
tc                                                                 62
```

```
<210> SEQ ID NO 45
<211> LENGTH: 124
<212> TYPE: DNA
<213> ORGANISM: Artificial Sequence
<220> FEATURE:
<223> OTHER INFORMATION: Oligonucleotide Probe

<400> SEQUENCE: 45
ggttttgtct tcgtaactcg ctccggatgt ctgtgtatct gctaaccaag agcaactaca      60
cgaattctcg attaggttac tgcgattagc acaagctcta caagagtaca tcggtcaacg     120
aaga                                                                  124

<210> SEQ ID NO 46
<211> LENGTH: 44
<212> TYPE: DNA
<213> ORGANISM: Artificial Sequence
<220> FEATURE:
<223> OTHER INFORMATION: Capture Probe
<220> FEATURE:
<221> NAME/KEY: misc_feature
<222> LOCATION: (1)..(1)
<223> OTHER INFORMATION: n = biotin molecule

<400> SEQUENCE: 46
naagagctta agaaccgtca gacagaaaag aggattatta tacc                       44

<210> SEQ ID NO 47
<211> LENGTH: 96
<212> TYPE: DNA
<213> ORGANISM: Artificial Sequence
<220> FEATURE:
<223> OTHER INFORMATION: Target Nucleic Acid Molecule

<400> SEQUENCE: 47
tccggagcga gttacgaaga caaaacctct tcgttgaccg atgtactctt gtagaaagtt      60
ataataatcc tcttttctgt ctgacggttc ttaagc                                96

<210> SEQ ID NO 48
<211> LENGTH: 25
<212> TYPE: DNA
<213> ORGANISM: Artificial Sequence
<220> FEATURE:
<223> OTHER INFORMATION: Forward Primer

<400> SEQUENCE: 48
cttgtgctaa tcgcagtaac ctaat                                            25

<210> SEQ ID NO 49
<211> LENGTH: 23
<212> TYPE: DNA
<213> ORGANISM: Artificial Sequence
<220> FEATURE:
<223> OTHER INFORMATION: Reverse Primer

<400> SEQUENCE: 49
accaagagca actcaccgaa ttc                                              23
```